(12) United States Patent
Barak et al.

(10) Patent No.: US 7,637,879 B2
(45) Date of Patent: Dec. 29, 2009

(54) METHOD AND APPARATUS FOR ASSISTING VASCULAR FLOW THROUGH EXTERNAL COMPRESSION SYNCHRONIZED WITH VENOUS PHASIC FLOW

(75) Inventors: Jacob Barak, Oranit (IL); Adi Dagan, Zichron Yaakov (IL); Amir Fabian, Zichron Yaakov (IL)

(73) Assignee: Medical Compression Systems, (DBN) Ltd., Or-Aqiva (IL)

( * ) Notice: Subject to any disclaimer, the term of this patent is extended or adjusted under 35 U.S.C. 154(b) by 879 days.

(21) Appl. No.: 11/023,894

(22) Filed: Dec. 28, 2004

(65) Prior Publication Data

US 2005/0159690 A1 Jul. 21, 2005

Related U.S. Application Data

(60) Provisional application No. 60/533,060, filed on Dec. 29, 2003.

(51) Int. Cl.
*A61H 7/00* (2006.01)
*A61H 19/00* (2006.01)

(52) U.S. Cl. .................. 601/152; 601/149; 601/150; 601/151

(58) Field of Classification Search ................ 601/148, 601/149, 150, 151, 152; 602/13; 606/201, 606/202; 128/DIG. 20
See application file for complete search history.

(56) References Cited

U.S. PATENT DOCUMENTS

| 5,514,079 | A | | 5/1996 | Dillon |
| 5,588,955 | A | | 12/1996 | Johnson, Jr. et al. |
| 5,674,262 | A | | 10/1997 | Tumey |
| 5,840,049 | A | | 11/1998 | Tumey et al. |
| 5,931,797 | A | | 8/1999 | Tumey et al. |
| 6,231,532 | B1 | * | 5/2001 | Watson et al. ............... 601/150 |
| 6,592,527 | B2 | * | 7/2003 | Oser et al. .................. 600/481 |
| 6,810,542 | B1 | * | 11/2004 | Mitchell ....................... 5/630 |
| 7,048,702 | B2 | * | 5/2006 | Hui ............................. 601/152 |
| 2003/0233118 | A1 | | 12/2003 | Hui |

FOREIGN PATENT DOCUMENTS

| WO | WO 00/06076 | 2/2000 |
| WO | WO 2004/041146 | 5/2004 |

OTHER PUBLICATIONS

XP 0023965546 Schmidt et al., "Physiologie des Menschen" 1990, Springer Verlag pp. 524-528.

* cited by examiner

*Primary Examiner*—Justine R Yu
*Assistant Examiner*—Kristen C Matter
(74) *Attorney, Agent, or Firm*—Gauthier & Connors LLP

(57) ABSTRACT

An automatic portable ambulant miniaturized system for applying pneumatic pressure to a body limb including a portable ambulant hand-held fluid source unit, a conduit for delivering fluid generated by the unit, and a pressure sleeve coupled to the conduit and adapted to envelop a body limb. The pressure sleeve contains individually inflatable cells, each cell being subdivided into longitudinally extending confluent intra-cell compartments along the axis of the body limb. The intra-cell compartments are inflated and deflated essentially simultaneously by the portable fluid source unit. To increase the peak venous velocity generated by any kind of external compressive force on a limb with any kind of tempo-spatial regime, the venous phasic flow is monitored to determine so that the venous flow generated by the external compressive force can be synchronized with the in-phasic natural venous flow.

30 Claims, 40 Drawing Sheets

|  | T1 | T2 | T3 | T4 | T5 | T6 | T7 |
|---|---|---|---|---|---|---|---|
| VALVE 1 | + | − | − | − | − | − | − |
| VALVE 2 | + | + | − | − | − | − | − |
| VALVE 3 | + | + | + | − | − | − | − |
| VALVE 4 | − | − | − | + | − | − | − |
| VALVE 5 | − | − | − | + | + | − | − |
| VALVE 6 | − | − | − | + | + | + | − |
| COMPRESSOR | + | + | + | + | + | + | + |

FIG. 7

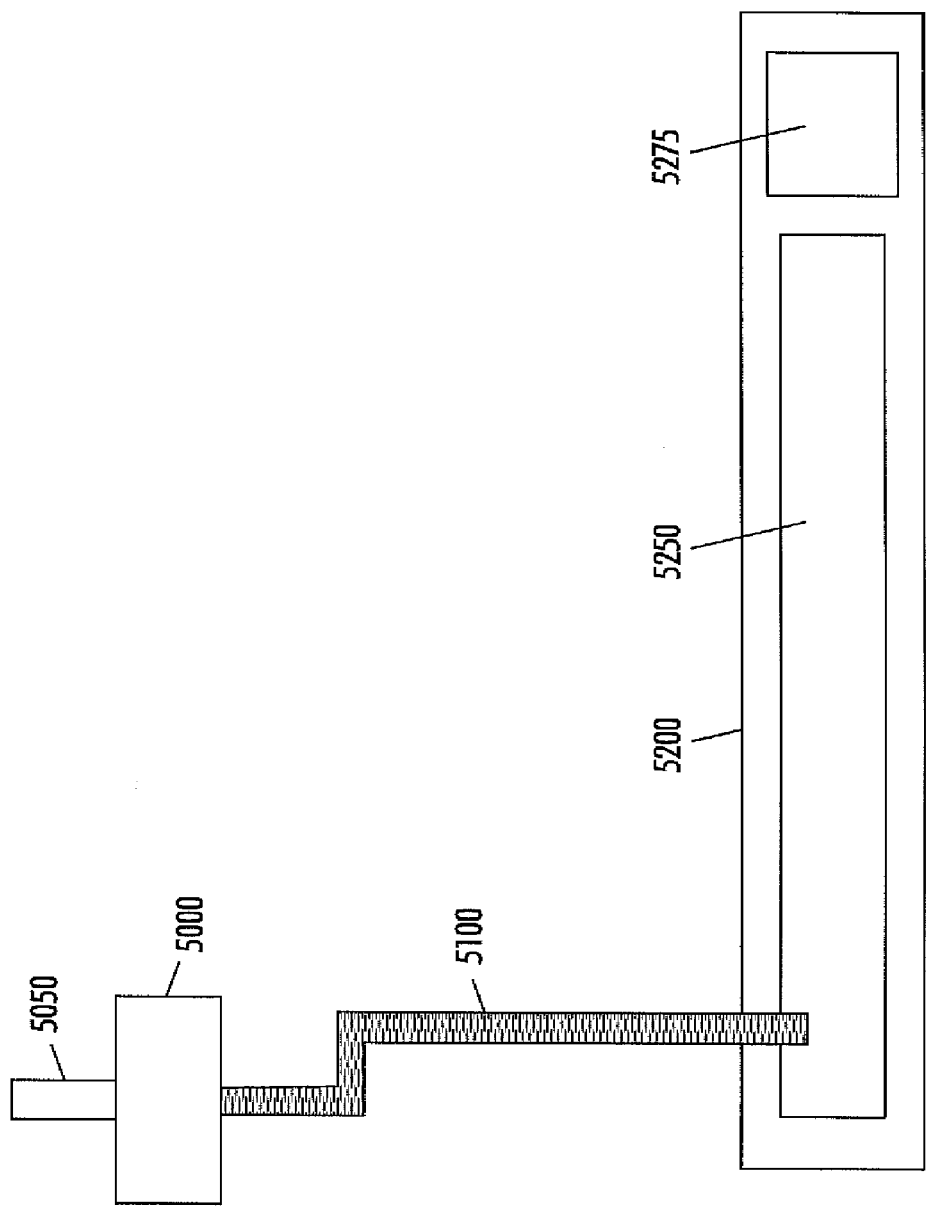

METHOD AND APPARATUS FOR ASSISTING VASCULAR FLOW THROUGH EXTERNAL COMPRESSION SYNCHRONIZED WITH VENOUS PHASIC FLOW

PRIORITY INFORMATION

This application claims priority under 35 U.S.C. §119 to U.S. Provisional Patent Application Ser. No. 60/533,060, which was filed on Dec. 29, 2003. The entire content of U.S. Provisional Patent Application Ser. No. 60/533,060 is hereby incorporated by reference.

FIELD OF THE PRESENT INVENTION

The present invention relates to medical devices for applying pressure to a region of a body surface. More particularly, the present invention relates to medical devices that use a pressure sleeve with or without a pressure accumulator to apply pressure to a region of a body surface in synchronization with the venous phasic flow.

BACKGROUND OF THE PRESENT INVENTION

Therapeutic intermittent compression of the limbs for the enhancement of blood circulation has been in use for the last couple of decades. A variety of conventional devices have been developed for the therapeutic intermittent compression of the limbs, with many being specifically developed for the prevention of deep vein thrombosis ("DVT") after surgeries, others where developed and used for the treatment of arterial related problems such as peripheral vascular disease and diabetic ulcers. Thrombosis creation is effected by three major parameters, which are known as the Virchov's triad, namely: venous stasis, hypercoagulability state, initial damage to the tissues and/or the blood vessel wall.

Therapeutic intermittent compression of the leg, by pneumatically compressing the limb or using other mechanical compressive force upon the limb, uses the technique of cyclically compressing the limb so as to enhance circulation of blood. The compressive force exerted on the limb is mediated to the vein through the tissues causing it to constrict, thereby emptying the blood within it.

Improving the venous return is known to have a positive effect on the increase of the local arterial flow probably through the mechanism of increasing the Δp across the capillaries and through the increase in local synthesis of metabolites, prostacyclin (PGI2) and endothelial derived relaxing factor (NO). Both metabolites are synthesized by the endothelial cells as a response to the increase in shearing forces. The metabolites are considered the most potent native vasodilators available in the human body.

The period of compression is typically short (up to a few seconds) and the interval between pulses longer (more then 30 sec) which is the time it usually takes the veins to refill after being emptied by the relatively short pulse of compression.

The external compression methodology's favorable effect is derived from its ability to increase the peak venous velocity, thereby combating the stasis factor. The short period of increased linear venous flow velocity has also been demonstrated to significantly enhance blood clearance from the soleal sinuses, the axial veins, and the valve sinuses. Moreover, it has been shown that the cyclic increase in peak venous velocity, which mimics the flow pattern during walking, also increases the shearing forces on the endothelial cells resulting in several fold increase in the release of important bio-chemical mediators such as tissue plasminogen activator, tissue factor pathway inhibitor, nitric oxide, and prostacyclin, all serving as the bodies own anti-coagulant factors and therefore effecting it's hypercoagulability state.

Since increase peak venous velocity provides many benefits, it has become an objective of various conventional devices to create high peak venous velocities through mechanisms that will be well tolerated by the patients. As studies have shown, the velocity of venous flow is proportional to the pressure exerted on the limb and to the rate at which the pressure rises. Thus, systems have been developed to create relatively high pressures (70-130 mmHg) with relatively high rate of pressure rise (0.3-1 sec) in order to show improvements in flow outcome (peak venous velocity) over slower inflating devices.

Various conventional compression devices are known for applying compressive pressure to a patient's limb. These types of devices are used to assist in a large number of medical indications, mainly the prevention of deep vein thrombosis (DVT), vascular disorders, reduction of edemas, and the healing of wounds. Prior art devices are typically divided into two main segments: 1) a hospital segment, in which the conventional compression devices are used mainly for the prevention of DVT and 2) a home segment, in which the conventional compression devices are mainly used to treat severe lymphedema. Although showing high clinical efficacy in clinical studies in treating the above clinical indications, the conventional compression devices share many disadvantages that severely hamper their clinical out come in real life situations.

For example, the conventional compression devices use a conventional main power supply (wall outlet), and thus impose confinement upon the patient during the long periods of treatment e.g.: in DVT prevention after surgeries, the patients should be on therapy continuously from before the operation until discharge on a 24/7 basis. Confinement to the bed for receiving continuous treatment with a conventional device is impractical and is hardly ever achieved. Moreover the need to stay lying in bed for long periods of time delays recuperation, can lead to the development of pressure ulcers, and is contra-indicated to good medical practice.

The pump unit of the conventional compression device is heavy (5-15 pounds), which makes it hard to maneuver and place in the vicinity of the patients. The pump unit is also big and thus creates a storage problem, specifically in hospitals, in which tens and hundreds of units are stationed, usually in a special storage room. The sleeve of the conventional compression device is big and ungainly, and thus restricts the movement of the limb it encompasses and imposes discomfort. In addition, the use of multiple cells demands the use of multiple conduits (usually one for each cell) making the whole system more cumbersome and harder to maneuver.

Moreover, data corresponding to the pressure and compression cycles of the conventional compression systems has to be manually entered into the system by the clinical staff each time the system is turned ON. Furthermore, since the error detecting mechanism of the conventional systems shuts OFF the system each time an error is detected, the system needs to be manually restarted by the clinical staff, thereby requiring the clinical staff to manually re-enter the data corresponding to the pressure and compression cycles. In other words, in view of the need to manually enter the data corresponding to the pressure and compression cycles upon each start-up of the compression system and in view of the shutting down of the system upon error detection, with the accompanying re-entry of data, the conventional compression systems are overly dependent upon clinical staff for operation, thereby unduly imposing on the workload of the clinical staff.

All of the aforementioned disadvantages result in poor patient and therapist (mainly nurses) compliance and compliant. Clinical studies have proven that daily compliance of the systems is less then 50% resulting in far below expectation clinical outcomes compared to a continuous treatment ("Prophylaxis against DVT after Total Knee Arthroplasty," by Geoffrey H. Westrich, *The Journal of Bone and Joint Surgery*, Vol. 78-A, June 1996 & "Why does Prophylaxis with External Pneumatic Compression for DVT fail?" by Anthony J. Comerota, *The American Journal of Surgery*, Vol. 164 September 1992).

As noted above, in many medical conditions it is desirable to apply pressure to a region of the body surface. Conventionally, this is accomplished by fixing one or more individually inflatable cells to the body surface. When the cells are inflated, a pressure is applied to the body surface in contact with the cell. When the cell is deflated, the pressure is relieved. The cells are usually incorporated into a sleeve that is placed around a body limb to be treated. The limb may be, for example, a leg, an arm, a hand, a foot, or the trunk.

The cells may be toroidal in shape when inflated so as to completely surround the limb. A cell may be maintained in an inflated state for a prolonged period of time in order to apply prolonged pressure to the underlying body region. Alternatively, a cell may be inflated and deflated periodically so as to apply intermittent pressure to the underlying body region. A sleeve having one or more individually inflatable cells will be referred to herein as a pressure sleeve.

FIG. 20 schematically shows a prior art system for applying pressure to a body limb. The system uses a pressure sleeve (not shown) comprising one or more individually inflatable cells. The system also includes a console 615 containing a compressor 602 that generates pressurized air. A conduit 607 conducts the flow of pressurized air away from the compressor 602. A number of solenoid valves (605a, 605b, and 605c) equal to the number of cells in the pressure sleeve are positioned along the conduit 607. Each valve (605a, 605b, and 605c) has an air inlet connected to an upstream portion of the conduit 607, a first air outlet connected to a downstream portion of the conduit 607, and a second air outlet (611a, 611b, and 611c) connected to an associated cell via a conduit (614a, 614b, and 614c). Each valve can alternate between an open state in which pressurized air can flow between the inlet and the first outlet and the second outlet (611a, 611b, and 611c) and a closed state in which pressurized air can flow between the inlet and the first outlet, but not between the inlet and the second outlet (611a, 611b, and 611c).

The console 615 further comprises a processor 619 that controls the state of each of the valves (605a, 605b, and 605c) so as to execute a predetermined temporo-spatial array of inflation of the cells. For example, in one application the cells are inflated peristaltically so that one cell is first inflated, while the other cells are deflated. As illustrated in FIG. 16, this can be accomplished by the processor 619 opening the valve 605a while the valves 605b and 605c are closed. Pressurized air flows in the conduit 607 from the compressor 602 into the cell associated with conduit 614a. The processor 619 monitors the air pressure in the conduit 607 by means of a pressure gauge 603. When the pressure has reached a predetermined level, the processor 619 closes the valve 605a. Next, the cell associated with conduit 614b is inflated by opening the valve 605b. A one-way valve 625 prevents the flow of air in the conduit 607 from flowing from the valves (605a, 605b, and 605c) towards the compressor 602. The cell associated with conduit 614a is then deflated and the cell associated with conduit 614c is inflated. The cells associated with conduit 614b and 614c are then deflated, and the cycle can begin again.

The console 615 has a housing 620 containing the processor 619, the conduit 607, and the valves (605a, 605b, and 605c). The compressor 602 may be located within the housing of the console 615 as shown in FIG. 20. In the conventional compression system, as shown in FIG. 20, pressure in the cells rises gradually, starting when the valve 605a is opened until the final pressure is achieved. However, in some medical conditions it is beneficial to produce a fast inflation of the sleeve encompassing the body surface. Studies have shown that the velocity of venous flow or the increase in local arterial flow is proportional to the rate at which the pressure rises. In the prevention of DVT, it is believed that this acceleration of venous flow reduces the risk of pooling and clotting of blood in the deep veins and therefore the rate of pressure rise is a critical variable of effectiveness in the prevention of DVT. In order to achieve a rapid inflation, it is known to incorporate in the housing 620 of the console 615 a pressure accumulator.

FIG. 21 shows schematically another conventional compression system for applying pressure to a body limb incorporating a pressure accumulator 740. This conventional compression system contains several components in common with the conventional compression system shown in FIG. 20. As illustrated in FIG. 21, a solenoid valve 705a is positioned on the conduit 707 upstream from the valves (705b, 705c, and 705d). The valve 705a has an air inlet connected to an upstream portion of the conduit 707, a first air outlet connected to a downstream portion of the conduit 707, and a second air outlet connected to the pressure accumulator 740 via a conduit. The valve 705a can realize an open state in which flow of fluid may occur between the inlet, the first outlet, and the second outlet. The valve 705a can also realize a closed state in which flow of fluid may occur between the inlet and the first outlet but not between the second outlet and the inlet or between the second outlet and the first outlet. The processor 719 determines the operational state of valve 705a.

The conventional compression system shown in FIG. 21 is used when it is desired to apply pressure rapidly to a portion of a body limb underlying the cell. In this application, the valve 705a is opened while the valves (705b, 705c, and 705d) are closed, causing pressurized air to flow in the conduit 707 from the compressor 702 through the valve 705a into the accumulator 740. When the pressure in the accumulator 740 reaches a predetermined value $P_A$, as determined by the pressure gauge 703, the processor 719 opens the valve 705b causing air to flow from the accumulator 740 into the cell associated with valve 705b. The pressure in the cell associated with valve 705b will rise rapidly to a pressure $P_C$. $P_A$ and $P_C$ satisfy the relationship $P_A V_A = P_C(V_A + V_C)$ where $V_A$ is the volume of the accumulator 740 and $V_C$ is the volume of the cell associated with value 705b when inflated. The valves 705b, 705c, and 705d are then operated as described in reference to the system of FIG. 20.

Systems of the type shown in FIG. 21 having an accumulator inside the console are disclosed, for example, in U.S. Pat. Nos. 4,653,130 and 5,307,791 to Senoue et al.; U.S. Pat. No. 5,027,797 to Bullard; U.S. Pat. No. 5,840,049 to Tumey et al.; and U.S. Pat. No. 5,588,955, to Johnson et al. The entire contents of U.S. Pat. Nos. 4,653,130; 5,307,791; 5,027,797; 5,840,049; and 5,588,955 are herby incorporated by reference.

As illustrated in FIG. 21, the presence of the accumulator 740 within the housing 720 of the console 715 adds to the size of the console 715. Thus, adding an accumulator to the console of a system that is otherwise miniature, mobile and battery operated makes the console, and hence the entire system, immobile, which destroys the advantages and benefits of a mobile system.

All the above-described devices use a pump, a reservoir that receives pressurized air from the pump, an inflatable cuff for sequentially applying pressure to a limb, and means for intermittently and quickly transmitting pressurized air from the reservoir to the inflatable cuff. The triggering mechanism for the compression cycles used in these devices is a timer that is set to initiate the compression cycle every 30-50 seconds (depending on the specific system) with out taking into consideration the phasic nature of the venous flow in the recombine position. This phasic flow is created mainly by the changes in the intra-abdominal pressure that is caused by the respiration mechanism. During inspiration, the contraction of the diaphragm muscle causes an increase in the intra-abdominal pressure, and the contrary happens during expiration. Triggering the compression cycle regardless of the natural phasic venous flow creates non-consistent, non-reproducible peak venous velocities.

In other words, the effects of external compression being applied during expiration (when the intra-abdominal pressure is least) will be positively reinforced and/or enhanced by the lower intra-abdominal pressure, the lower pressure acting to draw the blood, thereby effectively increasing the potential peak venous velocity. On the other hand, the effects of external compression being applied during inspiration (when the intra-abdominal pressure is greatest) will be adversely impacted and/or diminished by the higher intra-abdominal pressure, the higher intra-abdominal pressure acting to block or pushback the blood flow, thereby effectively lowering the potential peak venous velocity and compromising the efficacy of the device. Moreover, it is now understood that the increase of the peak venous velocity by the external compression is dependent on the exact point in the phasic flow in which the external pressure was administrated. Since conventional devices use timers as the triggering mechanism, the measured peak venous velocities for these devices vary tremendously.

In summary, the external compression generated venous flow being in-phase with the phasic nature of the venous flow creates a positive synergistic effect and a high peak venous velocity, whereas external compression generated venous flow being out of phase with the phasic nature of the venous flow is subjected to negative interference from the phasic nature of the venous flow.

Therefore, it is desirable to provide a compression system that provides external compression generated venous flow in synergistic synchronization with the phasic nature of the venous flow. More specifically, it is desirable to provide a compression system that provides external compression generated venous flow during times of lower intra-abdominal pressure. Furthermore, it is desirable to provide a compression system that provides external compression generated venous flow in synergistic synchronization with the respiration cycle of the patient. In addition, it is desirable to provide a compression system that is small, ambulant, and portable. It is also desirable to provide a compression system that provides patients with continuous 24/7 treatments and freedom of movement. It is further desirable to provide a compression system that is suitable for home use and can be stored easily and/or allows a user to engage in social activities during treatment. Lastly, it is desirable to provide a compression system that includes a pressure accumulator that is small, ambulant, and portable.

SUMMARY OF THE PRESENT INVENTION

A first aspect of the present invention is a system for applying pressure to a limb of a body. The system includes a compression system to provide controlled therapeutic pressure to a limb of a body to generate an induced venous flow and a sensor, in operative communication with the compression system, to measure a venous phasic flow of a patient and to provide data representing the measured venous phasic flow to the compression system. The compression system, in response to the sensor, provides controlled therapeutic pressure to a limb of a body such that the induced venous flow generated by the compression system will be in-phase with the measured venous phasic flow of the patient.

A further aspect of the present invention is a compression system for applying therapeutic pressure to a limb of a body. The system includes a pressure sleeve and a compression system console, pneumatically connected to the pressure sleeve, having a controller to provide controlled pressurized fluid to the pressure sleeve such that the controlled pressurized fluid induces a venous flow in-phase with a venous phasic flow of a patient.

A further aspect of the present invention is a system for applying pressure to a limb of a body. The system includes a compression system to provide controlled therapeutic pressure to a limb of a body to generate an induced venous flow and a respiration sensor, in operative communication with the compression system, to measure a respiration cycle of a patient and to provide data representing the measured respiration cycle to the compression system. The compression system, in response to the respiration sensor, provides controlled therapeutic pressure to a limb of a body such that the induced venous flow generated by the compression system will be in-phase with a venous phasic flow of the patient.

A further aspect of the present invention is a method of providing therapy to a limb of a patient with a pressure device. The method monitors a venous phasic flow of a patient and applies therapeutic pressure to a limb of the patient in-phase with the venous phasic flow of the patient.

A further aspect of the present invention is a method of providing therapy to a limb of a patient with a pressure device. The method monitors a respiration cycle of a patient; determines a venous phasic flow of the patient from the monitored respiration cycle; and applies therapeutic pressure to a limb of the patient in-phase with the determined venous phasic flow of the patient.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein:

FIG. 7 is a table of programmed control parameters for a control unit in the case of two three-chambered sleeves according to the concepts of the present invention;

FIG. 50 illustrates a block diagram of a pressure cuff according to the concepts of the present invention.

DETAILED DESCRIPTION OF THE PRESENT INVENTION

Figure 1:
FIG. 1 is an illustration showing a pressure device according to the concepts of the present invention in use on the leg of a patient.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention as defined by the appended claims. For a general understanding of the present invention, reference is made to the drawings. In the drawings, like reference have been used throughout to designate identical or equivalent elements. It is also noted that the various drawings illustrating the present invention are not drawn to scale and that certain regions have been purposely drawn disproportionately so that the features and concepts of the present invention could be properly illustrated.

In the following, an embodiment of the present invention will be described for use on the leg of an individual. However, it is to be understood that the present invention is also intended for use on any body limb such as an arm, a leg, a foot, a part of a leg, a part of arm, or a part of foot, and may be used on two or more limbs simultaneously.

Venous flow to the heart is generated by the calf muscles constricting on the vein, an effect referred to as the muscle pump, or, while the calf muscles are inoperative (such as in the supine position during hospitalization) by the increase/decrease in intra-abdominal pressure caused by the respiratory action of the lungs and which is referred to as the phasic recombine position flow. This natural flow of venous blood in the veins in the supine position has a sinusoidal pattern. The intra-abdominal pressure is directly affected by the respiratory cycle: during inspiration the contraction of the diaphragm muscle causes an increase in the intra-abdominal pressure, and during expiration, the relaxation of the diaphragm muscle causes a decrease in the intra-abdominal pressure.

According to the concepts of the present invention, in-phase synchronization of the external compressive force generated venous flow with this natural flow (sometimes of residual nature) will create a positive effect upon blood flow, thereby increasing the magnitude of the amplitude (which is the peak venous velocity) of the venous blood wave surging in the veins. On the other hand, according to the concepts of the present invention, external compressive pressure generated venous flow that is out of phase with this natural flow will create a negative effect, thereby reducing the magnitude of the amplitude (peak venous velocity).

To increase the peak venous velocity generated by any kind of external compressive force on a limb with any kind of tempo-spatial regime, the present invention synchronizes the effect of the external pressure generated venous flow with the in-phasic natural flow; e.g., periods of lower intra-abdominal pressure. On the other hand, applying external pressure during increased intra-abdominal pressure significantly decreases the peak venous velocity in the lower limbs. Therefore, the present invention synchronizes the venous flow generated by the inflation of the pressure/compression sleeves of an external compression system to periods of lower intra-abdominal pressure.

In general, the present invention monitors the venous phasic flow of the patient using an external pressure/compression system to increase peak venous velocity. The external pressure/compression cycle generated venous flow from the applying of pressure to the limbs to force blood through the veins is in-phase with the venous phasic flow. The determination of the venous phasic flow can be realized in many ways.

In a preferred embodiment of the present invention, the venous phasic flow is determined by monitoring the respiration cycle of the patient; however, it can be determined by directly monitoring the blood flow of the patient or other bio-characteristics of the patient that are related to venous phasic flow. Moreover, the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

Figure 43:
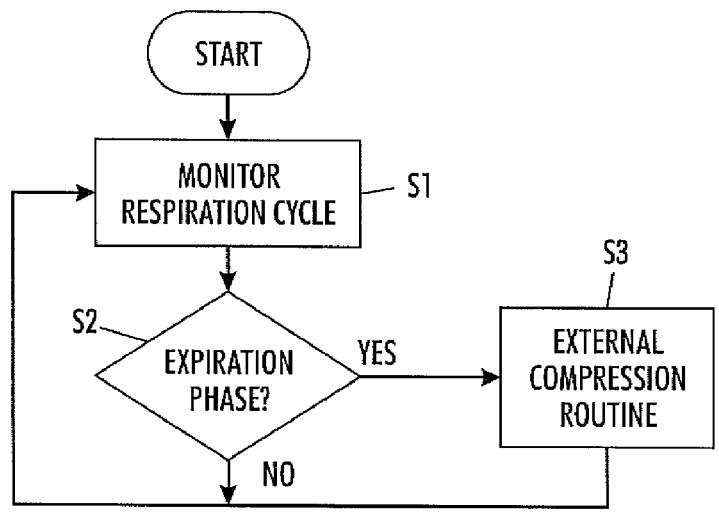
FIG. 43 is a flowchart showing one embodiment of the external compression sequence according to the concepts of the present invention.

FIG. 43 illustrates a flowchart of the methodology utilized by one embodiment of the present invention. As illustrated in FIG. 43, the present invention monitors, at step S1, the respiration cycle of the patient using an external pressure/compression system to increase peak venous velocity. As noted above, the monitoring of the respiration cycle is only one example of monitoring the venous phasic flow of the patient. The present invention may utilize any signal or sensor to provide the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof.

At step S2, it is determined if the respiration cycle is in an expiration phase. If an expiration phase is detected, step S3 allows an external pressure/compression cycle to create the pressure in such a way that the pressure/compression will be applied to the vein at the time of expiration; e.g., during a time of lower intra-abdominal pressure; to force blood through the veins. It is preferred that the present invention starts inflating the pressure/compression sleeve prior to sensing the expiration as it takes time to create the pressure needed to force blood through the veins. In other words, the present invention creates the external pressure/compression in such a way that it will be applied to the vein at the time of expiration. If no expiration phase is detected, the external pressure/compression cycle remains in a wait state and the respiration cycle is monitored to detect the next expiration phase.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

Figure 44:
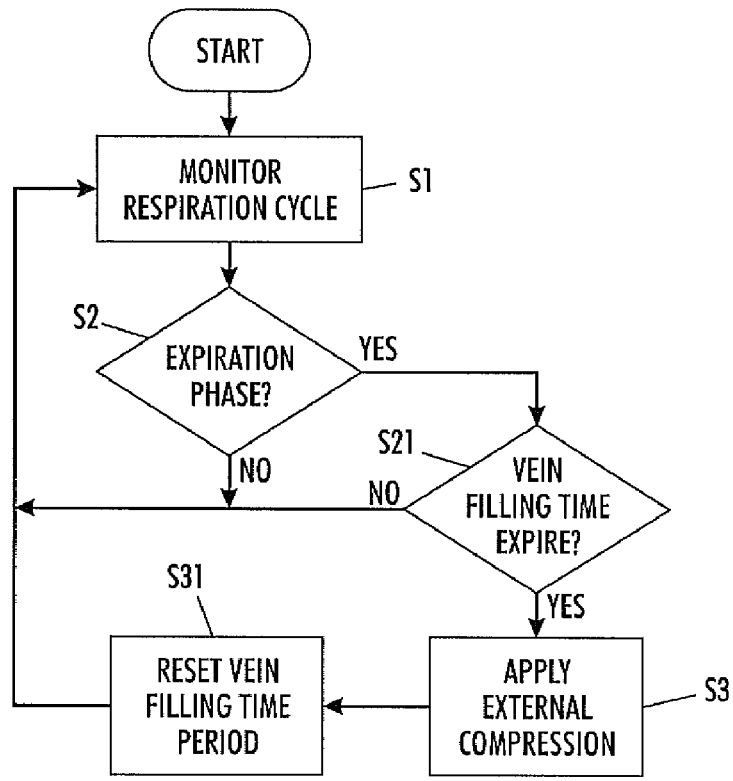
FIG. 44 is a flowchart showing another embodiment of the external compression sequence according to the concepts of the present invention.

FIG. 44 illustrates a flowchart of another methodology utilized by one embodiment of the present invention. As illustrated in FIG. 44, the present invention monitors, at step S1, the respiration cycle of the patient using an external pressure/compression system to increase peak venous velocity. As noted above, the monitoring of the respiration cycle is only one example of monitoring the venous phasic flow of the patient. The present invention may utilize any signal or sensor to provide the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof.

At step S2, it is determined if the respiration cycle is in an expiration phase. If an expiration phase is detected, step S21 determines if a predetermined amount of time has elapsed since the previous external pressure/compression cycle so as to allow the vein to refill for maximum blood volumetric blood flow. If step S21 determines that the predetermined amount of time has elapsed since the previous external pressure/compression cycle so as to allow the vein to refill for maximum blood volumetric blood flow, step S3 allows an external pressure/compression cycle to create the pressure in such a way that the pressure/compression will be applied to the vein at the time of expiration; e.g., during a time of lower intra-abdominal pressure; to force blood through the veins. It is preferred that the present invention starts inflating the pressure/compression sleeve prior to sensing the expiration as it takes time to create the pressure needed to force blood through the veins. In other words, the present invention creates the external pressure/compression in such a way that it will be applied to the vein at the time of expiration.

Upon initiating the external pressure/compression cycle, the predetermined time period is reset at step S31. If no expiration phase is detected or the predetermined amount of time has not elapsed since the previous external pressure/compression cycle so as to allow the vein to refill for maximum blood volumetric blood flow, the external pressure/compression cycle remains in a wait state and the respiration cycle is monitored to detect the next expiration phase.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

The preferred devices that provide the external pressure/compression includes a pressure sleeve having one or more inflatable cells, a pressurized fluid source, a programmable control unit, and a sensor system that can identify in real time the different phases of the venous flow; e.g., the different phases of the respiratory cycle. As noted in the above example, when the sensor system of the present invention identifies an in-phase venous phasic flow; e.g., the beginning of the expiration phase; it sends an electrical signal to the control unit. If, according to the pre-programmed operation algorithm the device is on "standby" for sleeve inflation, the control unit triggers the pressure source to inflate the pressure sleeves so that the external pressure/compression is applied in-phase with the venous phasic flow. The sleeve inflation will take place at the desired time interval in-phase with the venous phasic flow; e.g., in-phase with the respiratory cycle. The actual devices used to provide the external pressure/compression, according to the concepts of the present invention, are described in more detail below.

In FIG. 1, a patient is depicted wearing a massaging sleeve 1 of the present invention on her leg while carrying out her routine duties. In FIG. 1, the trouser leg of the patient is cut away to reveal the sleeve. In practice, however, the sleeve remains concealed from view, and remains unnoticed even during operation when the cells are intermittently inflated. The sleeve 1 has an inner and outer surface composed of a durable flexible material and is divided into a plurality of cells 2 along its length and each cell is connected to the control unit 3 by a separate tube collectively labeled 4 in FIG. 1. Sections of the sleeve may be of non-inflatable elastic material 5, for example around the knee and ankle.

As further illustrated in FIG. 1, the control unit 3 is attached to a respiration belt 20. The respiration belt 20 monitors the respiration cycle and provides signals to the control unit 3. As noted above, the monitoring of the respiration cycle is only one example of monitoring the venous phasic flow of the patient. The sensor 20 may be any sensor that is capable of providing data relative to the venous phasic flow. Moreover, FIG. 1 illustrates that the sensor is directly connected to the control unit 3; however, it is noted that the sensor 20 can also provide the data to the control unit 3 through a radio signal or other means of communication, thus the sensor 20 need not be physically connected to the control unit, only in communication therewith.

Upon receiving this data, the control unit 3 controls the operations so that external pressure/compression generated venous flow is in-phase with the natural venous phasic flow. In the example of FIG. 1, the realization of the external pressure/compression generated venous flow being in-phase with the natural venous phasic flow is the external pressure/compression generated venous flow being in-phase with an expiration phase or periods of low intra-abdominal pressure.

Figure 2:
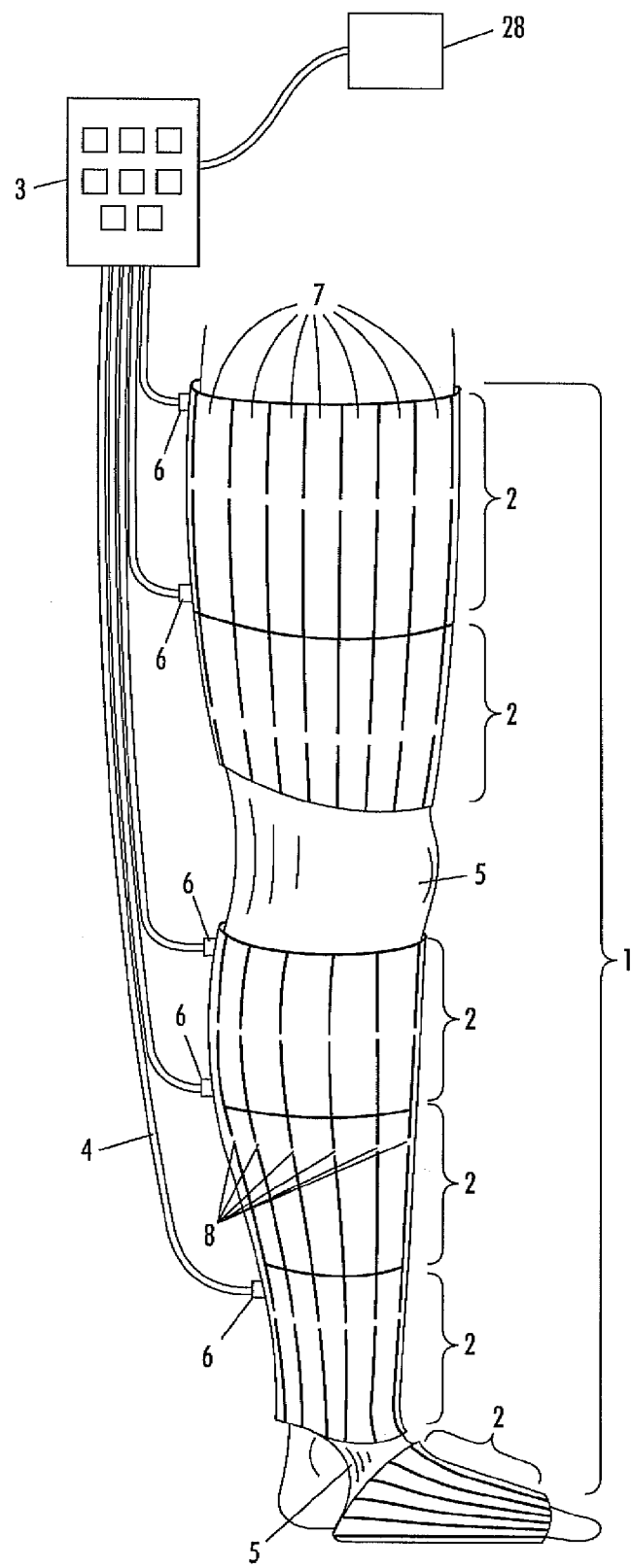
FIG. 2 is an illustration of a massage sleeve according to the concepts of the present invention mounted on the leg of a patient drawn to a larger scale.
Figure 3:
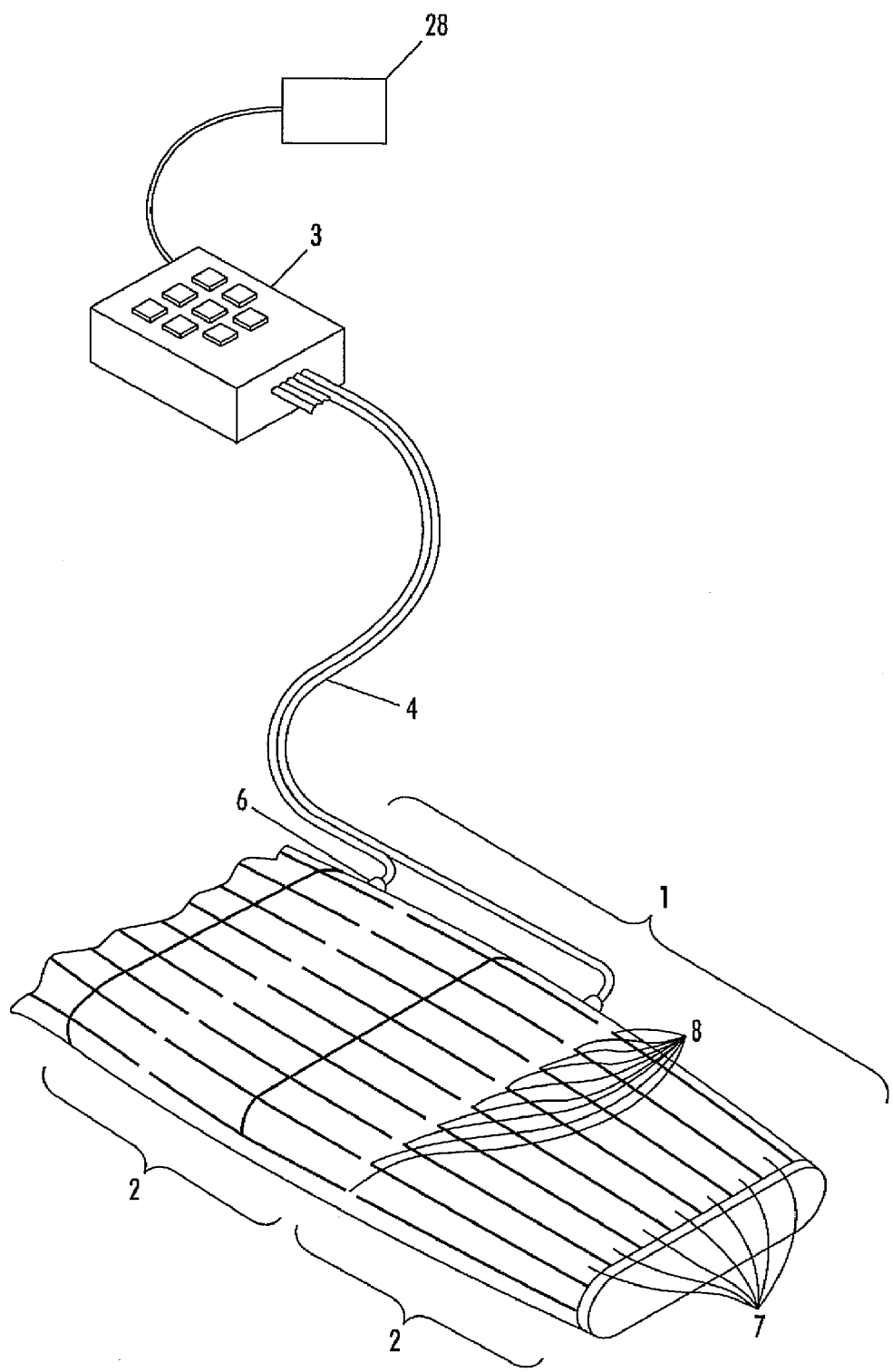
FIG. 3 is a partial perspective view of a massage sleeve according to the concepts of the present invention fitted with a control unit.

As can be seen in FIGS. 2 and 3, each cell has a fluid inlet opening 6 to which a hose 4 from the control unit 3 is attached. The control unit 3 contains a compressor capable of compressing and pumping ambient air into one or more selected cells in the sleeve via the hoses 4. Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

As further illustrated in FIGS. 2 and 3, the control unit 3 is attached to a respiration sensor 28. The respiration sensor 28 monitors the respiration cycle and provides signals to the control unit 3. The respiration sensor 28 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. As noted above, the monitoring of the respiration cycle is only one example of monitoring the venous phasic flow of the patient. The sensor 28 may be any sensor that is capable of providing data relative to the venous phasic flow.

Moreover, FIGS. 2 and 3 illustrate that the sensor is directly connected to the control unit 3; however, it is noted that the sensor 28 can also provide the data to the control unit 3 through a radio signal or other means of communication, thus the sensor 28 need not be physically connected to the control unit, only in communication therewith.

Upon receiving this data, the control unit 3 controls the operations so that external pressure/compression generated venous flow is in-phase with the natural venous phasic flow. In the examples of FIGS. 2 and 3, the realization of the external pressure/compression generated venous flow being in-phase with the natural venous phasic flow is the external pressure/compression generated venous flow being in-phase with an expiration phase or periods of low intra-abdominal pressure.

The control unit 3 allows a temporo-spatial regime of inflation and deflation of the cells to be selected, e.g. a regime which generates peristaltic contractions of the sleeve in synchronization with an expiration phase of the respiration cycle, a period of low intra-abdominal pressure, so as to force fluids inside the limb towards the proximal end of the limb, or a regime which enhances the flow of the venous blood in the limb.

In accordance with the present invention, the cells are subdivided into a plurality of longitudinally extending intra-cell compartments 7. The intra-cell compartments 7 are formed, for example, by welding the inner and outer shells of the massaging sleeve along the boundaries of the intra-cell compartments. The intra-cell compartments 7 in a given cell are confluent due to perforations 8 in the seams between adjacent intra-cell compartments 7 so that all the intra-cell compartments 7 in the cell are inflated or deflated essentially simultaneously. Each intra-cell compartment 7, when inflated, assumes essentially the shape of a cylinder having its axis parallel to that of the limb.

Figure 4:
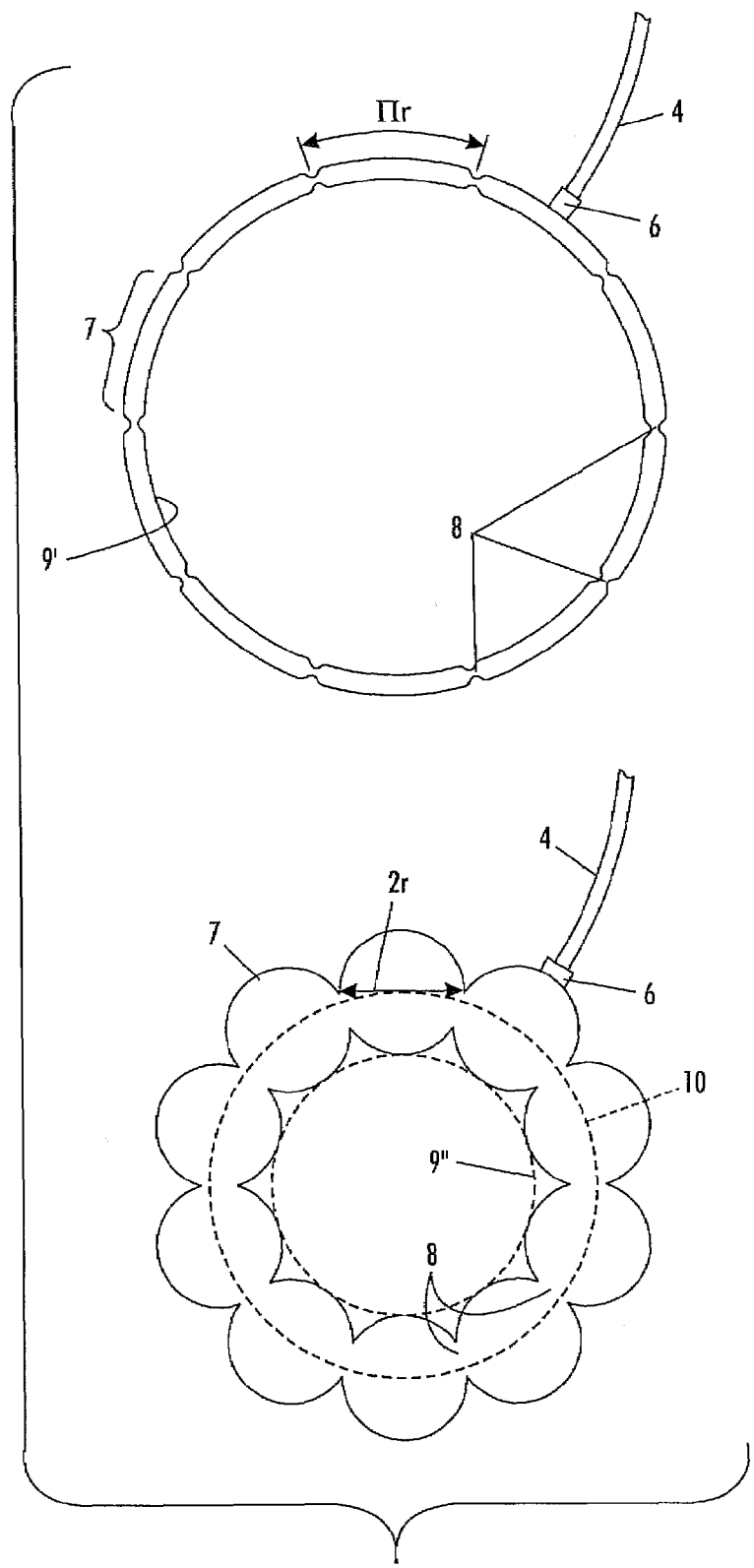
FIG. 4 is cross-section views of a cell in the deflated and inflated states, respectively, according to the concepts of the present invention.

A theoretical cross-section of a deflated cell is shown in FIG. 4, and FIG. 4S shows the same cross-section after inflation. The cell has been divided, by way of example, into ten intra-cell compartments 7, it being self-evident that any other number of intra-cell compartments may be used. If N is the number of intra-cell compartments in a given cell, and r is the radius of an inflated intra-cell compartment, then as can be seen in FIG. 4S the length of the circumference 10 that passes through the centers of the inflated intra-cell compartments 7 will be, theoretically, about 2Nr, whereas the circumference 9" of the deflated cell is, theoretically, about Nπr. The theoretical fractional decrease in the circumference upon inflation is thus $((N\pi r - 2Nr)/(\pi Nr)) \approx (1-2/\pi) \approx 0.36$. Due to various factors that will be discussed below in more detail, the length of the inner circumference 9" of the inflated cell, in actuality, will be something less than 2Nr so that the fractional decrease in the inner circumference upon inflation is thus less than or about 0.36. N and r are chosen so that πNr (the circumference of the deflated cell) corresponds to the original circumference of the limb segment contained within the lumen of the cell. The fractional decrease in the circumference of the cell upon inflation causes a contraction of the cell whereby pressure is applied to the limb that, as follows from the equation above, is independent of N and r.

Thus, by choosing N sufficiently large, and r correspondingly small, a sleeve is obtained having an inflated outer circumference not substantially larger than the original circumference of the limb. This is in contrast to conventional pressure sleeves, which must have a circumference greater than the initial circumference of the limb in order to achieve the same applied pressure as that produced by the present invention.

Letting now L be the height of a cell and $C=N\pi r+w$ wherein w is the length attributed by the widths of the compartmental welds between the intra-cell compartments, the initial circumference of the limb contained within the cell, it is readily appreciated from FIG. 4 that the initial volume of the limb contained within the deflated cell is $V_D=\pi(C/(2\pi))^2 L$. The final volume of the limb contained within the inflated cell is greater than $V_1=\pi(0.64C/(2\pi))^2 L=0.4V_D$.

Inflating the cell thus leads to a decrease in the volume of the limb contained within the cell of less than or about equal to 60%. This decrease in volume represents the volume of fluid squeezed out of the limb or the work performed by the sleeve. This is accomplished by inflating the intra-cell compartments of the cell to a total volume of $V_T=N\pi r^2 L=N\pi(C/N\pi)^2 L=(C^2 L)/N\pi$.

In contrast to this, obtaining the same decrease in the volume of the limb by conventional compression methods requires inflating a cell to a final volume of $V_F=\pi\{(1.36C/2\pi)^2-(0.64C/2\pi)^2\}L=(C^2 L)/(2.8\pi)$. Thus, when the number of intra-cell compartments in the cell of the present invention is at least 3, the volume to which the cell must be inflated is less than that of conventional compression devices. Moreover, choosing N to be sufficiently large can obtain a decrease of 59% in the volume of the limb by inflating the cell to an arbitrarily small total volume. For example, when N=30, the total volume of the inflated cell is theoretically less than one-tenth of the volume of the inflated cell of the conventional compression devices. This allows a much smaller compressor to be used than is possible with conventional sleeves, thus permitting the patient to be ambulatory while being treated by the present invention.

Figure 35:
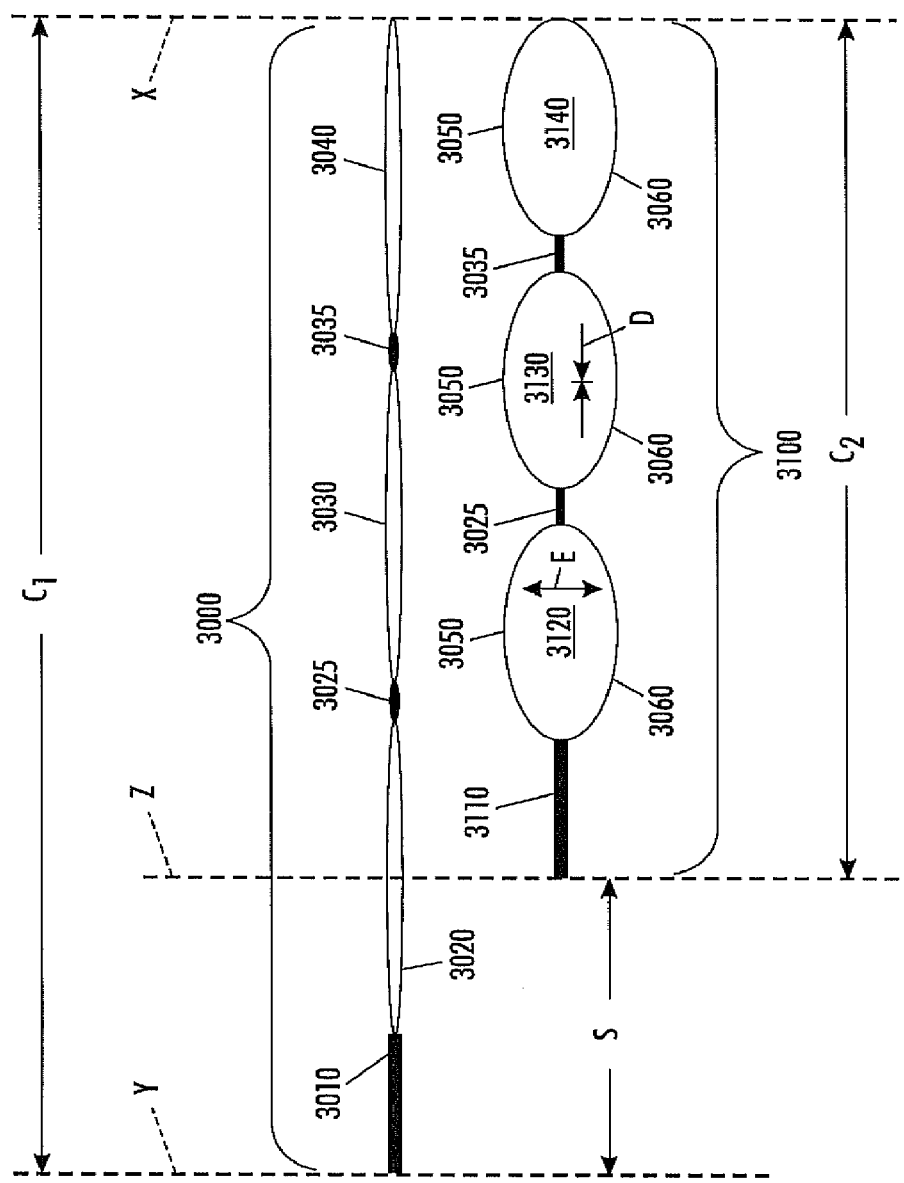
FIG. 35 illustrates the concept of circumferential constriction as employed by the present invention.

FIG. 35 provides a further illustration of the circumferential constriction concept of the present invention. As illustrated in FIG. 35, a deflated pressure sleeve 3000 includes a coupling device 3010, such as a hook and latch system, and three intra-cell compartments 3020, 3030, and 3040. It is noted that the coupling device 3010 couples or attaches to the intra-cell compartment 3040, in this example, to shape or form the pressure sleeve 3000 for therapeutic purposes. The three intra-cell compartments 3020, 3030, and 3040 are formed from perimetric welds or bonds (not shown) and compartmental welds or bonds 3025 and 3035. Between adjacent intra-cell compartments 3020 and 3030 is compartmental weld 3025, and between adjacent intra-cell compartments 3030 and 3040 is compartmental weld 3035.

When the pressure sleeve is deflated, as shown by pressure sleeve 3000, and is decoupled, the pressure sleeve realizes a first circumference value $C_1$ as measured between points X and Y. On the other hand, as illustrated in FIG. 35, when the pressure sleeve is inflated, as shown by pressure sleeve 3100, and is decoupled, the pressure sleeve realizes a second circumference value $C_2$ as measured between points X and Z. The difference between the first circumference value $C_1$ and the second circumference value $C_2$ is a shortening value S. As noted above the greater the value S, the greater the volume decrease of the limb caused by the inflated pressure sleeve.

It is noted that the shortening value S is affected by many parameters of the sleeve, such as: (1) the chemical and physical properties of the material used in constructing the sleeve (elasticity, flexibility, etc.); (2) the thickness of the material layer; (3) as noted above, the width of the welding lines or compartmental bonds; (4) the number of layers that are welded together; (5) the specific parameters of the welding procedure that is used and how it affects the chemical and physical characteristics of the material; and (6) the inflation pressure.

The integrated effect of all these parameters is very difficult to predict and thus to practically handle their integrated effect an empirical factor f is utilized to define the shortening value S, or in other words, the amount of circumferential constriction realized by the pressure sleeve for a given pressure. Using the empirical factor f, S is defined as $f((\pi-2)/\pi)(C_1-((N-1)B))$ wherein $C_1$ is the actual length of the cell, as illustrated in FIG. 35, and B is the width of a single weld between two adjacent compartments; e.g., welds 3025 or 3035 as illustrated in FIG. 35. The empirical factor f can be calculated for a pressure sleeve when it is inflated to a specific pressure.

Figure 36:
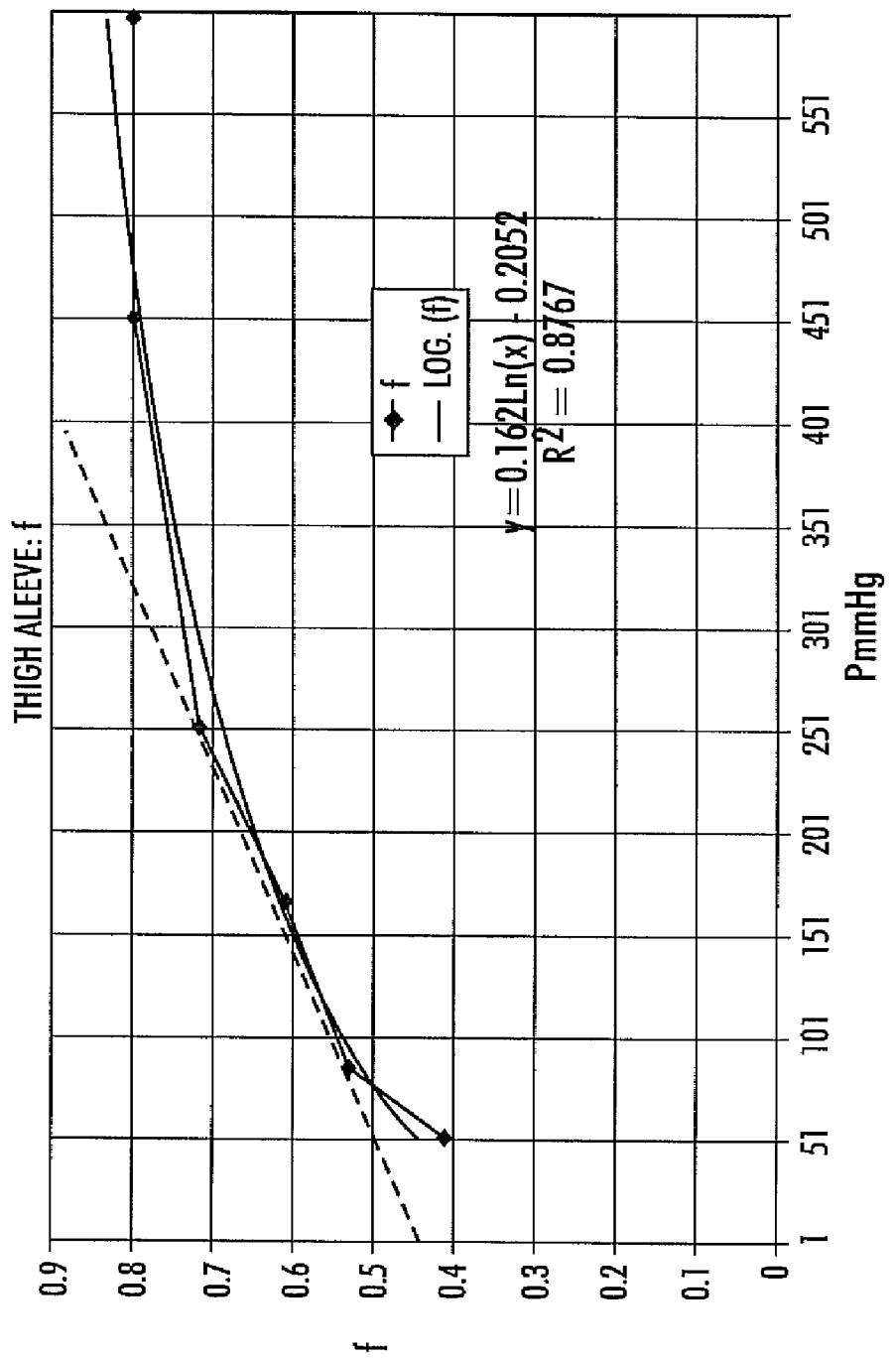
FIG. 36 graphically illustrates a relationship between pressure in an inflated pressure sleeve of the present invention and a constriction factor according to the concepts of the present invention.

For example, FIG. 36 illustrates a curve that defines the relationship between the various possible pressures within a pressure sleeve according to the concepts of the present invention and the empirical factor f. The empirical factor f was determined by filling the pressure sleeve to a predetermined pressure and then measuring its length to determine the shortening value S. Once S was determined, the above equation of $S=f((\pi-2)/\pi)(C_1-((N-1)B))$ was solved for f.

It is noted that pressures within the "clinical" or operational range (~75 mmHg to ~250 mmHg) are the pressures of real interest, and thus, within this range, it can be seen that the pressure within a pressure sleeve has a nearly linear relationship with the empirical factor f namely, $f=a+bp$ where b is the slope of the line passing through the measured data points between ~75 mmHg and ~250 mmHg, a is the f-axis intercept, and p is the specific pressure within the pressure sleeve. More specifically, using the illustrated example of FIG. 36, the empirical factor f would equal $0.43+0.00116p$. Therefore, using the above-described methodology of measuring the shortening value S of the pressure sleeve at various pressures with the clinical or operational range, the empirical factor f of the specific pressure sleeve can be determined.

In using the relationships discussed above, a pressure sleeve according to the concepts of the present invention, which has an actual length ($C_1$) of 385 mm, a single weld width (B) of 1.7 mm, an empirical factor f of 0.53 at 85 mmHg, and contains 15 adjacent intra-cell compartments (N), would have a shortening value of about 68 mm. Such a shortening value would result in an about 33% reduction in the volume of the limb surrounded by the sleeve.

As can be seen from the discussion above and from FIG. 35, the present invention provides a pressure sleeve that is capable of realizing a volume reduction of up to 60% depending upon the pressure in the sleeve, the width of the welds, the material of the inner and outer shells, etc.

Another reason for the improved reduction is the present invention's utilization of the intra-cell compartments. The intra-cell compartments, through the compartment bonds or welds (3025 and 3035), enables the present invention to realize a greater volume reduction with respect to the limb with less air than the conventional devices.

More specifically, as illustrated in FIG. 35, as the intra-cell compartments are inflated, the intra-cell compartments expand dimensionally in a direction substantially normal to the surface of the limb, as illustrated by the double-ended arrow E. Moreover, as illustrated in FIG. 35, as the intra-cell compartments are inflated, the intra-cell compartments contract dimensionally in a direction substantially coaxially to the surface of the limb, as illustrated by the opposing arrows D.

The simultaneous expansion in one dimension and contraction in a substantial normal direction of the intra-cell compartments provides a circumferential constriction of the pressure sleeve and thus reducing the volume of the underlying limb and causing blood to flow from the area. Moreover, due to the simultaneous expansion in one dimension and contraction in a substantial normal direction of the intra-cell compartments, the present invention can also utilize less area and realize the same volume reduction, thus increasing the life of the air compressor and reducing the energy consumption of the device.

It is noted that a sleeve according to the present invention, e.g. such as sleeve 1 in FIGS. 1 and 2 or a smaller sleeve covering only a portion of a limb, may be used for immobilization of a fractured bone in a limb.

Figure 5:
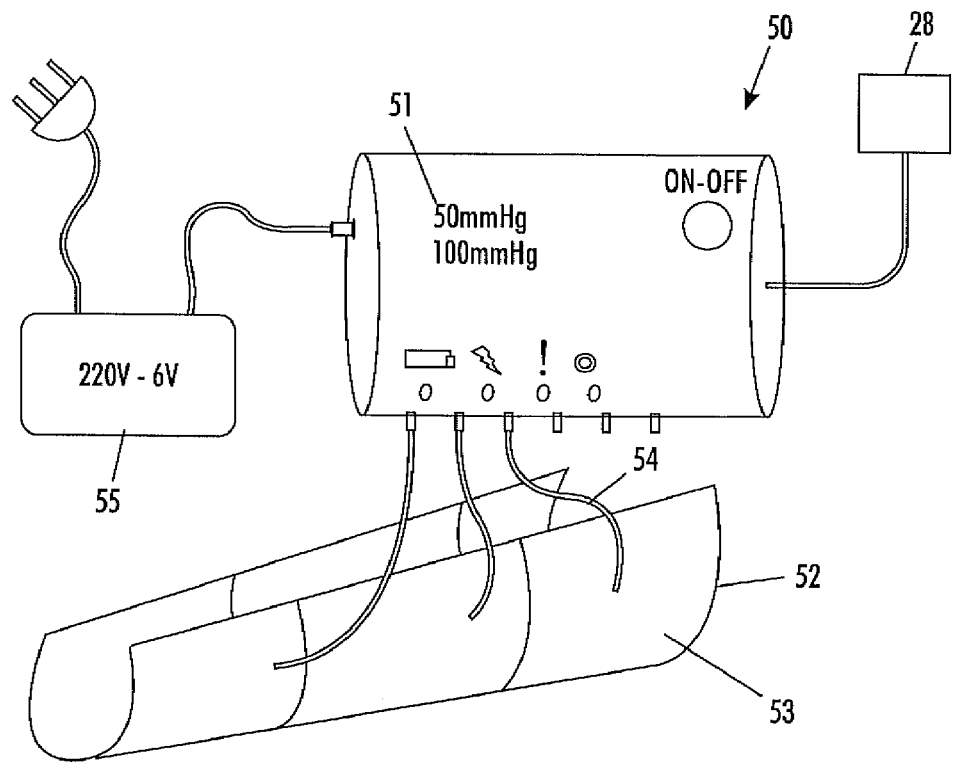
FIG. 5 is a block diagram of a pneumatic pressure system according to the concepts of the present invention.

FIG. 5 is a block diagram of a pressure system 50 includes a pump unit 51, which utilizes an electrical power supply/charger unit 55, such as a conventional electrical wall outlet, and an inflatable sleeve 52. The sleeve has a plurality of cells 53 arranged longitudinally along the sleeve. Conduits 54 connect the pump unit and the sleeve. The sleeve is placed over a limb and inflated, in some desirable cyclic manner by the pump unit, thus creating the desirable pressure cycle on the limb. It will be appreciated that the system can include at least one or more flexible sleeves 52 with single or multiple inflatable cells 53 adapted to be in contact with the body part to be treated. The best selection of a sleeve is one that requires small volume change to exert the needed pressure.

As further illustrated in FIG. 5, the pump unit 51 has a corresponding respiration sensor 28. The respiration sensor 28 monitors the respiration cycle and provides signals to the pump unit 51. The respiration sensor 28 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. As noted above, the monitoring of the respiration cycle is only one example of monitoring the venous phasic flow of the patient. The sensor 28 may be any sensor that is capable of providing data relative to the venous phasic flow.

Moreover, FIG. 5 illustrates that the sensor 28 is directly connected to the pump unit 51; however, it is noted that the sensor 28 can also provide the data to the pump unit 51 through a radio signal or other means of communication, thus the sensor 28 need not be physically connected to the pump unit 51, only in communication therewith.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

Upon receiving this data, the pump unit 51 controls the operations so that external pressure/compression generated venous flow is in-phase with the natural venous phasic flow. In the example of FIG. 5, the realization of the external pressure/compression generated venous flow being in-phase with the natural venous phasic flow is the external pressure/compression generated venous flow being in-phase with an expiration phase or periods of low intra-abdominal pressure.

Figure 6:
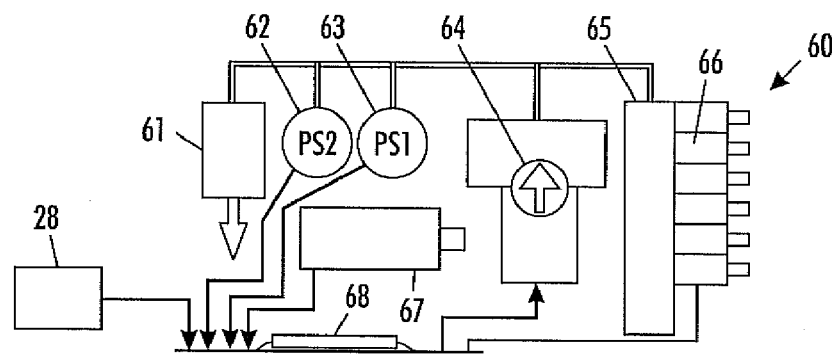
FIG. 6 is a schematic block diagram of a pump unit that corresponds to further details of the pump unit of FIG. 5, according to the concepts of the present invention.

FIG. 6 is a schematic block diagram of a pump unit 60 that corresponds to further details of the pump unit 51 of FIG. 5. It will be appreciated that the thick interconnecting lines represent pneumatic connections, while the thin interconnecting lines represent electrical connections. The pump unit 60 includes an independent source of energy, such as a rechargeable battery pack 67, which enable the pneumatic device operation without a fixed connection to a main power outlet. The batteries can be bypassed and the device is able to operate for longer times, and the batteries can be recharged at the same time, while it is connected to the main power supply with the aid of the charger 55.

As further illustrated in FIG. 6, the pump unit 51 is attached to a respiration sensor 28. The respiration sensor 28 monitors the respiration cycle and provides signals to the pump unit 51. The respiration sensor 28 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. As noted above, the monitoring of the respiration cycle is only one example of monitoring the venous phasic flow of the patient. The sensor 28 may be any sensor that is capable of providing data relative to the venous phasic flow.

Moreover, FIG. 6 illustrates that the sensor 28 is directly connected to the pump unit 51; however, it is noted that the sensor 28 can also provide the data to the pump unit 51 through a radio signal or other means of communication, thus the sensor 28 need not be physically connected to the pump unit 51, only in communication therewith.

Upon receiving this data, the pump unit 51 controls the operations so that external pressure/compression generated venous flow is in-phase with the natural venous phasic flow. In the example of FIG. 6, the realization of the external pressure/compression generated venous flow being in-phase with the natural venous phasic flow is the external pressure/compression generated venous flow being in-phase with an expiration phase or periods of low intra-abdominal pressure.

A source of compressed air, such as a compressor 64, is powered by the batteries or the main electrical outlet, and connected to the sleeve or sleeves 52 by pneumatic conduits 54. A control unit 68 is adapted to receive inputs from the operator and from pressure sensors 62 and 63. The control unit serves to read and control the operation of the compressor 64 and to control the cyclic inflating and deflating of the sleeve 53. The control unit also controls the operation of solenoid valves 66, which receive and distribute the flow to the different cells 53 with the aid of a manifold 65, to enable the sequential inflating and deflating of the multi-segmented sleeve's cells 53. It is noted that the compressor 64 may be housed with the control unit or may be housed separately.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

Alternatively both hardware and software of the current invention enables the operation of the device from an external pressurized air and power sources. In some hospitals the source of pressurized air can be the central source of pressure-regulated supply that has wall outlets adjacent to the power outlets or that both the external power and pump sources could be an integral part of the patient's bed.

The use of miniaturized components like the compressor 64 and solenoid valves 66, together with the miniature accessories, results in small power consumption that enables the operation of the pneumatic device on batteries, while maintaining small dimensions and lightweight of the operating unit. The use of a sleeve 53 with a small-inflated volume will improve the obtained results of the operation unit for better clinical operation and results.

The operation of the system of the present invention will now be described. Pneumatic devices apply cyclic sequential pressure on a body's legs or arms. The cyclic sequential pressure is applied on the treated parts of the body by inflating and deflating each cell 53 of the sleeve 52 at a predefined timing. While being inflated, the multi-chambered segmented sleeve 52 should be encircling the part of leg to be treated. While the sleeve is inflated, a local pressure is applied at the contact area between the sleeve and the body.

The control unit 68, which can be software based, controls the operation of the compressor 64 and solenoid valves 66. The control unit can be programmed to achieve any desired inflating and deflating sequence and timing including delay intervals, in accordance with clinical application. For example, in the case of two three-chambered sleeves (six solenoid valves), the controller can be programmed to operate in accordance with the table of parameters for the control unit shown in FIG. 7.

Each time interval from the table (T1, T2 . . . T7), as illustrated in FIG. 7, can be changed independently. The patient or the therapist can control the pressure level of the treatment. An example of an exemplary operation of the system in accordance with the present invention is illustrated in the flowchart of FIGS. 8-12, describing self-checks and error detection processes, attached pressure device identification process for identifying pressure devices such as pressure sleeve/sleeves, pressure accumulators, or combinations thereof, as well as normal operation of the system.

Figure 8:
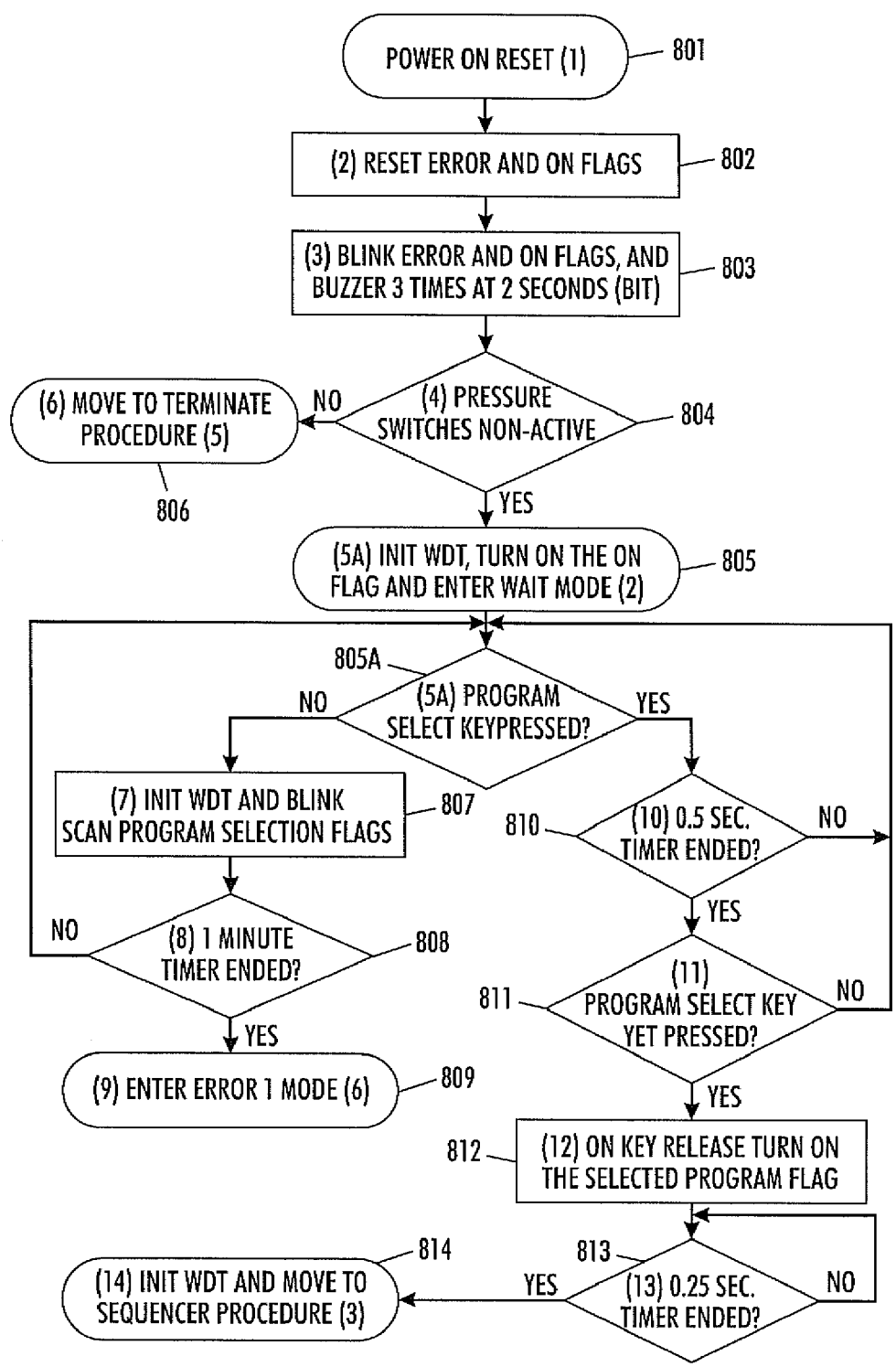
FIGS. 8-12 illustrate flowcharts of an exemplary operation of the system according to the concepts of the present invention.

In FIG. 8, the operation begins with on power reset (cold or hot) (801). The system initializes a built in test (BIT) procedure which checks the display, the buzzer and the pressure sensors (802, 803, and 804). If the sensors are found to be activated at this stage, the system holds (through termination procedure ((806) and 837-840)). If the BIT ends correctly, the system resets the watchdog timer (WDT), which prevents locking of the system and turns on the ON Flag (on the display) (805), and enters the WAIT mode, where it waits for a program (treatment) selection.

A WAIT procedure starts at step (805A) where keys are checked. If keys are not pressed, the system blinks the program flags at the display (807). If more than 1 minute has passed without any key pressed (808), the system enters error mode 1 ((809) and (841-845)). Restarting the system is the only way to go back from this mode of operation.

If a program key is pressed, the system de-bounces for 0.5 sec and then checks the keys again (810). If no key is pressed after the de-bounce time, the system returns to the start of the WAIT procedure. If a key is pressed after the de-bounce time, the system turns on the selected program flag (on the display) (812), and after a 0.25 sec delay (813) resets the WDT and starts the sequencer procedure (815).

Figure 9:
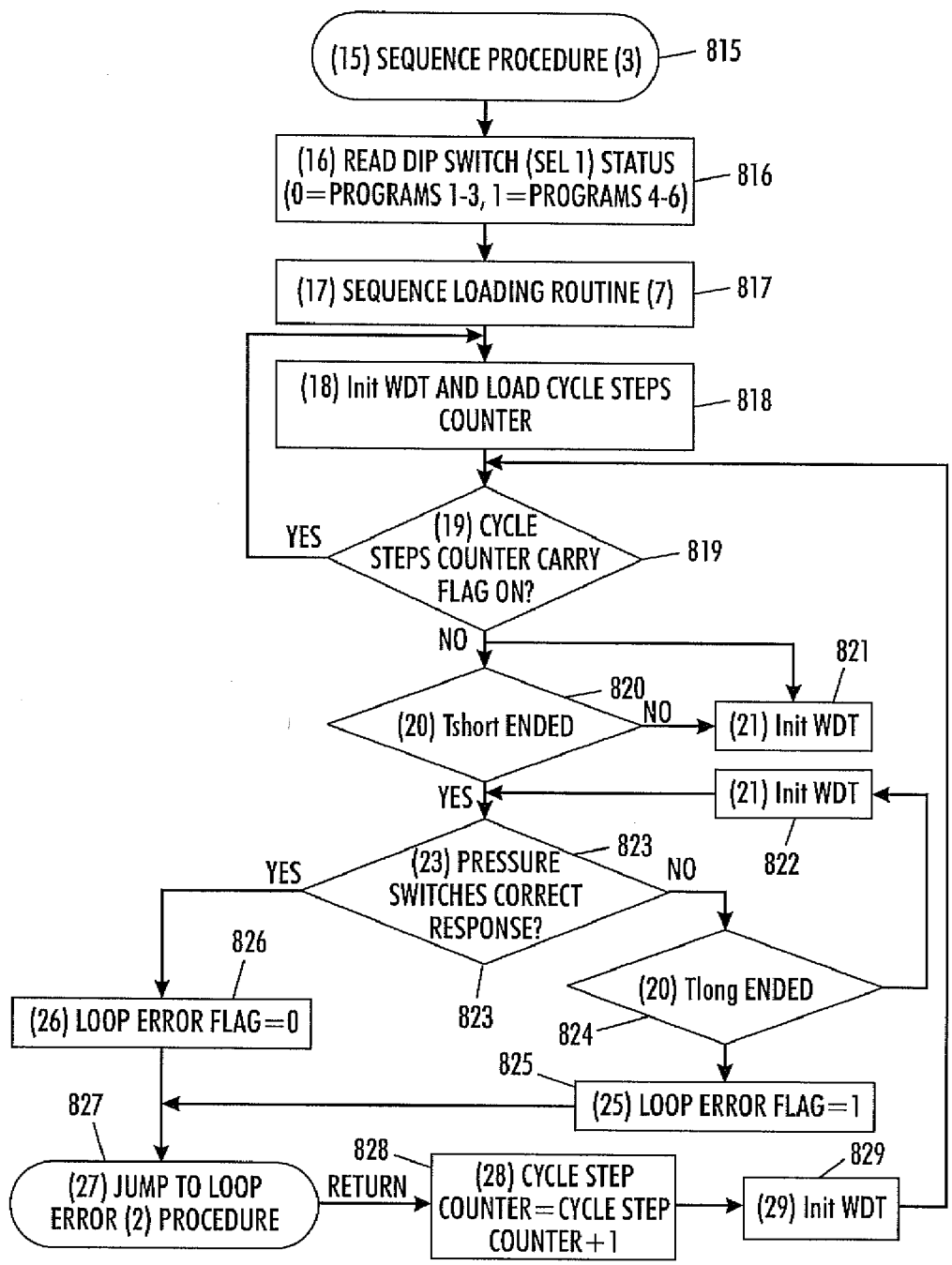

With reference now to FIG. 9, at the first stage in the procedure reads the program group (Dip Switch) on the board (816). Note that this switch is hidden from the user. At that time, the requested treatment program is well defined, and the system starts loading data (817). This data can be loaded from two different sources, one a preloaded sequence that is part of the content of the system controlling processor. The second source is the sleeve itself, equipped with a special connector and internal memory, which enables special treatments to be supported (plug and play procedure) (Detailed data of this procedure provided in (864-868)). After the sequence has been loaded, the WDT resets again, and data is entered to the cycle counter (which holds the sequence data, as previously supplied) (818).

The sequence starts by moving data to the pump and the valves and continues with a short period delay before checking the pressure sensors (820). Until this delay is finished, the system waits (820-821). After that, the system checks the sensors (823). If the sensors do not react correctly until the max available time (823, 824, 822), a sequence step error is stored (825). Later on, those errors will be analyzed (830-836). If the sensors reacted correctly at the time window, a non-error flag is stored (826). The system branches to the error analyzing procedure (827 and 830). If the system returns (not enough errors to hold), the cycle step counter advances (828, 829) and the next step starts (819).

Figure 10:
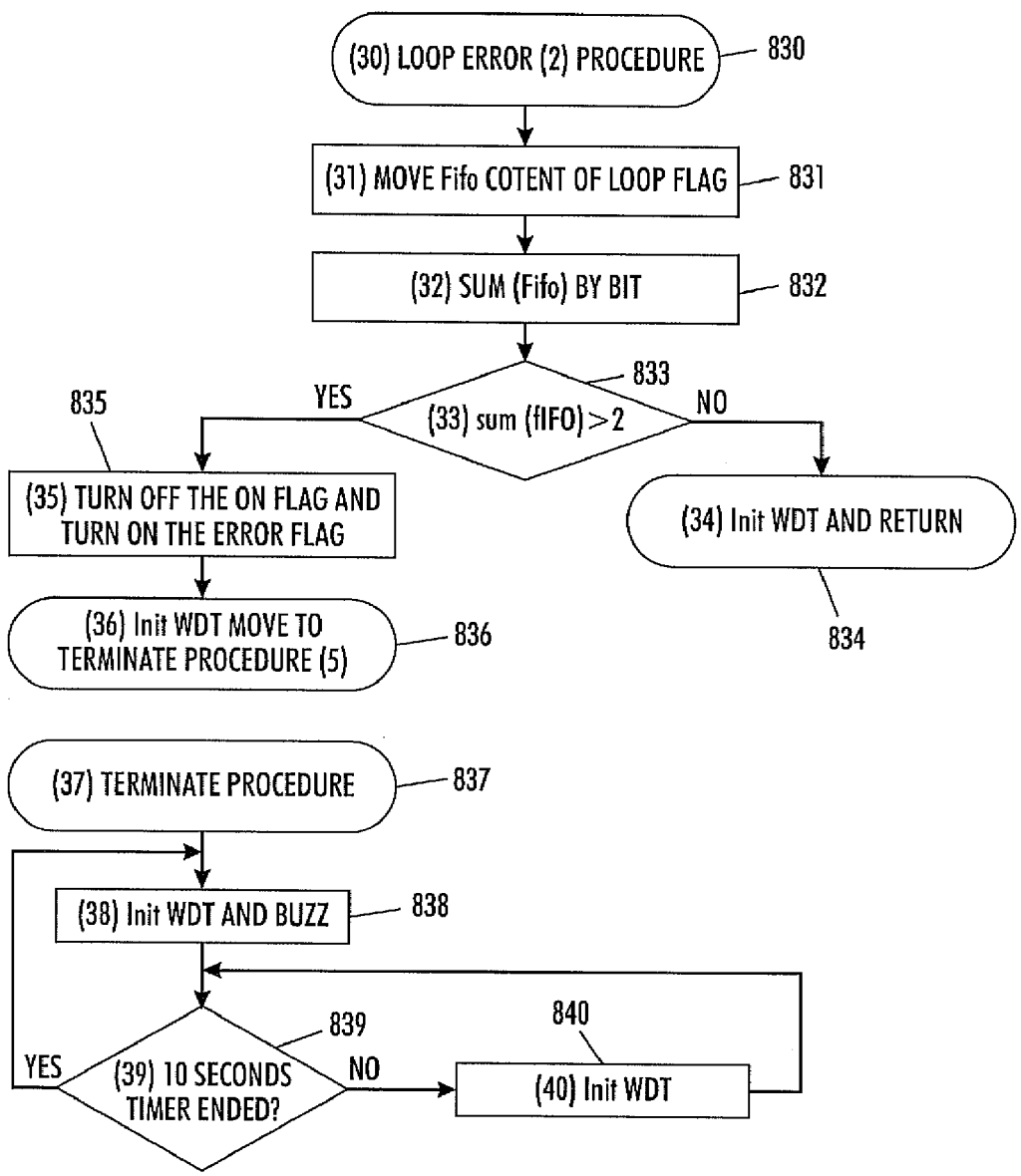

In FIG. 10, the error analyzing procedure (830) starts by storing the last calculated error flag in a 24 bits long FIFO register (831). The number of errors in the register is counted (832) and if the number exceeds 2, i.e., 3 errors in 24 steps, the system starts a HOLD procedure (835, 836). The HOLD procedure starts turning off the ON flag on the display, and turning on the ERROR flag, and then proceeds to the termination procedure (837-840).

If the number of errors does not exceed 2, the system initializes the WDT and returns to step (827) and continues. The termination procedure is as follows. The termination procedure starts at step (837) by operating the buzzer (838), and waits 10 seconds (839, 840) before re-operating the buzzer.

Figure 11:
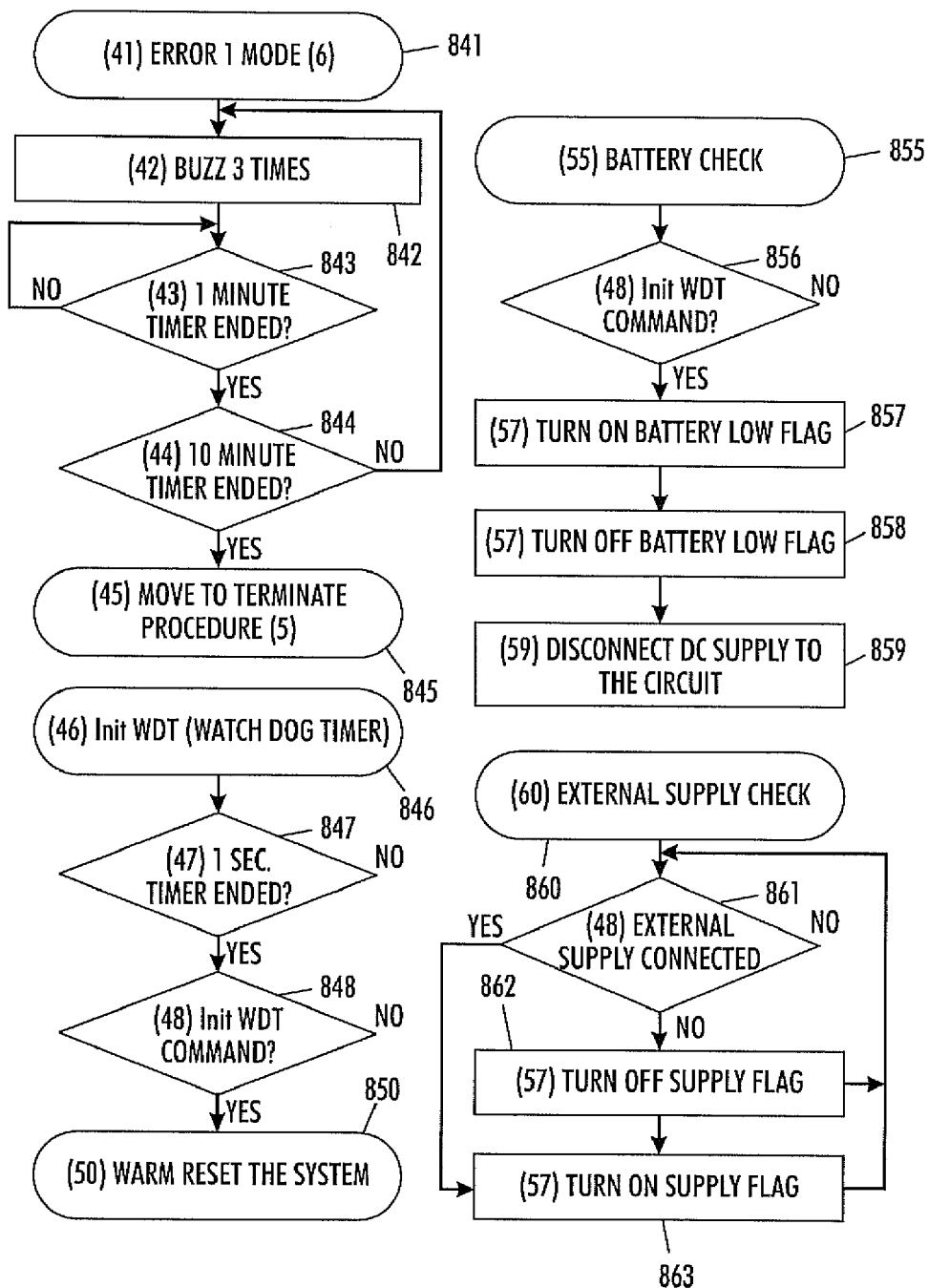

In FIG. 11, an error 1 procedure is described. The error 1 mode starts at step (841), operates the buzzer 3 times, waits 1 minute (843), and if time from start (841) did not exceed 10 minutes (844), it repeats the buzz procedure. If yes, the system moves into the termination procedure (845 and 837).

The WDT procedure starts at step (846), by resetting and re-programming the WDT counter to a 1 second interval. If, within this time interval (847) no WDT initialization pulse arrives (848), the WDT will reset the whole system (850).

Battery check procedure (855-859) uses hardware mechanisms that operate independently, without the software. External supply check procedure (860 to 863) uses hardware mechanisms that operate independently, without the software.

Figure 12:
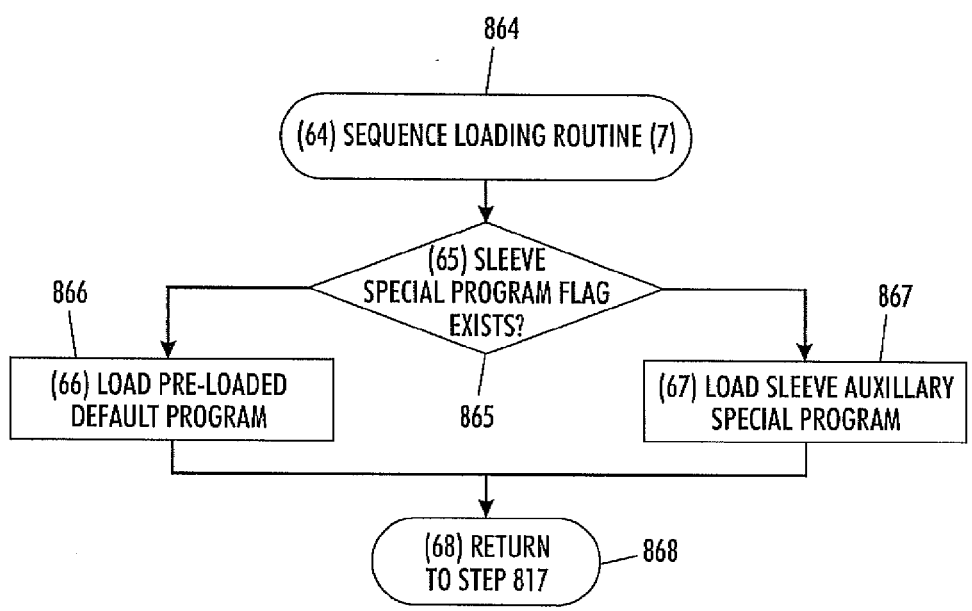

With reference to FIG. 12, an internal/external sequence loading procedure is shown. This unique function of the system enables use of both pre-loaded treatment sequences in the pump unit processor (internal) and to receive new treatments parameters from an electronic unit placed within the sleeve's connector (external). The sleeve connector to the system includes, together with the air tubes, an electronic memory and/or processing device, the presence of which is detected by the system. Detecting such a device causes the system to load the sequence data from the sleeve memory, and not from the pre-loaded memory, which is part of the processor. This is referred to conventionally as a "plug and play" mechanism.

The procedure starts at step (864), then the system checks the presence of an intelligent sleeve (865). If one exists, the sequence is loaded from the intelligent sleeve (867). If no intelligent sleeve is detected, then the pre-loaded sequence is loaded (866). Finishing loading the system causes the program to return to the next step (817).

Additional miniaturization and mechanical simplification of the portable ambulant pneumatic pressure system of the present invention can be achieved by introducing self-operated relief valves replacing the controlled operated solenoid valves. Another embodiment of a portable pneumatic pressure system 90 of the present invention is illustrated in FIG.

13. The system includes a pump unit 91, at least one inflatable sleeve 92 with a single cell or multiple inflatable cells 93 adapted to be in contact with the body part to be treated.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

Figure 13:
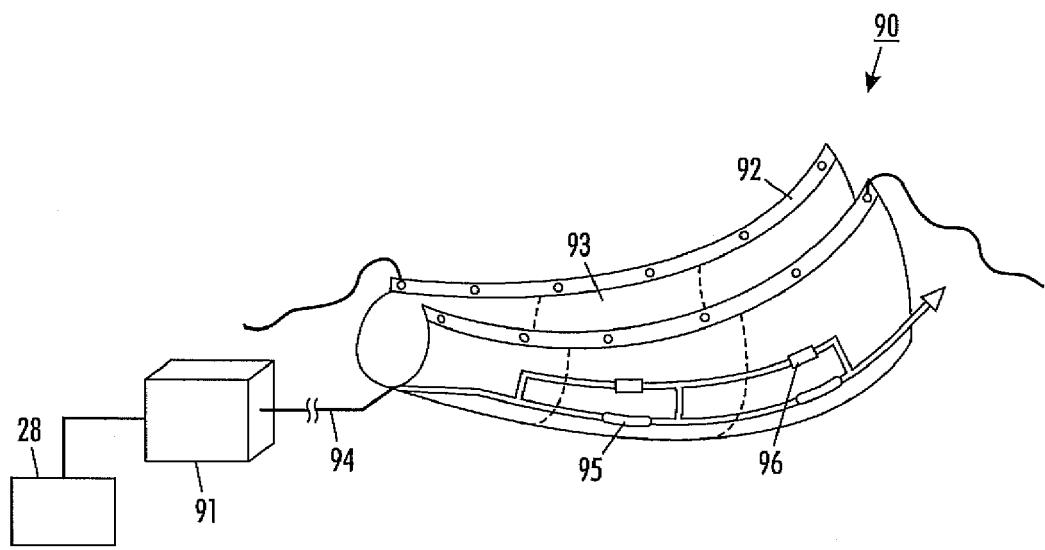
FIG. 13 is a block diagram of an alternative embodiment of a pneumatic pressure system according to the concepts of the present invention.

As further illustrated in FIG. 13, the pump unit 91 is attached to a respiration sensor 28. The respiration sensor 28 monitors the respiration cycle and provides signals to the pump unit 91. The respiration sensor 28 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. As noted above, the monitoring of the respiration cycle is only one example of monitoring the venous phasic flow of the patient. The sensor 28 may be any sensor that is capable of providing data relative to the venous phasic flow.

Moreover, FIG. 13 illustrates that the sensor 28 is directly connected to the pump unit 91; however, it is noted that the sensor 28 can also provide the data to the pump unit 91 through a radio signal or other means of communication, thus the sensor 28 need not be physically connected to the pump unit 91, only in communication therewith.

Upon receiving this data, the pump unit 91 controls the operations so that external pressure/compression generated venous flow is in-phase with the natural venous phasic flow. In the example of FIG. 13, the realization of the external pressure/compression generated venous flow being in-phase with the natural venous phasic flow is the external pressure/compression generated venous flow being in-phase with an expiration phase or periods of low intra-abdominal pressure.

An independent source of energy, for example rechargeable batteries, is provided which enables the pneumatic operation without a fixed connection to a main electrical power outlet, The batteries can be bypassed and thus system can operate for longer time periods while it is connected to the main power, and the batteries can be recharged at the same time.

Figure 14:
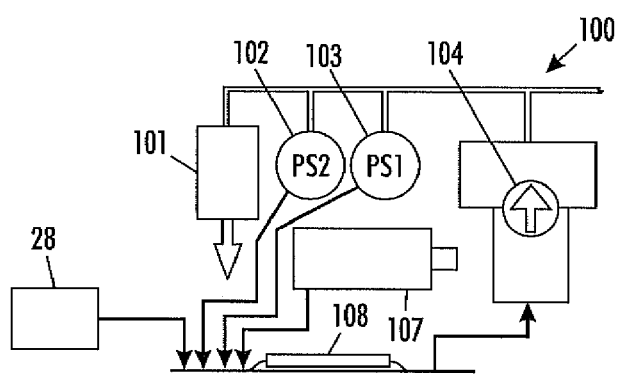
FIG. 14 is a schematic block diagram of a pump unit that corresponds to further details of the pump unit of FIG. 13.

FIG. 14 is a schematic block diagram of a pump unit 100 that corresponds to further details of the pump unit 91 of FIG. 13. It will be appreciated that the thick interconnecting lines represent pneumatic connections, while the thin interconnecting lines represent electrical connections. The pump unit 100 includes an independent source of energy, such as a rechargeable battery pack 107, which enable the pneumatic device operation without a fixed connection to a main power outlet. The batteries can be bypassed and the system is able to operate for longer times, and the batteries can be recharged at the same time.

A source of compressed air, such as a compressor 104, powered by the batteries or by the main power, is connected to the sleeve 92 or sleeves by one single pneumatic conduit 94, which enables inflating and deflating the cells 93. The compressor in this embodiment can enable the inverted flow to deflate the cells of the sleeve. It is possible to use a rotary compressor or to enable the inverted deflating flow by means of a valve, which may be solenoid operated and which is actuated by a control unit 108, or alternatively a pneumatic operated normally open valve can be used. The valve will be kept closed using the pressure of the compressor while the compressor is energized, and will open by itself when the compressor is stopped.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

As further illustrated in FIG. 14, the control unit 108 is attached to a respiration sensor 28. The respiration sensor 28 monitors the respiration cycle and provides signals to the control unit 108. The respiration sensor 28 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. As noted above, the monitoring of the respiration cycle is only one example of monitoring the venous phasic flow of the patient. The sensor 28 may be any sensor that is capable of providing data relative to the venous phasic flow.

Moreover, FIG. 14 illustrates that the sensor 28 is directly connected to the control unit 108; however, it is noted that the sensor 28 can also provide the data to the control unit 108 through a radio signal or other means of communication, thus the sensor 28 need not be physically connected to the control unit 108, only in communication therewith.

Upon receiving this data, the control unit 108 controls the operations so that external pressure/compression generated venous flow is in-phase with the natural venous phasic flow. In the example of FIG. 14, the realization of the external pressure/compression generated venous flow being in-phase with the natural venous phasic flow is the external pressure/compression generated venous flow being in-phase with an expiration phase or periods of low intra-abdominal pressure.

The control unit 108 is adapted to receive the operator's commands and control the operation of the compressor to control the cyclic inflating and deflating of the sleeve. Solenoid valves are replaced, in this embodiment, by self-operated relief valves 95, one with each chamber. The compressor is directly connected to the first cell. Each cell is connected to the next, one through a relief valve to regulate the pressure and maintain a pressure gradient. Each relief valve (except the last one) is bypassed with a conduit section including a check valve 96 to allow deflating of the cell. The last relief valve is open to the atmosphere, thus limiting the maximal pressure in the cells.

The control unit 108 controls the operation of the compressor 104 to inflate the first cell 93. The pressure in the first cell is built-up, and when it gets higher than the first relief valve 95 opening pressure, the second cell starts to be inflated. The third cell is inflated while the pressure in the second cell reaches the burst pressure of the second relief valve. The inflating process will continue in the same manner until the last cell is inflated. When the pressure in the last cell bursts the last relief valve, air will commence to flow out to the atmosphere preventing an uncontrolled pressure build-up inside the sleeve. When the operating interval of the compressor terminates, the controller de-energizes the compressor and enables all of the cells to be deflated simultaneously.

By using self-operated relief valves instead of the controlled solenoid valves, the system in accordance with the present invention will be smaller, lighter, have longer independent operation (as power consumption is reduced), and will be more cost effective. There will be a decrease in the operational flexibility because the relief valves are self-operated, and the controller is not able to control the inflating sequence of the cells.

The automatic portable ambulant pneumatic pressure system of the present invention is capable of treating more than one part of the body by connecting more than one sleeve to the pump unit. Sometimes, for medical reasons, the treatment is not symmetric on the body, i.e., treatment applied on the left calf and the right foot, and a different treatment is required in each sleeve. The sleeves used for the different treatments differ from each other by appearance because they are designed to operate on a different part of the body. They can also differ with the number of chambers and the connected conduits. The pump unit has the capability to operate each one of the sleeves with the appropriate medical treatment cycle.

The pump unit of the present invention can automatically identify the appropriate combination of treatments and/or pressures without requesting information from the operator. The operator selects the right sleeves and connects them to the pump unit. That will be sufficient for the system to identify the required treatment cycles and/or pressures and will prevent the possibility of mismatched input to the system by selecting a treatment and/or pressure, which is not suitable to the connected sleeves or vice versa.

To make a proper identification of the required treatment and or pressures, the present invention includes an identification system or process within the processor, which enables the present invention to correctly identify the combination of sleeves attached to it and automatically activates the appropriate operation algorithm. This capability is crucial if the device has to be kept as a user friendly "On/Off" device, in spite of its outstandingly high versatility depicted in its ability to operate foot/foot and calf/foot and thigh/calf/thigh sleeves and used on one or two legs with/with out pressure accumulator(s), and/or any proper combination thereof.

The identification system will now be briefly described. The present invention contains X solenoid operated valves, and each one of them is capable of connecting a pressure device, such as an air cell in a pressure sleeve or pressure accumulator, to a pressurized air source. The pressurized air source can be a central reservoir of pressurized air, internal or external air accumulator, or (usually) the air pump of the device itself. For each specific solenoid, two inflation time constants were determined: Tmax and Tmin.

A proper inflation time (Tn) of a pressure device has to be between Tmin and Tmax (Tmin<Tn<Tmax).

When Tn>Tmax in a normally functioning device, it means that either no pressure device was connected to the specific solenoid, that the pressure device that was connected is leaking, or the connected pressure device is not an authorized pressure device.

When Tn<Tmin in a normally functioning device, it means that the outflow tract of the specific solenoid is partially or completely blocked.

The above three described conditions are used by the present invention to correctly identify the pressure device or combination of pressure devices (wherein the pressure devices may be specialized pressure sleeves; such as foot pressure sleeves, calf pressure sleeves, thigh pressure sleeves or any combination thereof; pressure accumulators, or combinations thereof) attached to the present invention and automatically activates the appropriate operation algorithm.

A more detailed description of this identification process will be provided below in connection with the description of FIGS. 25-30.

Figure 25:
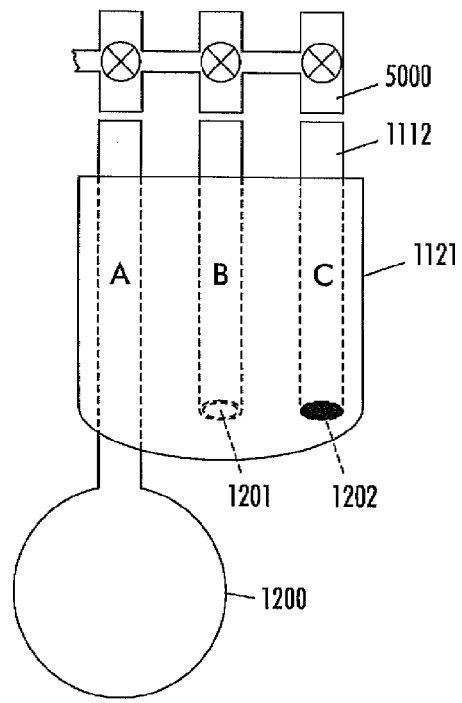
FIG. 25 illustrates possible states for an air channel or conduit connected to a pump device during an identification mode according to the concepts of the present invention.

After the present invention is turned ON, the present invention first runs a "checking program" that tests the inflation time (Tn) of each one of the X available solenoids. The test is done under "standard" pressure and pump flow conditions, and the solenoids are tested in sequence (1→X). For each solenoid, the inflation time Tn can be or Normal ("A") or >Tmax ("B") or <Tmin ("C"), as illustrated in FIG. 25. More specifically, as shown in FIG. 25, an air conduit connector 1121 with air conduits or flow tracts 1112, each associated with one of X solenoids 5000, shows the three possible operational states of an air conduit or flow tract 1112 attached to a solenoid 5000.

As illustrated in FIG. 25, one of the air conduits or flow tracts is connected to an authorized pressure device (in this example, an air cell) 1200, and thus, the microprocessor detects an operational state "A." Another air conduit or flow tract is connected to an unauthorized pressure device, no pressure device, or a leaking pressure device (1201), and thus, the microprocessor detects an operational state "B." Lastly, a third air conduit or flow tract is connected to a pressure device that is partially or completely blocked or a solenoid that is partially or completely blocked (1202), and thus, the microprocessor detects an operational state "C."

The sequence of the results in all X solenoids creates a specific code that is representative of the state of the pressure device and/or the type of the pressure device connected to each solenoid. If this code is recognized by the microprocessor as a valid one (one that appears in its lookup table), the microprocessor will switch the device from the "checking program" into the specific operation process or algorithm. If the created code does not appear in the lookup table, the created code will be identified as invalid, and the microprocessor will deactivate the device. In a preferred embodiment, an audiovisual alarm will be activated. Examples of the possible code generation are illustrated in FIGS. 26 through 30.

Figure 26:
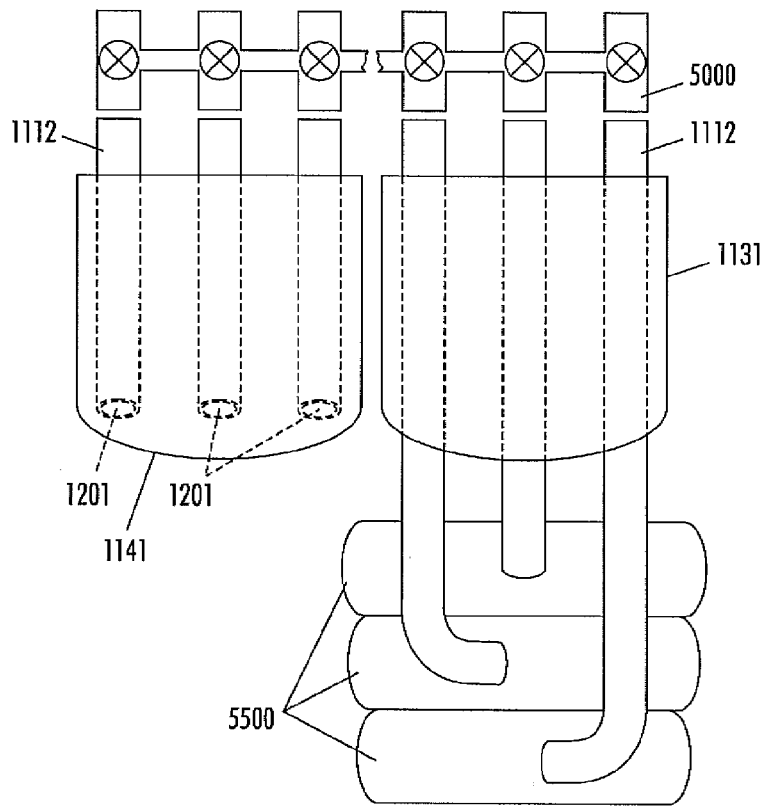
FIGS. 26-30 illustrate some of the possible combinations of pressure sleeve or pressure accumulator device connections to a pump device according to the concepts of the present invention.

In FIG. 26, an air conduit connector 1141 that has three air conduits or flow tracts 1112 connected to three solenoids 5000 will cause the microprocessor to create a code "BBB." As illustrated in FIG. 26, the code "BBB," in this example, is associated with air conduit connector 1141 being connected to no pressure devices (1201). Moreover, in FIG. 26, an air conduit connector 1131 that has three air conduits or flow tracts 1112 connected to three solenoids 5000 will cause the microprocessor to create a code "BBB." As illustrated in FIG. 26, the code "BBB," in this example, is associated with air conduit connector 1131 being connected to air cells 5500 of an unauthorized pressure device.

Figure 27:
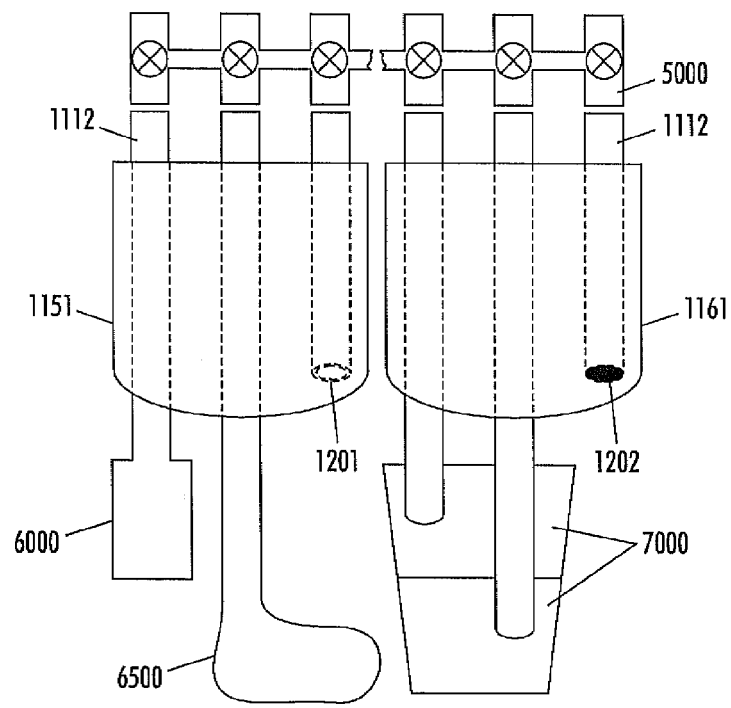

In FIG. 27, an air conduit connector 1151 that has three air conduits or flow tracts 1112 connected to three solenoids 5000 will cause the microprocessor to create a code "AAB." As illustrated in FIG. 27, the code "AAB," in this example, is associated with air conduit connector 1151 being connected to a pressure device comprising a pressure accumulator 6000, an air cell 6500 of a foot pressure sleeve, and no air cell 1201. Moreover, in FIG. 27, an air conduit connector 1161 that has three air conduits or flow tracts 1112 connected to three solenoids 5000 will cause the microprocessor to create a code "AAC." As illustrated in FIG. 27, the code "AAC," in this example, is associated with air conduit connector 1161 being connected to a pressure device having air cells 7000 of a double cell calf or thigh sleeve and blocked passage 1202.

Figure 28:
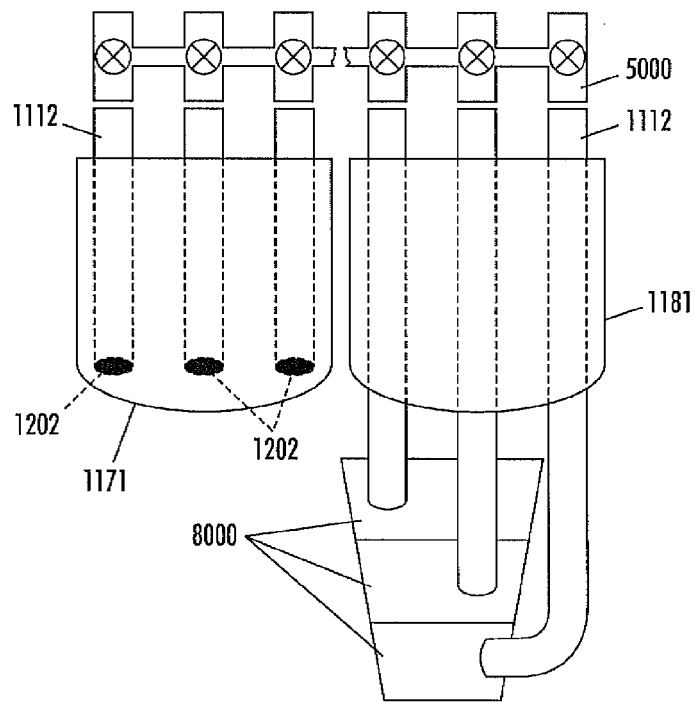

In FIG. 28, an air conduit connector 1171 that has three air conduits or flow tracts 1112 connected to three solenoids 5000 will cause the microprocessor to create a code "CCC." As illustrated in FIG. 28, the code "CCC," in this example, is associated with air conduit connector 1171 being connected to pressure devices (1202) that are partially or completely blocked or solenoid(s) (1202) that are partially or completely blocked. Moreover, in FIG. 28, an air conduit connector 1181 that has three air conduits or flow tracts 1112 connected to three solenoids 5000 will cause the microprocessor to create a code "AAA." As illustrated in FIG. 28, the code "AAA," in this example, is associated with air conduit connector 1181 being connected to a pressure device having air cells 8000 of a triple cell calf or thigh sleeve.

Figure 29:
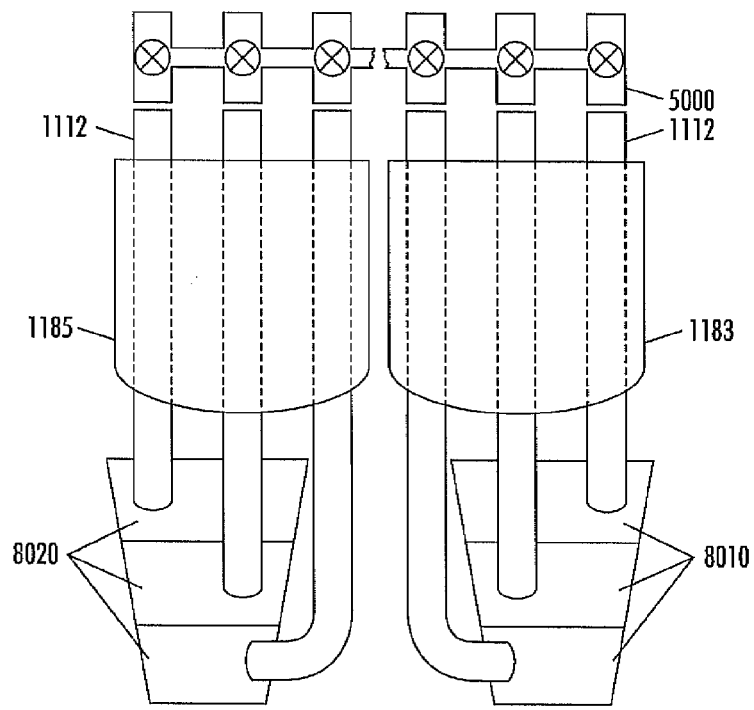

In FIG. 29, an air conduit connector 1185 that has three air conduits or flow tracts 1112 connected to three solenoids 5000 will cause the microprocessor to create a code "AAA." As illustrated in FIG. 29, the code "AAA," in this example, is associated with air conduit connector 1185 being connected to a pressure device having air cells 8020 of a triple cell calf or thigh sleeve. Moreover, in FIG. 29, an air conduit connector 1183 that has three air conduits or flow tracts 1112 connected to three solenoids 5000 will cause the microprocessor to create a code "AAA." As illustrated in FIG. 29, the code "AAA," in this example, is associated with air conduit connector 1183 being connected to a pressure device having air cells 8010 of a triple cell calf or thigh sleeve.

Figure 30:
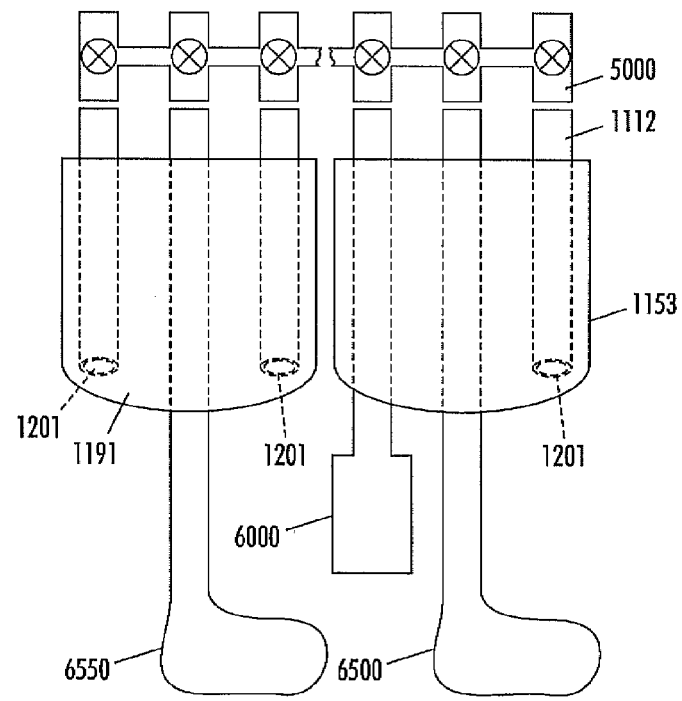

In FIG. 30, an air conduit connector 1191 that has three air conduits or flow tracts 1112 connected to three solenoids 5000 will cause the microprocessor to create a code "BAB." As illustrated in FIG. 30, the code "BAB," in this example, is associated with air conduit connector 1191 being connected to a pressure device having an air cell 6550 of a foot pressure sleeve and no air cells 1201. Moreover, in FIG. 30, an air conduit connector 1153 that has three air conduits or flow tracts 1112 connected to three solenoids 5000 will cause the microprocessor to create a code "AAB." As illustrated in FIG. 30, the code "AAB," in this example, is associated with air conduit connector 1153 being connected to a pressure device having a pressure accumulator 6000, an air cell 6500 of a foot pressure sleeve, and no air cell 1201.

Figure 24:
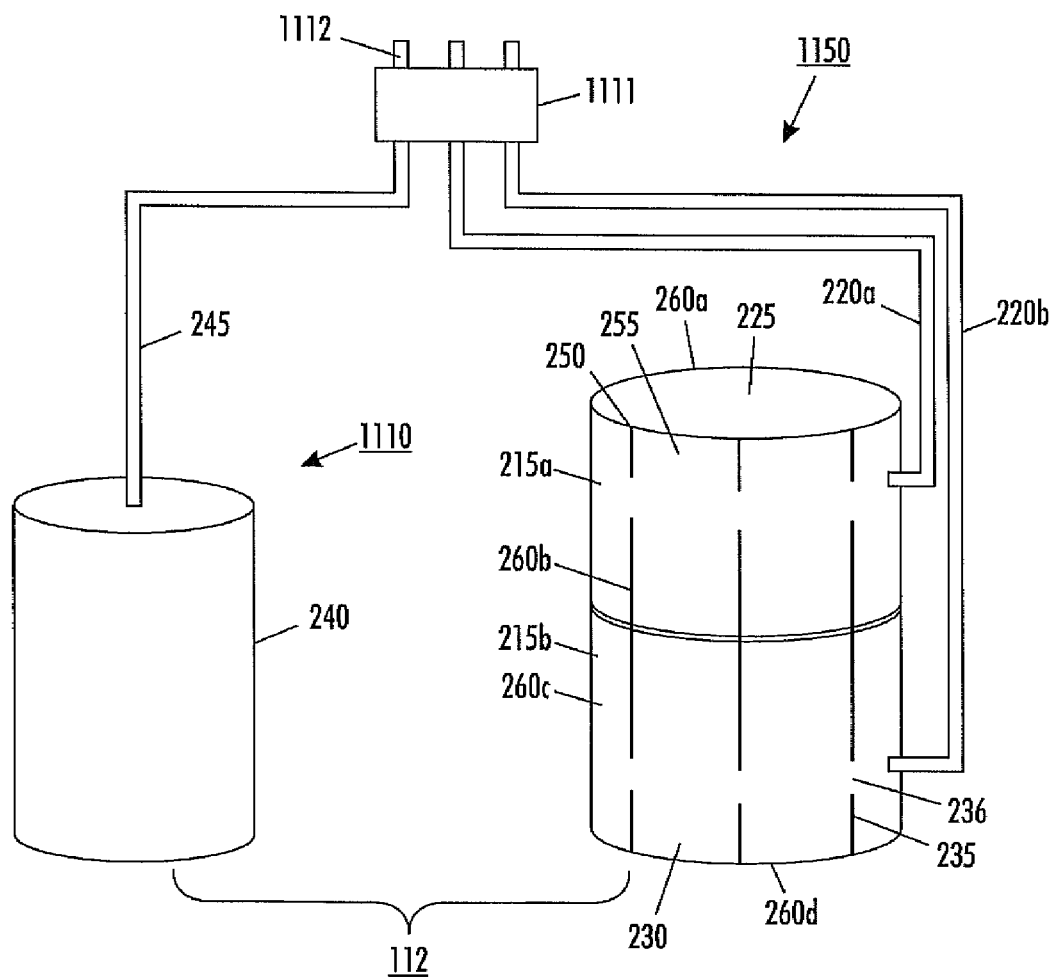
FIG. 24 is another embodiment of a pressure sleeve-pressure accumulator combination according to the concepts of the present invention.

It is noted that the code "A" can be further modified to be "A", "$A_1$", "$A_2$" .... "$A_n$", to provide a more specific identification of the sleeve of combination of sleeves attached to the pump device of the present invention. For example, code "A" could be associated with a foot sleeve wherein $T_1 > T_n > Tmin$. Moreover, code "$A_1$" could be associated with a one cell of a calf sleeve wherein $T_2 > Tn > T_1$. Lastly, code "$A_n$" could be associated with a pressure accumulator wherein $Tmax > Tn > T_{n-1}$. By providing more flexibility with the generation of code "A", the present invention could be enable to operate with an air conduit connector 1111 that has three air conduits or flow tracts 1112, which are connected to a double cell calf sleeve 1150 and a pressure accumulator 1110, as illustrated in FIG. 24.

This "identification system" is very simple to apply and no special hardware changes are necessary. It enables the device to remain an "On-Off" device in spite of its high versatility. It prevents the use of defective sleeves, undesired sleeve combinations, or unauthorized sleeves.

FIGS. 25-30 demonstrate the potential of this "identification system" to differentiate between different pressure devices or different sleeves combinations, in a device that contains six solenoids and pressure devices or sleeves that are connected to the device with an air conduit connector that has three air conduits or flow tracts.

Alternatively the control unit, within the pump unit, can read the input information about the required treatment by reading the coding of the sleeves connectors. While starting any new treatment cycle, the control unit will start the treatment by a quick identification of the type of sleeves connected and will apply the appropriate operating cycle. The coding of the sleeve connectors can be made by state of the art mechanical or electromechanical components wherein each air conduit connector has a mechanical tag, an electronic tag, an optical tag, or an electromechanical tag, all which could be read by the pump unit. This would replace the pressure generation measurement identification process. It is also possible to store the required treatment parameters on the sleeve's connector as part of the mechanical tag, an electronic tag, an optical tag, or an electromechanical tag according to the sleeve's projected treatment.

On start-up of the system, the data will be transferred to the pump unit through either mechanical, electrical, optical means, or a combination thereof, and the treatment cycle will be compatible to the selected sleeve. Moreover, it contemplated that the therapist will be able to program the sleeve's parameters through manipulation of the mechanical tag, the electronic tag, the optical tag, the electromechanical tag, or combination thereof to fit the treatment to the specific patient.

Figure 15:
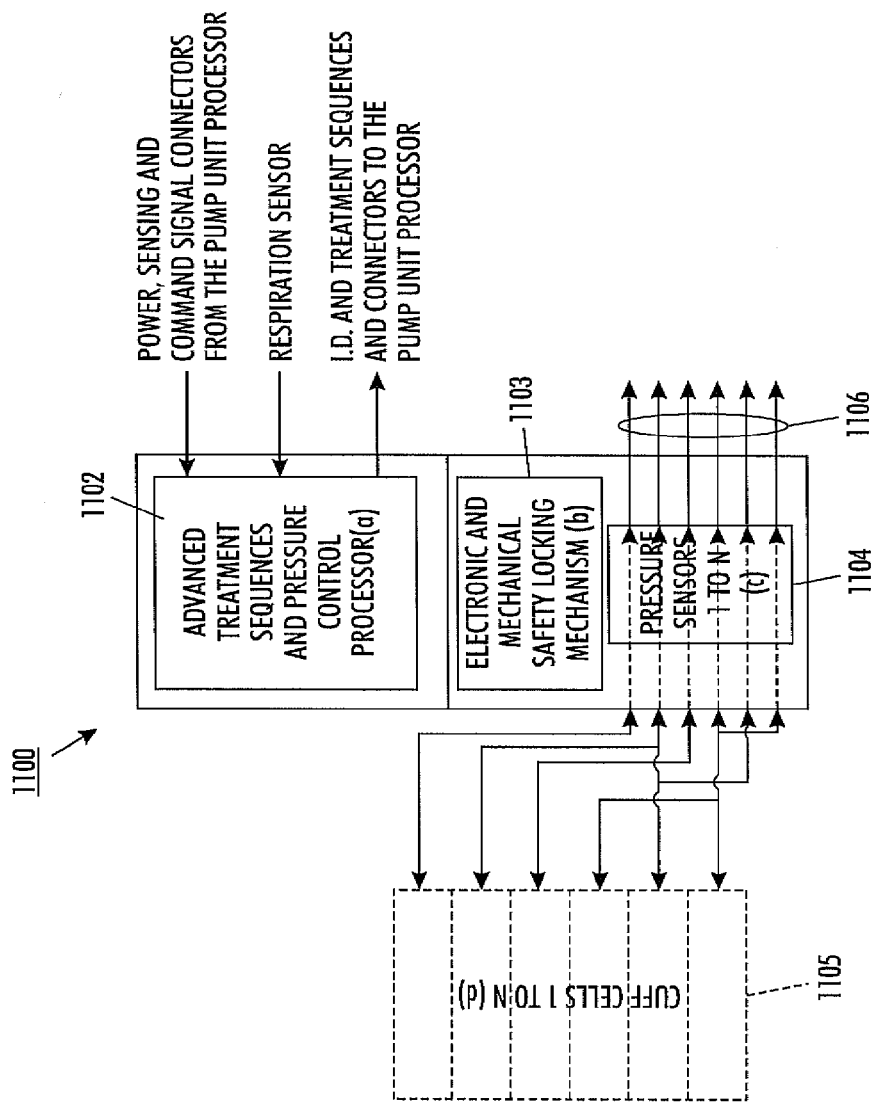
FIG. 15 is a simplified functional block diagram of an exemplary connector assembly according to the concepts of the present invention.

FIG. 15 is a simplified functional block diagram of an exemplary embodiment of a connector assembly 1100 for an associated sleeve 1105 in accordance with the present invention. The assembly 1100 includes an electronic memory and/or control processor unit 1102 that is capable of detecting and transmitting electronic signals. When connected to a pump unit and upon power reset of the pump unit, the processor unit, which can be part of the conduits of the sleeve, receives DC power and sends back an identification signal which initiates the communication procedures. The treatment data will be loaded to the pump unit. The second phase of this operation is to lock the cuff of the sleeve, with an electromechanical safety locking mechanism 1103. This operation is done for safety reasons, to prevent undesired release of the cuff, during normal operation.

Another feature is that a pressure sensors array 1104 measures the pressure at the end of each pressure line 1106. The data collected at this stage is transmitted, via the processor unit 1102, to the processor in the pump unit, in order to evaluate the status of the system. The sleeve 1105 has several cells that can be independently inflated by the pump unit. The number of cells in the sleeve can vary, according to desired treatments.

Figure 16:
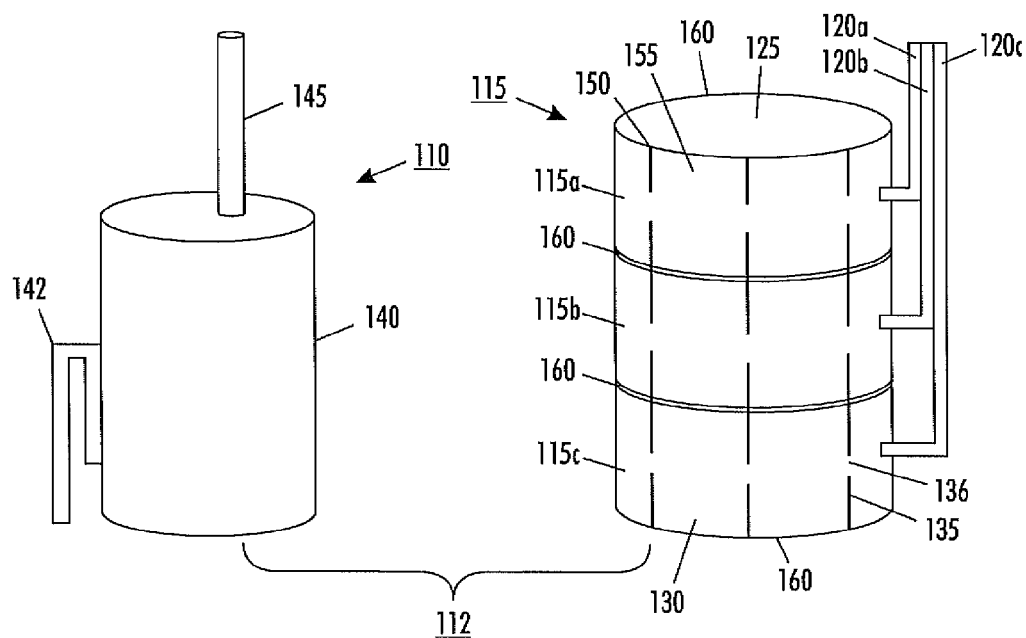
FIG. 16 is one embodiment of a pressure sleeve-pressure accumulator combination according to the concepts of the present invention.

FIG. 16 shows a pressure device having a pressure sleeve-pressure accumulator combination generally indicated by 112 in accordance with another embodiment of the present invention. The combination 112 comprises a pressure sleeve 105 and a pressure accumulator 110. The pressure sleeve 105 may be any known pressure sleeve, but preferably the pressure sleeve is a pressure sleeve with the multiple intra-cell compartments as described above so that a small volume of air or fluid provides for beneficial circumferential constriction of the pressure sleeve upon the limb. The pressure sleeve 105 includes one or more individually inflatable toroidal cells 115.

In FIG. 16, three cells 115a, 115b, and 115c are shown. This is by way of example only, and the pressure sleeve 105 may comprise any number of cells 115. Each cell 115 has an associated tubular conduit 120a, 120b, and 120c. The conduits 120a, 120b, and 120c serve as both an inlet for fluid into the associated cells 115a, 115b, and 115c, respectively, as well as an outlet for fluid out of the associated cell 115a, 115b, and 115c, respectively.

The cells 115a, 115b, and 115c are formed from a flexible, fluid imperious material such as cloth-lined rubber or canvas. The pressure sleeve 105 may be formed for example from an inner cylindrical shell 150 and an outer cylindrical shell 155 formed from a flexible fluid impervious material. Seams 160 at the boundaries of cells 115a, 115b, and 115c are formed by welding the inner cylindrical shell 150 and outer cylindrical shell 155 together at the seams.

The flow of a pressurized fluid through conduits 120a, 120b, and 120c into the associated cell 115a, 115b, and 115c, respectively, inflates the cell so as to exert a pressure on a limb contained in a lumen 125 of the pressure sleeve 105, as explained above. One or more of the cells 115a, 115b, and 115c may optionally be divided into two or more intra-cell compartments 130, as shown, for example, for the cell 115c. The intra-cell compartments 130 are formed by seams 135 extending in a longitudinal direction of the pressure sleeve 105. The seams 135 are incomplete at perforations 136 so that the intra-cell compartments 130 are inflated essentially simultaneously when pressurized fluid enters the cell 115c. As explained above, this decreases the volume of the cell 115c so that a predetermined pressure on a limb positioned in the lumen 125 of the pressure sleeve 105 is realized.

The pressure accumulator 110 comprises a container 140 formed from a fluid impervious material. The container 140 may be made from a flexible material such as cloth-lined rubber or canvas. Alternatively, the container 140 may be made from a rigid material such as plastic or metal. The accumulator 110 further comprises a tubular conduit 145 that serves both as an inlet for pressurized fluid into the container 140 as well as an outlet for fluid out of the container 140.

The pressure accumulator 110 enables the compression system to provide intermittent pneumatic compression, fast intermittent pneumatic compression, fast inflation, less complexity, lower costs, and greater patient comfort. Moreover, the pressure accumulator 110 enables the compression system to provide effective therapeutic venous flow acceleration.

It is noted, according to the concepts of the present invention, that the pressure accumulator 110, as illustrated in the embodiment of FIG. 16, is not part of a console. In this embodiment of the present invention, the pressure accumulator 110 is a device that is separate, e.g., non-integral, from the other components of the compression system. The pressure accumulator 110 can then be located at any convenient location that the user desires. As illustrated in FIG. 16, the pressure accumulator 110 includes a clip or fastening device 142 that enables the pressure accumulator 110 to be located on the belt of the user or hook onto another proximately located object. This fastening device 142 may also include a strap to fasten around the waist or limb of the user. Thus, the pressure accumulator 110 is flexibly tethered to the compression system of the present invention to provide mobility and flexibility.

Figure 17:
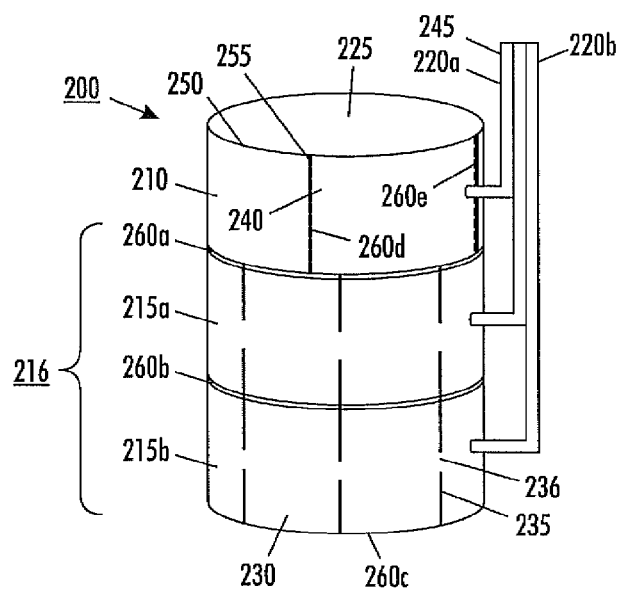
FIG. 17 shows another embodiment of pressure sleeve-pressure accumulator combination in which the accumulator is integral with the sleeve according to the concepts of the present invention.

FIG. 17 shows a pressure device having a pressure sleeve-pressure accumulator combination generally indicated by 200 in accordance with a further embodiment of the present invention. In this embodiment a pressure accumulator 210 is integrated into a pressure sleeve 205, thereby making the pressure accumulator 210 integral with the pressure sleeve 205. As illustrated in FIG. 16, the pressure sleeve 205 is divided into the pressure accumulator 210 and a pressure application section 216 made up of cells 215a and 215b.

This is by way of example only, and the pressure sleeve 205 may comprise any number of cells. As with the sleeve shown in FIG. 16, each cell has an associated tubular conduit (220a and 220b) that serves as both a fluid inlet and outlet for the cell. The cells are formed from a flexible, fluid impervious material such as cloth-lined rubber or canvas. One or more of the cells may be divided into intra-cell compartments 230, as explained above with reference to FIG. 16, having seams 235 and perforations 236 so that the intra-cell compartments are inflated essentially simultaneously when pressurized fluid enters the cell.

The pressure accumulator 210 comprises a container 240 formed from a fluid impervious material. The accumulator 210 further comprises a tubular conduit 245 that serves both as an inlet for pressurized fluid into the container 240 as well as an outlet for fluid out of the container 240. The outside part of the container 240 may be made from a flexible material such as cloth-lined rubber or canvas; however, the inside part of the container 240 should be made from a rigid material, such as a hard plastic or metal, to prevent any pressure from the pressure accumulator from being incorrectly transmitted to the patient. Alternatively, the entire container 240 may be made from a rigid material, such as a hard plastic or metal. The container 240 may partially surround the lumen 225 of the pressure sleeve 205 as shown in FIG. 17. Alternatively, the container 240 may completely surround the lumen 225 of the pressure sleeve 205 (not shown).

In a preferred embodiment, the pressure sleeve 205 is formed from an inner cylindrical shell 250 and an outer cylindrical shell 255 formed from a flexible fluid impervious material. Seams (260a, 260b, 260c, 260d, and 260e) at the boundaries of the cells, at the boundaries of the container 240 or at the boundary between the container 240 and the cell 215a are formed by welding the inner and outer sleeves together at the seams.

FIG. 24 shows a pressure device having a pressure sleeve-pressure accumulator combination generally indicated by 1120 in accordance with a further embodiment of the present invention. In this embodiment a pressure accumulator 1110 is separate from a pressure sleeve 1150. As illustrated in FIG. 24, the pressure sleeve 1150 is divided into pressure application cells 215a and 215b.

This is by way of example only, and the pressure sleeve 1150 may comprise any number of cells. As with the sleeve shown in FIG. 17, each cell has an associated tubular conduit (220a and 220b) that serves as both a fluid inlet and outlet for the cell. The cells (215a and 215b) are formed from a flexible, fluid impervious material such as cloth-lined rubber or canvas. One or more of the cells may be divided into intra-cell compartments 230, as explained above with reference to FIG. 17, having seams 235 and perforations 236 so that the intra-cell compartments are inflated essentially simultaneously when pressurized fluid enters the cell.

The pressure accumulator 1110 comprises a container 240 formed from a fluid impervious material. The accumulator 210 further comprises a tubular conduit 245 that serves both as an inlet for pressurized fluid into the container 240 as well as an outlet for fluid out of the container 240. The container 240 may be made from a flexible material such as cloth-lined rubber or canvas. Alternatively, the container 240 may be made from a rigid material such as plastic or metal.

In a preferred embodiment, the pressure sleeve 1150 is formed from an inner cylindrical shell 250 and an outer cylindrical shell 255 formed from a flexible fluid impervious material. Seams (260a, 260b, 260c, and 260d) at the boundaries of the cells are formed by welding the inner and outer sleeves together at the seams.

As noted above, the pressure sleeve-pressure accumulator combination 1120 is connected via tubular conduit (220a, 220b, and 245) to air conduit connector 1111 that has three air conduits or flow tracts 1112.

Figure 18:
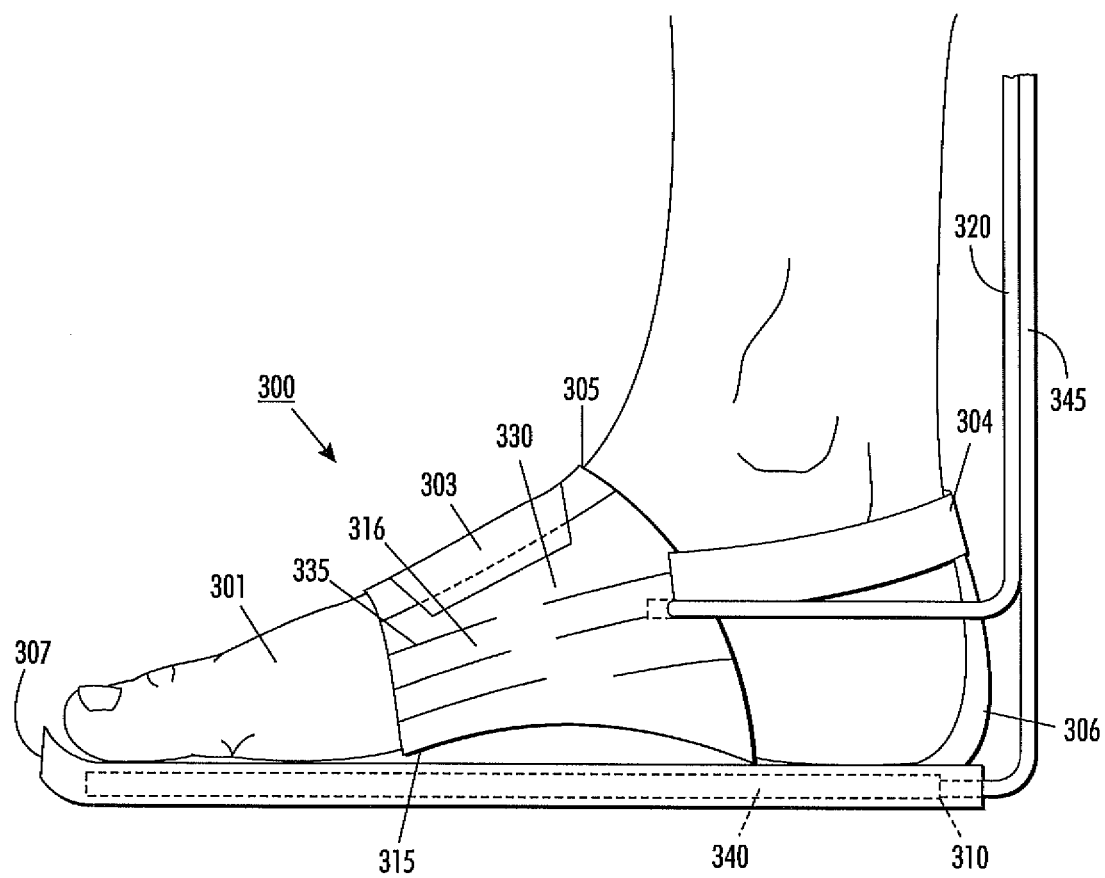
FIG. 18 shows a third embodiment of a pressure sleeve-pressure accumulator combination in the form of a slipper according to the concepts of the present invention.

FIG. 18 shows a pressure device having a pressure sleeve-pressure accumulator combination generally indicated by 300 in accordance with another embodiment of the present invention. In this embodiment, the combination 300 is formed into a slipper 307 to be worn on a foot 301. The combination 300 comprises a pressure sleeve 305 that comprises one cell 315. This is by way of example only, and the pressure sleeve 305 may comprise any number of cells. The cell or cells 315 may be divided into intra-cell compartments 330, as discussed above in reference to FIG. 16, having seams 335 and perforations 336 so that the intra-cell compartments are inflated essentially simultaneously when pressurized fluid enters the cell. The cell 315 has an associated tubular conduit 320.

The combination 300 further comprises a pressure accumulator 310. The pressure accumulator 310 has been incorporated into the sole of the slipper 307. The pressure accumulator 310 comprises a container 340 formed from a fluid impervious material that is sufficiently flexible so as to allow it to bend for comfortable walking while being sufficiently rigid so that it does not collapse under the weight of the user. The container 340 may be formed, for example, from reinforced rubber. The pressure accumulator 310 further comprises a tubular conduit 345 that serves both as an inlet for pressurized fluid into the container 340 as well as an outlet for fluid out of the container 340.

The combination 300 lastly comprises a foot fastener 303 that causes the pressure sleeve 305 to be snug around the foot 301. This foot fastener 303 may be a Velcro™ strap or other device that enables the pressure sleeve 305 to be formed around the foot 301. An ankle strap 304 is provided to prevent the pressure sleeve 305 and slipper 307 from shifting or coming disengaged from the foot 301. The ankle strap 306 may be a Velcro™ strap or other device that prevents the pressure sleeve 305 and slipper 307 from shifting or coming disengaged from the foot 301. The ankle strap 304 is provided with a heel support 306 that prevents the foot from sliding out of the back of the slipper 304. The heel support 306 may be of a rigid material, such as a plastic, or a flexible material, such as cloth.

Figure 31:
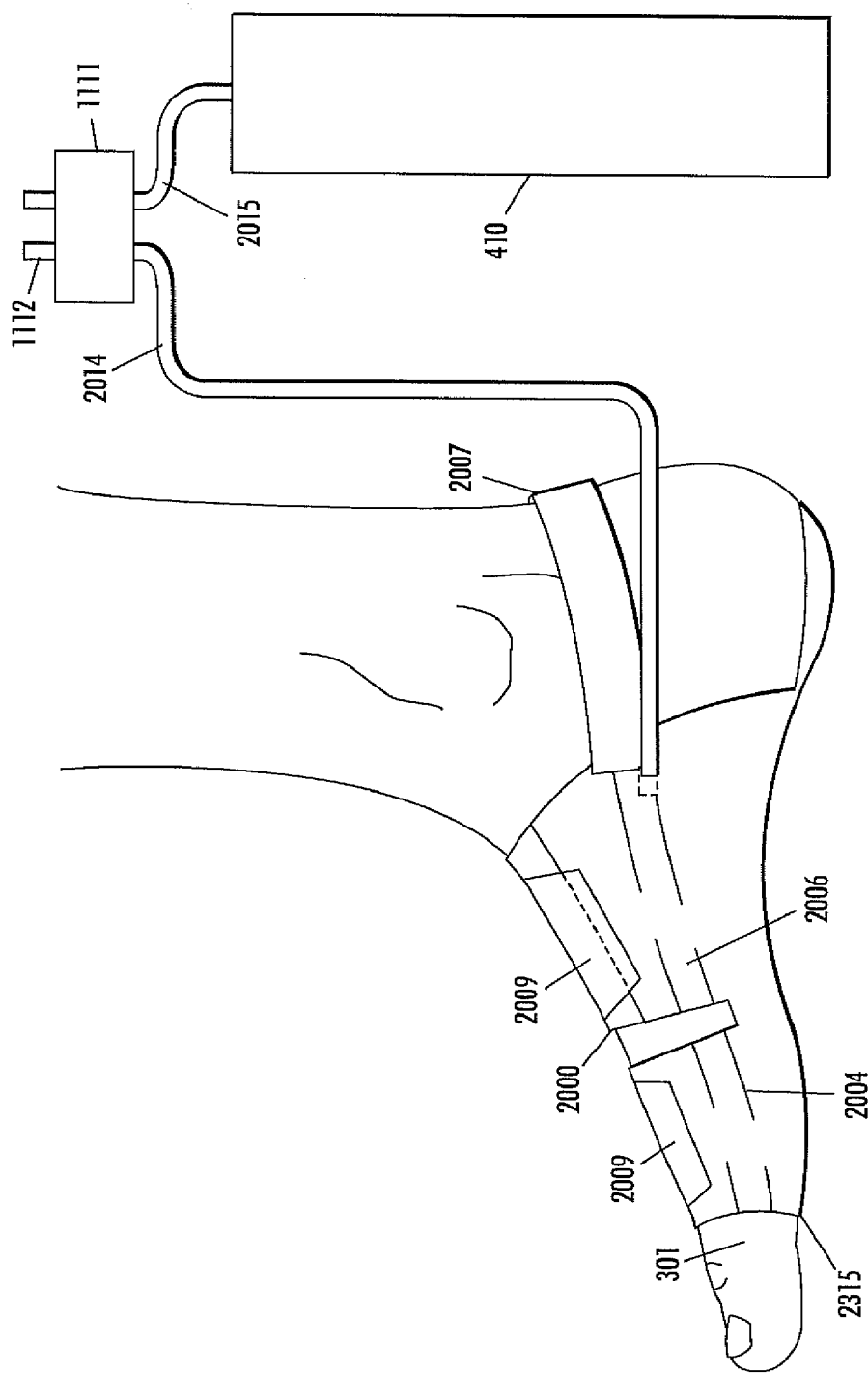
FIG. 31 shows an embodiment of a foot pressure sleeve-pressure accumulator according to the concepts of the present invention.

FIG. 31 shows another pressure device having a pressure sleeve-pressure accumulator combination in accordance with another embodiment of the present invention. In this embodiment, the combination comprises a pressure sleeve 2000 that comprises one cell 2315. This is by way of example only, and the pressure sleeve 2000 may comprise any number of cells. The cell or cells 2315 may be divided into intra-cell compartments 2006, as discussed above in reference to FIG. 16, having seams 2004 and perforations so that the intra-cell compartments are inflated essentially simultaneously when pressurized fluid enters the cell. The cell 2315 has an associated tubular conduit 2014.

The pressure sleeve-pressure accumulator combination further comprises a pressure accumulator 410. The pressure accumulator 410 is separate from the pressure sleeve 2000. The pressure accumulator 410 comprises a container formed from a fluid impervious material. The container may be formed, for example, from a flexible material such as cloth-lined rubber or canvas or from a rigid material such as plastic or metal. The pressure accumulator 410 further comprises a tubular conduit 2015 that serves both as an inlet for pressurized fluid into the container as well as an outlet for fluid out of the container.

The combination lastly comprises foot fasteners 2009 that cause the pressure sleeve 2000 to be snug around the foot 301. The foot fasteners 2009 may be Velcro™ straps or other devices that enable the pressure sleeve 2000 to be formed around the foot 301. An ankle strap 2007 is provided to prevent the pressure sleeve 2000 from shifting or coming disengaged from the foot 301. The ankle strap 2007 may be a Velcro™ strap or other device that prevents the pressure sleeve 2000 from shifting or coming disengaged from the foot 301.

Figure 22:
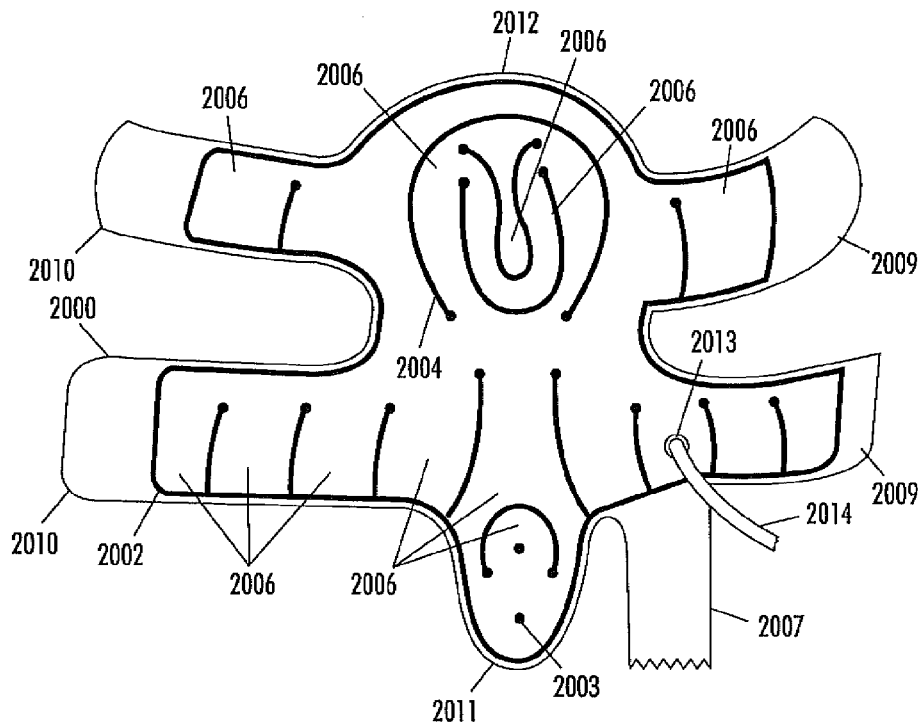
FIG. 22 shows an embodiment of a foot pressure sleeve according to the concepts of the present invention.

A more detail illustration of the pressure sleeve of FIG. 31 is shown in FIG. 22. As illustrated in FIG. 22, a foot pressure sleeve 2000 is constructed from two shells that have been welded together. The shells are a fluid impervious and flexible material such as cloth-lined rubber or canvas. The foot pressure sleeve 2000 contains a cell formed by weld 2002. This is by way of example only, and the pressure sleeve 2000 may comprise any number of cells. The cell or cells contain multiple intra-cells 2006 formed by intra-cell linear-welds 2004 and intra-cell spot-welds 2003. The foot pressure sleeve 2000 has a forward section 2012 that can extend from an arch portion of a patient's foot to under either the ball of a patient's foot or the toes of a patient's foot. The foot pressure sleeve 2000 also has a rearward section 2011 that substantially extends under the heel of a patient's foot. The cell has an associated tubular conduit 2014.

The foot pressure sleeve 2000 comprises foot fasteners 2009 and 2010 that causes the pressure sleeve 2000 to be snug around the foot. The foot fasteners 2009 and 2010 may be Velcro™ straps or other devices that enable the pressure sleeve 2000 to be formed around the foot. An ankle strap 2007 is provided to prevent the pressure sleeve 2000 from shifting or coming disengaged from the foot. The ankle strap 2007 may be a Velcro™ strap or other device that prevents the pressure sleeve 2000 from shifting or coming disengaged from the foot.

Figure 41:
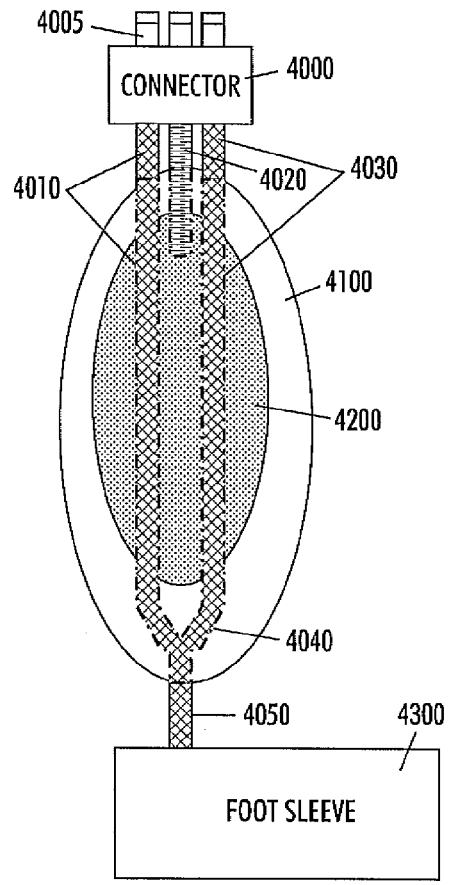
FIG. 41 illustrates a pressure sleeve and pressure accumulator combination according to the concepts of the present invention.
Figure 42:
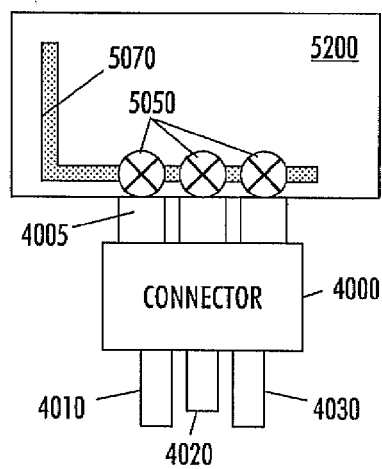
FIG. 42 illustrates a coupling of a pressure sleeve and pressure accumulator combination to a console housing a compressor.

FIG. 41 shows another pressure device having a pressure sleeve-pressure accumulator combination (pressure device) in accordance with another embodiment of the present invention. In this embodiment, the pressure device comprises a foot pressure sleeve 4300. In this example, the foot pressure sleeve 4300 comprises a single cell; however the foot pressure sleeve 4300 may comprise any number of cells. The foot pressure sleeve 4300 has an associated tubular conduit 4010, 4030, 4040, and 4050 connected to the connector 4000. The connector 4000 includes coupler 4005 to connect to valves 5050 that are connected to conduit 5070, as illustrated in FIG. 42.

The pressure device further comprises a pressure accumulator 4200 that is located in a pressure accumulator flexible housing 4100. The pressure accumulator 4200 is separate from the foot pressure sleeve 4300. The pressure accumulator 4200 comprises a container formed from a fluid impervious material. The container may be formed, for example, from a flexible material such as cloth-lined rubber or canvas or from a rigid material such as plastic or metal. The pressure accumulator 4200 further comprises a tubular conduit 4020 that serves both as an inlet for pressurized fluid into the container as well as an outlet for fluid out of the container.

Lastly, as illustrated in FIG. 41, the conduits 4010 and 4030 may be housed in or pass through the pressure accumulator flexible housing 4100. Moreover, if the foot pressure sleeve 4300 contains a single cell, the conduits 4010 and 4030 may be connected together by a y-joint 4040 within the pressure accumulator flexible housing 4100, with the y-joint 4040 being connected to conduit 4050 leading to the foot pressure sleeve 4300.

Figure 32:
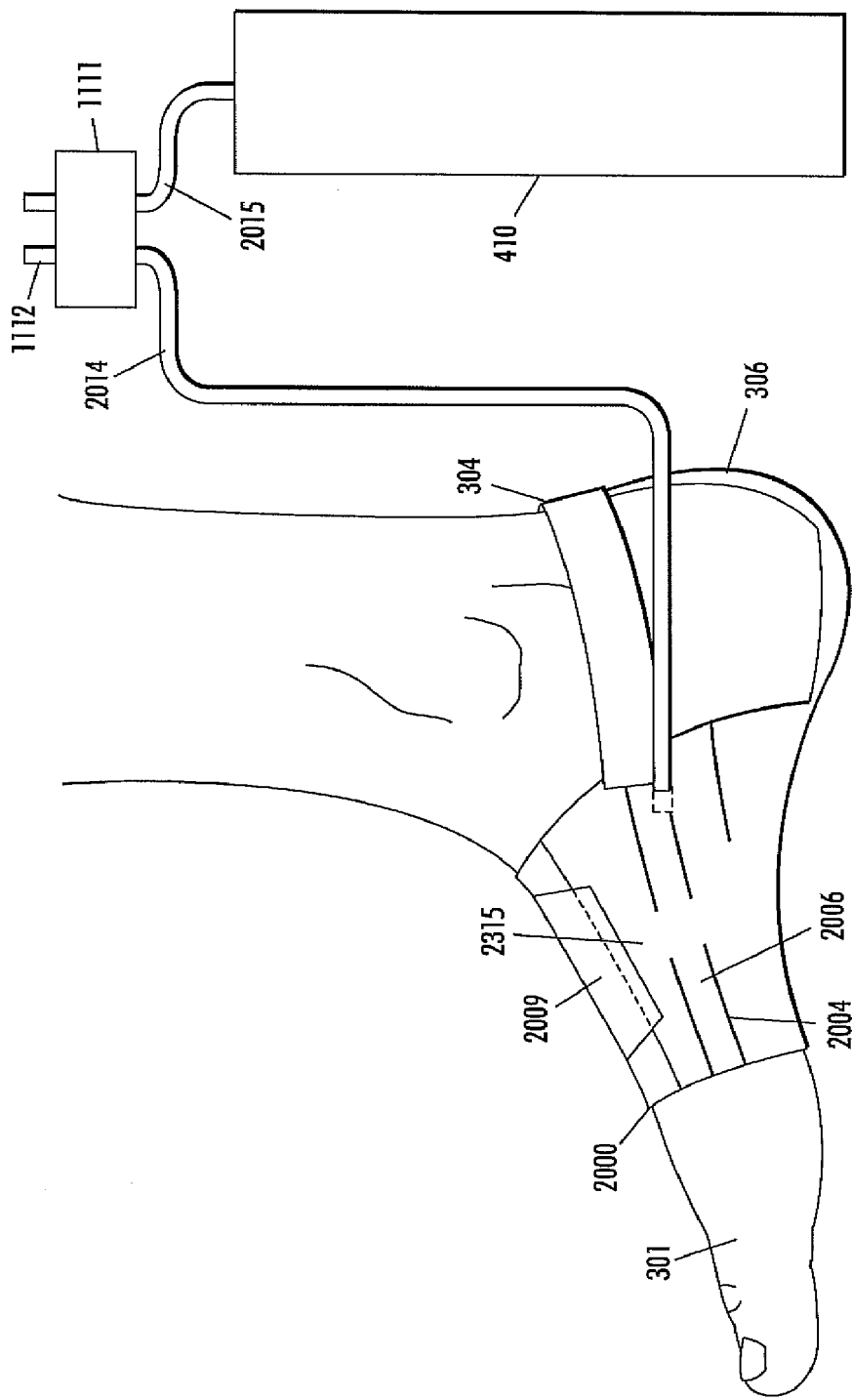
FIG. 32 shows another embodiment of a foot pressure sleeve-pressure accumulator according to the concepts of the present invention.

FIG. 32 shows another pressure device having a pressure sleeve-pressure accumulator combination in accordance with another embodiment of the present invention. In this embodiment, the combination comprises a pressure sleeve 2000 that comprises one cell 2315. This is by way of example only, and the pressure sleeve 2000 may comprise any number of cells. The cell or cells 2315 may be divided into intra-cell compartments 2006, as discussed above in reference to FIG. 16, having seams 2004 and perforations so that the intra-cell compartments are inflated essentially simultaneously when pressurized fluid enters the cell. The cell has an associated tubular conduit 2014 connected through port 2013.

The pressure sleeve-pressure accumulator combination further comprises a pressure accumulator 410. The pressure accumulator 410 is separate from the pressure sleeve 2000. The pressure accumulator 410 comprises a container formed from a fluid impervious material. The container may be formed, for example, from a flexible material such as cloth-lined rubber or canvas or from a rigid material such as plastic or metal. The pressure accumulator 410 further comprises a tubular conduit 2015 that serves both as an inlet for pressurized fluid into the container as well as an outlet for fluid out of the container.

The combination lastly comprises a foot fastener 2009 that causes the pressure sleeve 2000 to be snug around the foot 301. The foot fastener 2009 may be a Velcro™ strap or another device that enables the pressure sleeve 2000 to be formed around the foot 301. An ankle strap comprising an ankle portion 304 and a heel portion 306 is provided to prevent the pressure sleeve 2000 from shifting or coming disengaged from the foot 301. The ankle strap comprising ankle portion 304 and heel portion 306 may include a Velcro™ strap or other device that prevents the pressure sleeve 2000 from shifting or coming disengaged from the foot 301.

Figure 23:
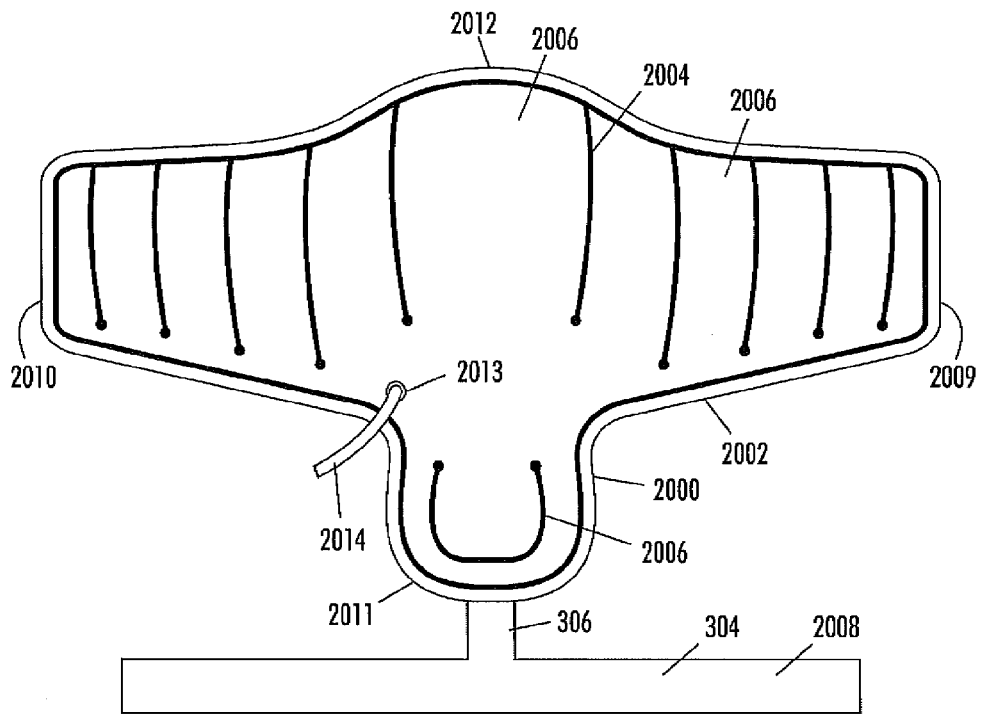
FIG. 23 shows another embodiment of a foot pressure sleeve according to the concepts of the present invention.

A more detail illustration of the pressure sleeve of FIG. 32 is shown in FIG. 23. As illustrated in FIG. 23, a foot pressure sleeve 2000 is constructed from two shells that have been welded together. The shells are a fluid impervious and flexible material such as cloth-lined rubber or canvas. The foot pressure sleeve 2000 contains a cell formed by weld 2002. This is by way of example only, and the pressure sleeve 2000 may comprise any number of cells. The cell or cells contain multiple intra-cells 2006 formed by intra-cell linear-welds 2004 and intra-cell spot-welds 2003. The foot pressure sleeve 2000 has a forward section 2012 that can extend from an arch portion of a patient's foot to the ball of a patient's foot. The foot pressure sleeve 2000 also has a rearward section 2011 that substantially extends under the heel of a patient's foot. The cell has an associated tubular conduit 2014 connected through port 2013.

The foot pressure sleeve 2000 comprises foot fasteners 2009 and 2010 that causes the pressure sleeve 2000 to be snug around the foot. The foot fasteners 2009 and 2010 may be Velcro™ straps or other devices that enable the pressure sleeve 2000 to be formed around the foot. An ankle strap 2008 comprising an ankle portion 304 and a heel portion 306 is provided to prevent the pressure sleeve 2000 from shifting or coming disengaged from the foot. The ankle strap 2008 comprising an ankle portion 304 and a heel portion 306 may include a Velcro™ strap or other device that prevents the pressure sleeve 2000 from shifting or coming disengaged from the foot.

Figures 33, 34:
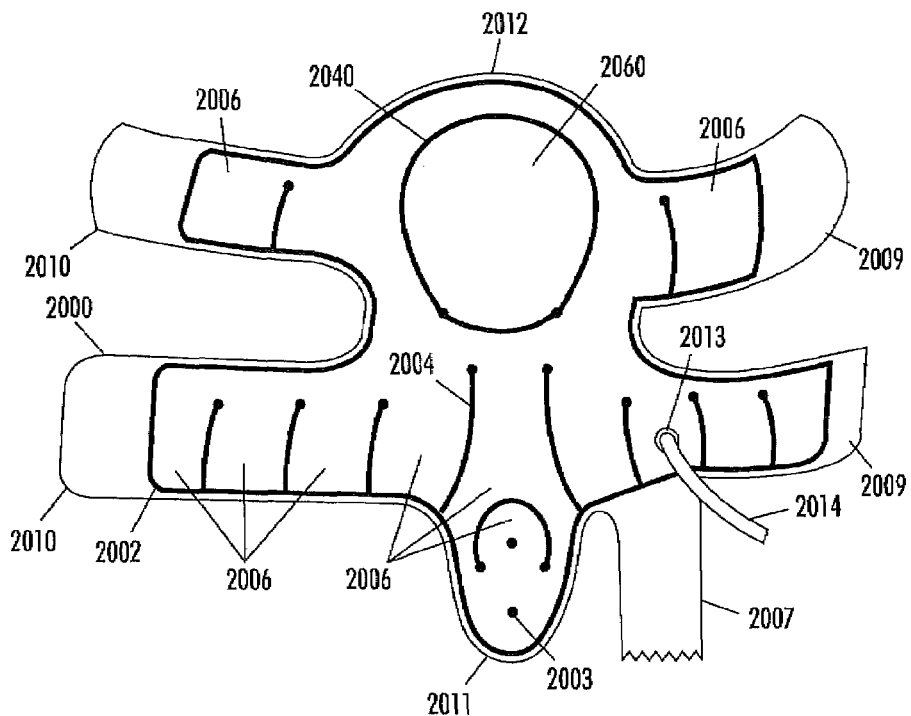
FIGS. 33 and 34 show further embodiments of a foot pressure sleeve according to the concepts of the present invention.

FIG. 33 shows another example of a pressure device having a foot pressure sleeve according to the concepts of the present invention. As illustrated in FIG. 33, a foot pressure sleeve 2000 is constructed from two shells that have been welded together. The shells are a fluid impervious and flexible material such as cloth-lined rubber or canvas. The foot pressure sleeve 2000 contains a cell formed by weld 2002. This is by way of example only, and the pressure sleeve 2000 may comprise any number of cells. The cell or cells contain multiple intra-cells 2006 formed by intra-cell linear-welds 2004 and intra-cell spot-welds 2003.

The foot pressure sleeve 2000 has a forward section 2012 that can extend from an arch portion of a patient's foot to under either the ball of a patient's foot or the toes of a patient's foot. The forward section 2012, as illustrated in FIG. 33, includes a weld 2040 that is used to form a non-inflating section 2060. The non-inflating section 2060 is formed substantially from an arch portion of a patient's foot to under either the ball of a patient's foot or the toes of a patient's foot so that no significant pressure is applied to a bottom portion of the patients' foot associated with the non-inflating section 2060.

The foot pressure sleeve 2000 also has a rearward section 2011 that substantially extends under the heel of a patient's foot. The cell has an associated tubular conduit 2014.

The foot pressure sleeve 2000 comprises foot fasteners 2009 and 2010 that causes the pressure sleeve 2000 to be snug around the foot. The foot fasteners 2009 and 2010 may be Velcro™ straps or other devices that enable the pressure sleeve 2000 to be formed around the foot. An ankle strap 2007 is provided to prevent the pressure sleeve 2000 from shifting or coming disengaged from the foot. The ankle strap 2007 may be a Velcro™ strap or other device that prevents the pressure sleeve 2000 from shifting or coming disengaged from the foot.

FIG. 34 shows a further example of a pressure device having a foot pressure sleeve according to the concepts of the present invention. As illustrated in FIG. 34, a foot pressure sleeve 2000 is constructed from two shells that have been welded together. The shells are a fluid impervious and flexible material such as cloth-lined rubber or canvas. The foot pressure sleeve 2000 contains a cell formed by weld 2002. This is by way of example only, and the pressure sleeve 2000 may comprise any number of cells. The cell or cells contain multiple intra-cells 2006 formed by intra-cell linear-welds 2004 and intra-cell spot-welds 2003.

The foot pressure sleeve 2000 has a forward section 2012 that can extend from an arch portion of a patient's foot to under the ball of a patient's foot. The forward section 2012, as illustrated in FIG. 34, includes a weld 2040 that is used to form a non-inflating section 2060. The non-inflating section 2060 is formed substantially from an arch portion of a patient's foot to under the ball of a patient's foot so that no significant pressure is applied to a bottom portion of the patients' foot associated with the non-inflating section 2060.

The foot pressure sleeve 2000 also has a rearward section 2011 that substantially extends under the heel of a patient's foot. The cell has an associated tubular conduit 2014 connected through port 2013.

The foot pressure sleeve 2000 comprises foot fasteners 2009 and 2010 that causes the pressure sleeve 2000 to be snug around the foot. The foot fasteners 2009 and 2010 may be Velcro™ straps or other devices that enable the pressure sleeve 2000 to be formed around the foot. An ankle strap 2008 comprising an ankle portion 304 and a heel portion 306 is provided to prevent the pressure sleeve 2000 from shifting or coming disengaged from the foot. The ankle strap 2008 comprising an ankle portion 304 and a heel portion 306 may include a Velcro™ strap or other device that prevents the pressure sleeve 2000 from shifting or coming disengaged from the foot.

Figure 19:
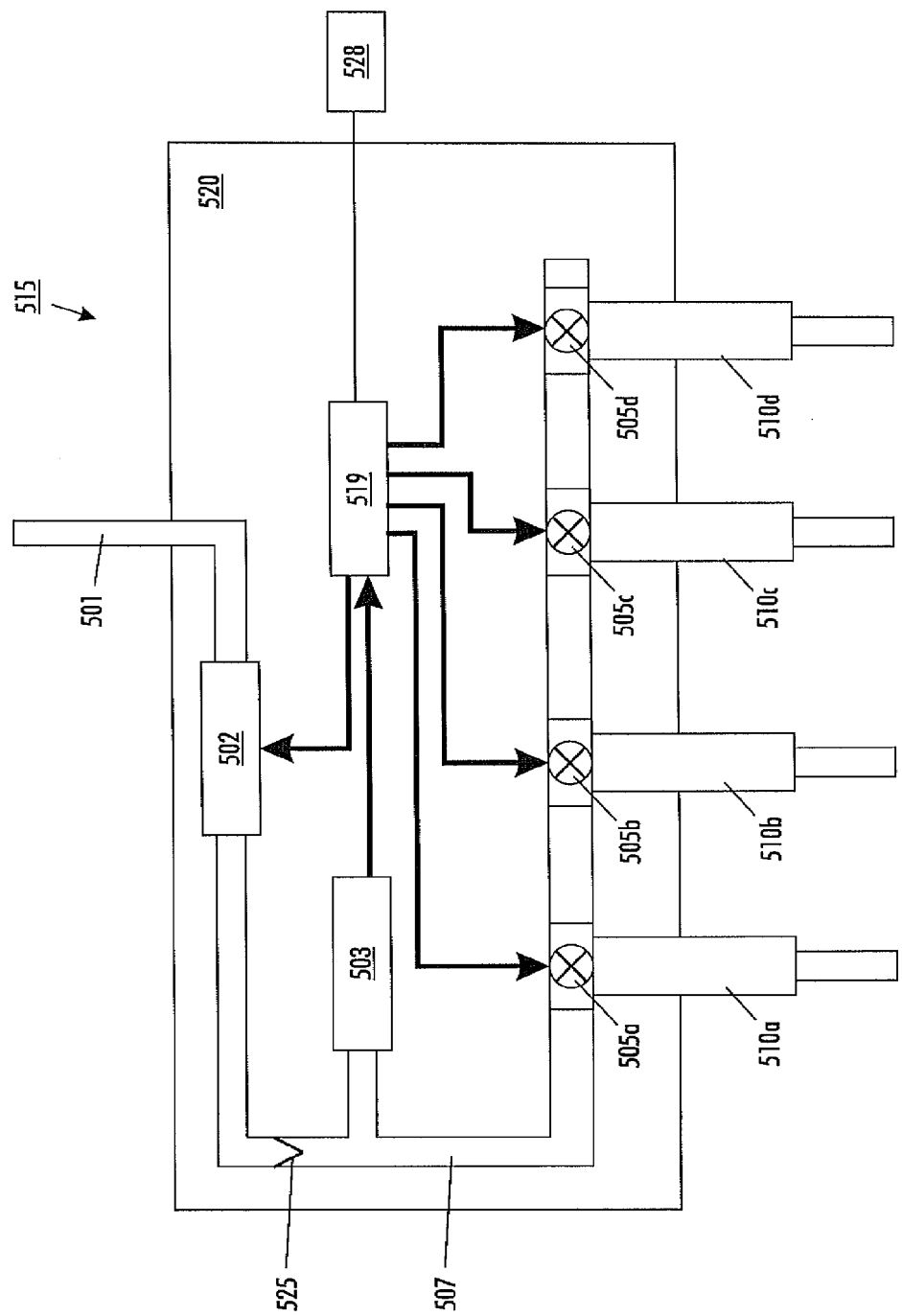
FIG. 19 shows a system for applying pressure to a body limb according to the concepts of the present invention.
Figure 20:
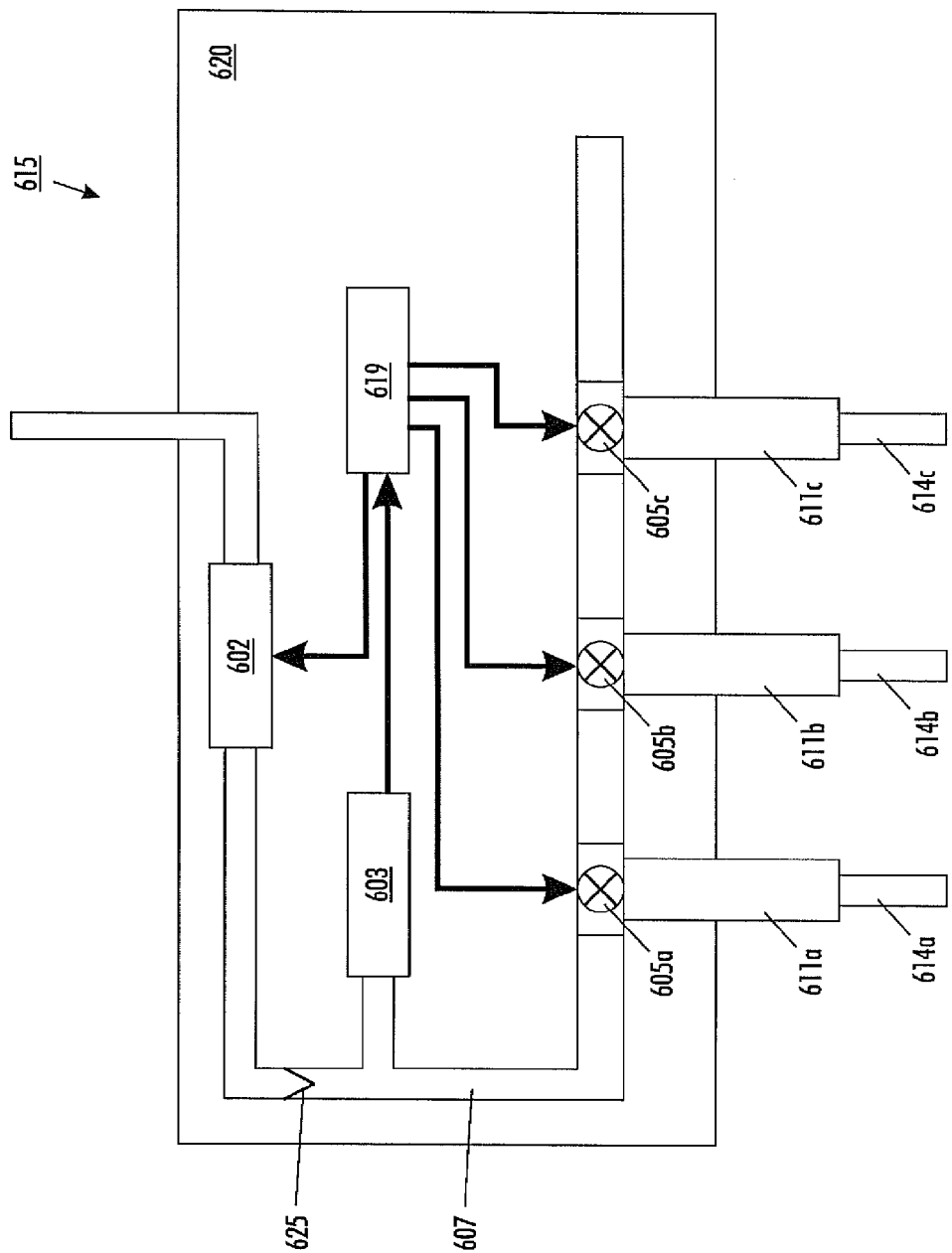
FIG. 20 shows a prior art system not having a pressure accumulator for applying pressure to a body limb.
Figure 21:
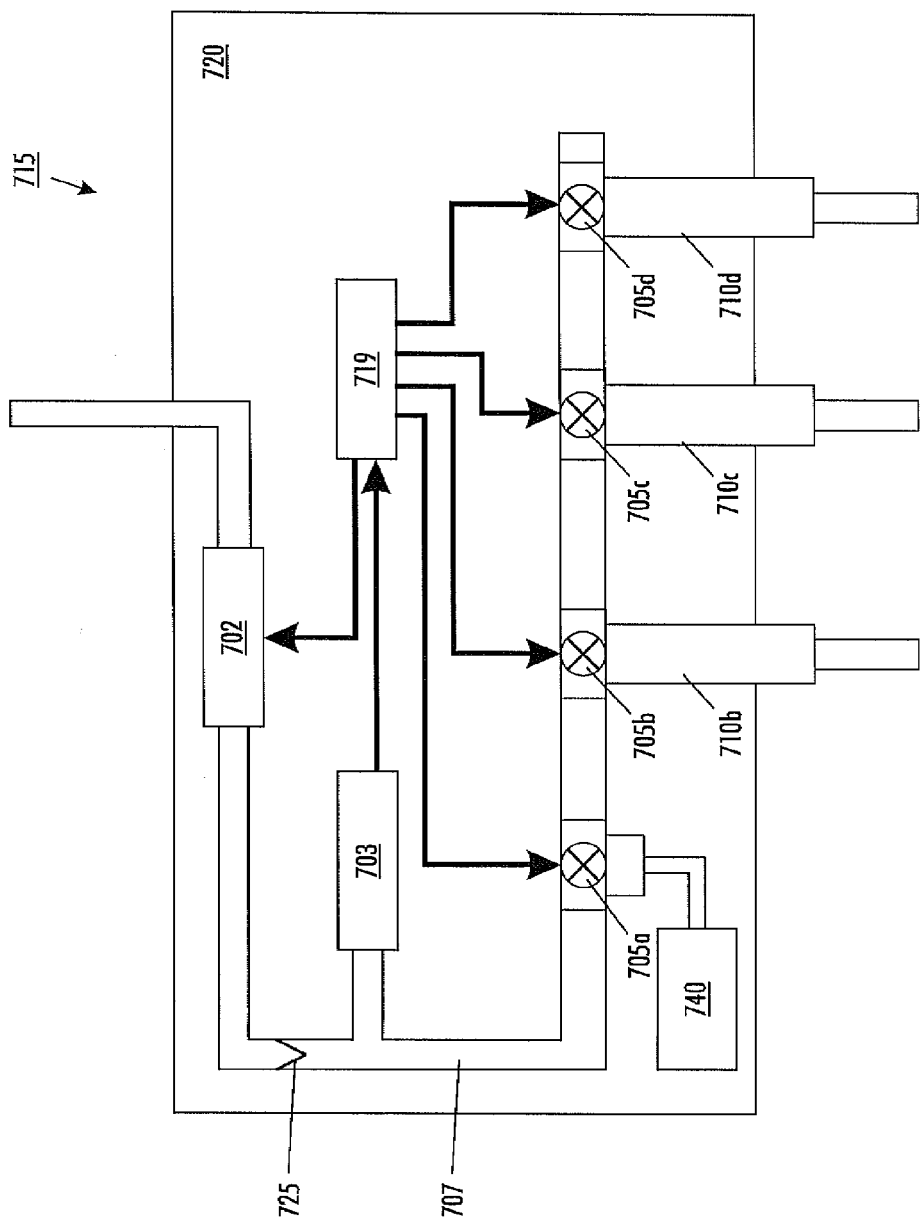
FIG. 21 shows a prior art system having a pressure accumulator located inside the housing of a console for applying pressure to a body limb.

FIG. 19 shows a console system generally indicated by 515 for enabling the application of pressure to a body limb. The system 515, as illustrated in FIG. 19, can be utilized in conjunction with the pressure sleeve-pressure accumulator combination 112 described above in reference to FIG. 16.

The pressure sleeve used in conjunction with the console 515 preferably contains one or more cells divided into longitudinally extending compartments that are inflated and deflated essentially simultaneously. The console 515 is preferably portable and battery operated and includes an air compressor 502.

It is noted that air compressor 502 may be bypassed with pressurized air from an external source. The pressurized air would be introduced into the console 515 through pressurized air inlet 501.

The console 515 is also preferably configured to be carried on a user's body. For example, the console 515 may have clips (not shown) that allow the console 515 to be attached to the user's belt.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

As further illustrated in FIG. 19, the control unit 519 is attached to a sensor 528. The sensor 528 monitors the respiration cycle and provides signals to the control unit 515. The sensor 528 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. Moreover, the sensor 528 may be an autonomic air pletismographic device which utilizes the employment of a pneumatic cuff that encircles a segment of the body part being examined. In a preferred embodiment, this pneumatic cuff may encircle the patient's calf. An increase or decrease in the volume of the body part being examined will produce a similar change in the pressure of the captive air (the captive air being the air within the pneumatic cuff, and this pressure change can be recorded with a suitable transducer. As noted above, the monitoring of the respiration cycle is only one example of monitoring the venous phasic flow of the patient. The sensor 528 may be any sensor that is capable of providing data relative to the venous phasic flow.

Moreover, FIG. 19 illustrates that the sensor 528 is directly connected to the control unit 515; however, it is noted that the sensor 528 can also provide the data to the control unit 515 through a radio signal or similar means of communication, thus the sensor 528 need not be physically connected to the control unit 515, only in communication therewith.

Upon receiving this data, the control unit 515 controls the operations so that external pressure/compression generated venous flow is in-phase with the natural venous phasic flow. In the example of FIG. 19, the realization of the external pressure/compression generated venous flow being in-phase with the natural venous phasic flow is the external pressure/compression generated venous flow being in-phase with an expiration phase or periods of low intra-abdominal pressure.

The console system shown in FIG. 19 is used when it is desired to apply pressure rapidly to a portion of a body limb. In this application, the valve 505a is opened while the valves 505b, 505c, and 505d are closed, causing pressurized air to flow in the conduit 507 from the compressor 502 through the valve 505a into the tubular conduit 510a associated with a pressure accumulator, such as pressure accumulator 110 of FIG. 16. When the pressure in the pressure accumulator reaches a predetermined value $P_A$, as determined by the pressure gauge 503, the processor 519 opens the valve 505b causing air to flow from the associated pressure accumulator into the cell, such as cell 115a of FIG. 16.

The flow of air in the conduit 507 from the pressure accumulator towards the compressor 502 is prevented by the one-way valve 525. The pressure in the cell will rise rapidly to a pressure $P_c$. $P_A$ and $P_c$ satisfy the relationship $P_A V_A = P_C(V_A + V_C)$ where $V_A$ is the volume of the container of the pressure accumulator and $V_C$ is the volume of the cell when inflated. Next, another cell, such as cell 115b of FIG. 16, may be inflated by opening the valve 505c. A next cell, such as cell 115c of FIG. 16, is inflated by opening the valve 505d. The cells are then deflated and the cycle can begin again.

FIGS. 37-40 illustrate the operation of the present invention when a console, as illustrated in FIG. 19, is connected to a pressure device, such as the pressure sleeve and pressure accumulator of FIGS. 41 and 42 as described above.

Figure 37:
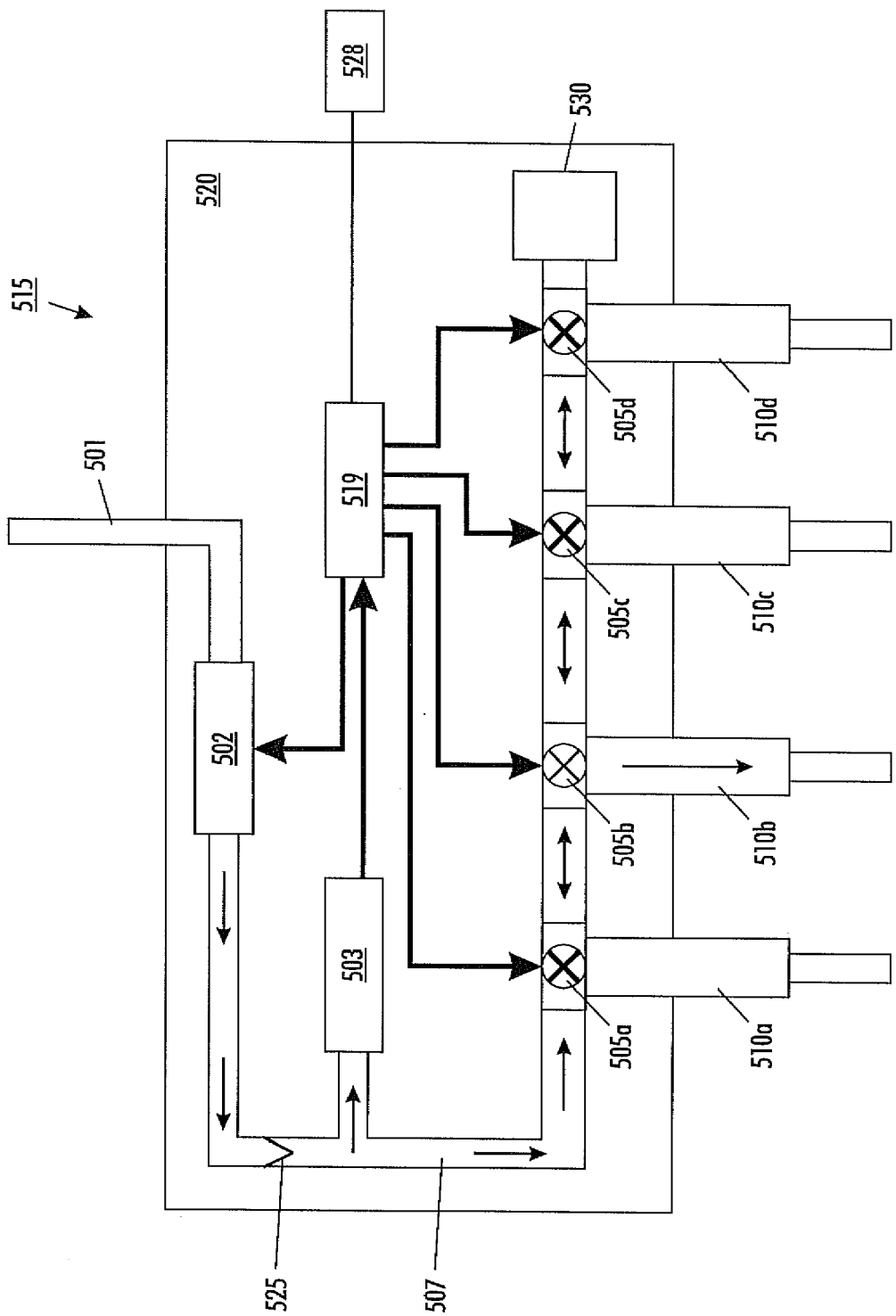
FIGS. 37-40 illustrate an inflation scheme according to one embodiment of the present invention.

FIG. 37 shows a console system generally indicated by 515 for enabling the application of pressure to a body limb. It is assumed for this discussion that the system 515, as illustrated in FIG. 37, is connected to a pressure sleeve-pressure accumulator combination as illustrated in FIG. 41.

The console system shown in FIGS. 37-40 is used when it is desired to apply pressure rapidly to a portion of a body limb. The console 515 is preferably portable and battery operated and includes an air compressor 502.

It is noted that air compressor 502 may be bypassed with pressurized air from an external source. The pressurized air would be introduced into the console 515 through pressurized air inlet 501.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

As further illustrated in FIGS. 37-40, a control unit 519 is attached to a sensor 528. The sensor 528 monitors the respiration cycle and provides signals to the control unit 515. The sensor 528 is a sensor or system that provides the monitoring data of the respiration cycle; i.e., the present invention contemplates using ECG signals, EMG signals, spirometer flow signals, strain gauges that sense the circumference of the abdomen, sensors that change their signals according to the chest impedance, microphones that can sense the breathing sounds, or the equivalents thereof. Moreover, the sensor 528 may be an autonomic air pletismographic device which utilizes the employment of a pneumatic cuff that encircles a segment of the body part being examined. In a preferred embodiment, this pneumatic cuff may encircle the patient's calf. An increase or decrease in the volume of the body part being examined will produce a similar change in the pressure of the captive air (the captive air being the air within the pneumatic cuff, and this pressure change can be recorded with a suitable transducer. As noted above, the monitoring of the respiration cycle is only one example of monitoring the venous phasic flow of the patient. The sensor 528 may be any sensor that is capable of providing data relative to the venous phasic flow.

Moreover, FIGS. 37-40 illustrate that the sensor 528 is directly connected to the pump unit 91; however, it is noted that the sensor 528 can also provide the data to the control unit 519 through a radio signal or similar means of communication, thus the sensor 528 need not be physically connected to the control unit 519, only in communication therewith.

Upon receiving this data, the control unit 515 controls the operations so that external pressure/compression generated venous flow is in-phase with the natural venous phasic flow. In the example of FIGS. 37-40, the realization of the external pressure/compression generated venous flow being in-phase with the natural venous phasic flow is the external pressure/compression generated venous flow being in-phase with an expiration phase or periods of low intra-abdominal pressure.

In this application, the valve 505b is opened (in FIGS. 37-40, an open valve is denoted by light or non-bolded crossed lines) while the valves 505a, 505c, 505d, and release valve 530 are closed (in FIGS. 37-40, a closed valve is denoted by heavy or bolded crossed lines), causing pressurized air to flow in the conduit 507 (in FIGS. 37-40, arrows within the conduit 507 generally show the flow of air and double-ended arrows indicate either non-air flow or air flowing in both direction as dictated by the present pressure drops in the conduit 507) from the compressor 502 through the valve 505b into the tubular conduit 510b associated with a pressure accumulator (arrow indicating air flow away from console 520 to the accumulator connected to conduit 510b). It is noted that release valve 530 may also include a self-operated valve to allow the user to directly release the pressurized air from the system.

Figure 38:
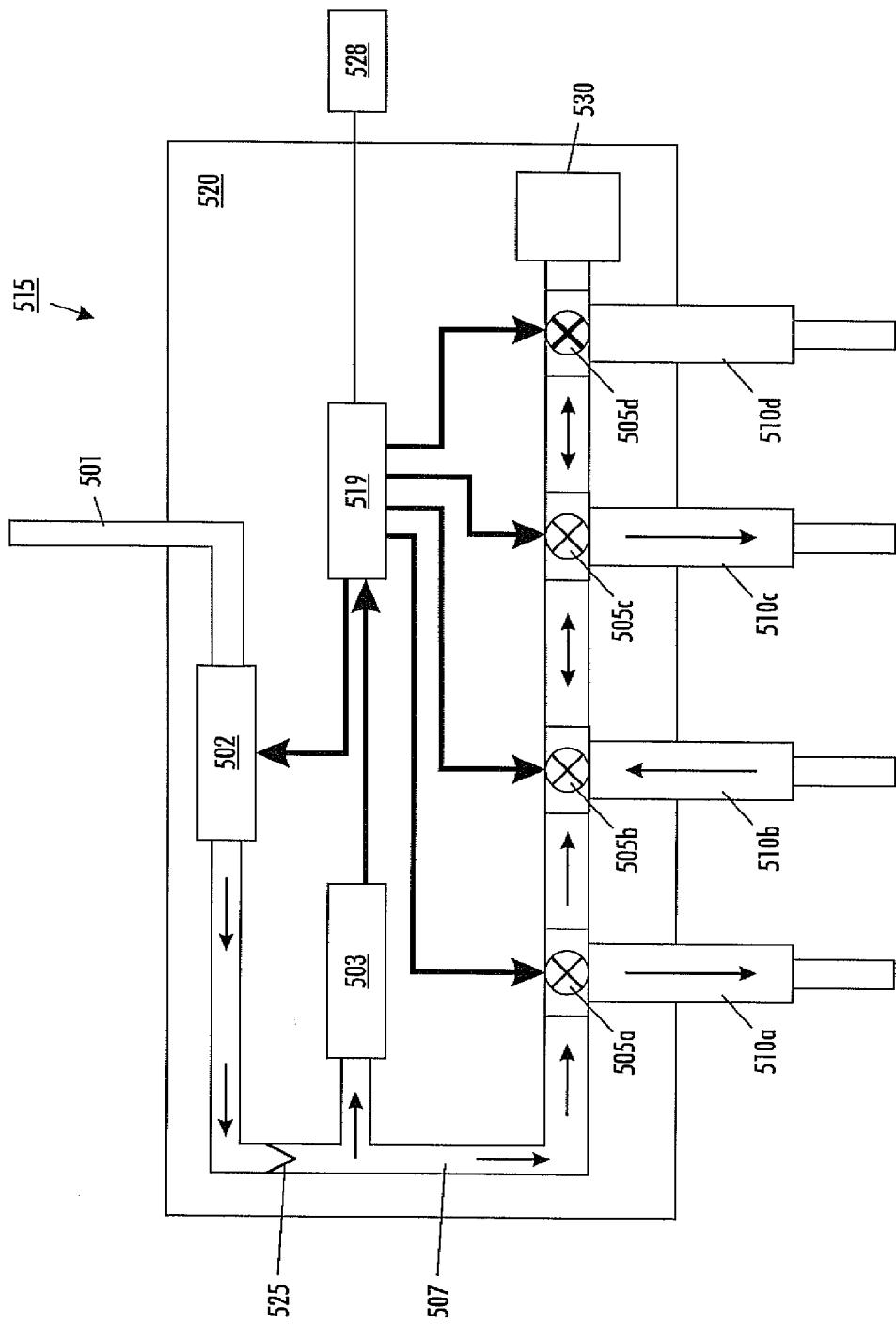

FIG. 38 illustrates the situation when the pressure in the pressure accumulator reaches a predetermined value $P_A$, as determined by the pressure gauge 503. As illustrated in FIG. 38, the processor opens the valve 505a causing air to flow from the associated pressure accumulator (see arrow indicating air flow from accumulator) into the cell (see arrow indicating air flow to cell). In this situation, valves 505a, 505b, and 505c are open, and valve 505d and the release valve 530 are closed. The one-way valve 525 prevents the flow of air in the conduit 507 from the pressure accumulator towards the compressor 502.

Figure 39:
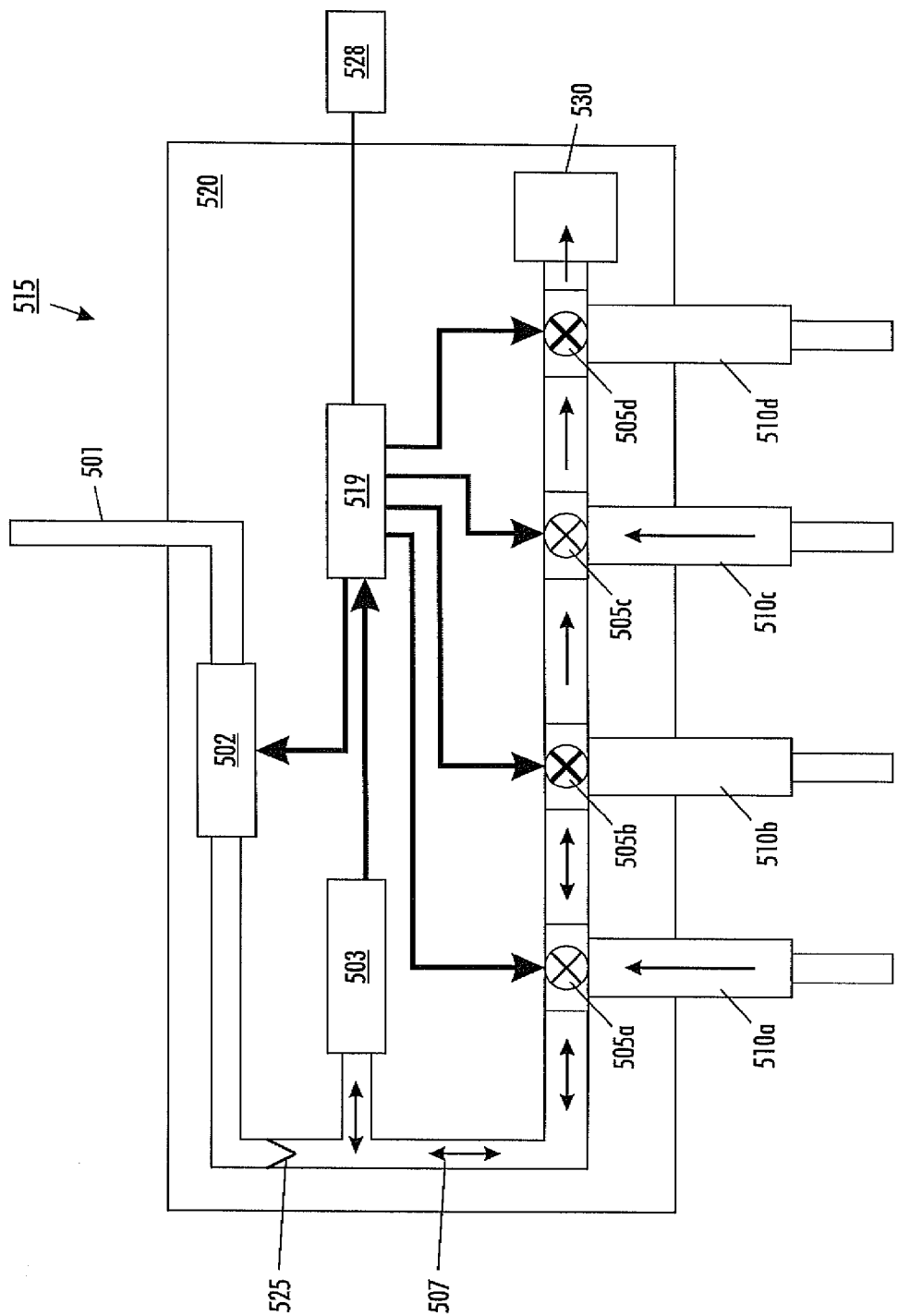

FIG. 39 illustrates the situation when the cell connected to the conduits 510a and 510c is deflated. As illustrated in FIG. 39, the processor closes the valve 505b. In this situation, valves 505a and 505c and the release valve 530 are open, and valves 505b and 505d are closed. The process illustrated in FIGS. 37-39 is repeated until the therapy is terminated.

Figure 40:
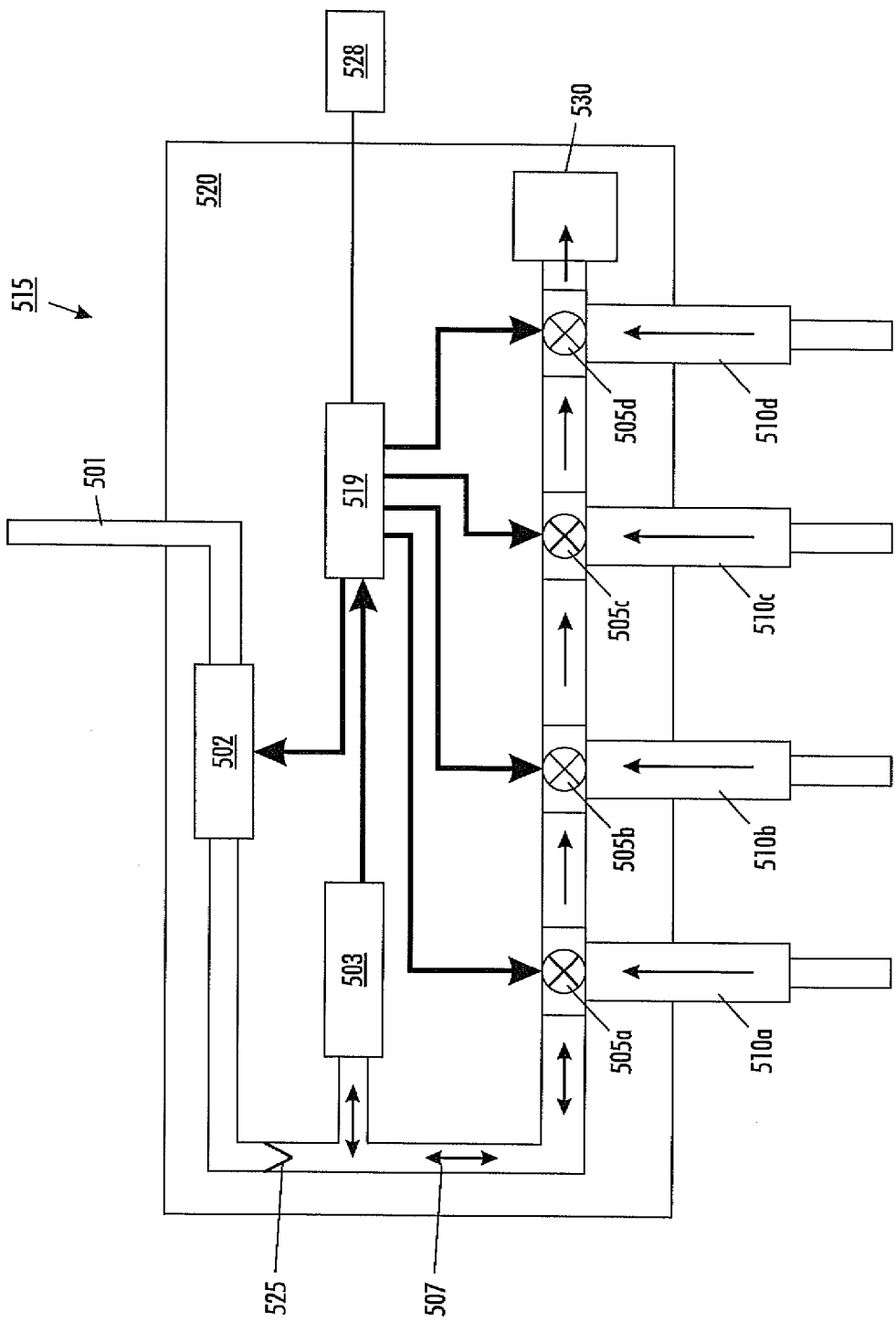

FIG. 40 illustrates the situation at the end of operations and all connected sleeves are deflated. As illustrated in FIG. 40, the processor opens all the valves to allow any pressurized air in a connected pressure device to be expelled through the release valve 530.

It is noted that the volume of a lower limb is directly affected by respiration. During inspiration there is a temporary reduction in the limb's venous return, which increases the total volume of the leg, while expiration has the opposite effect. Thus, the state or phase of respiration can be easily detected by air plethysmography of the calf.

According to the concepts of the present invention, air pletismograph encompasses the employment of a pneumatic cuff that encircles a segment of the body part being examined. In a preferred embodiment, this pneumatic cuff may encircle the patient's calf. An increase or decrease in the volume of the body part being examined will produce a similar change in the pressure of the captive air (the captive air being the air within the pneumatic cuff, and this pressure change can be recorded with a suitable transducer.

In a preferred embodiment of the present invention, the respiration state of the user of the external pressure/compression generation device is measured by a simple air plethysmograph.

Figure 45:
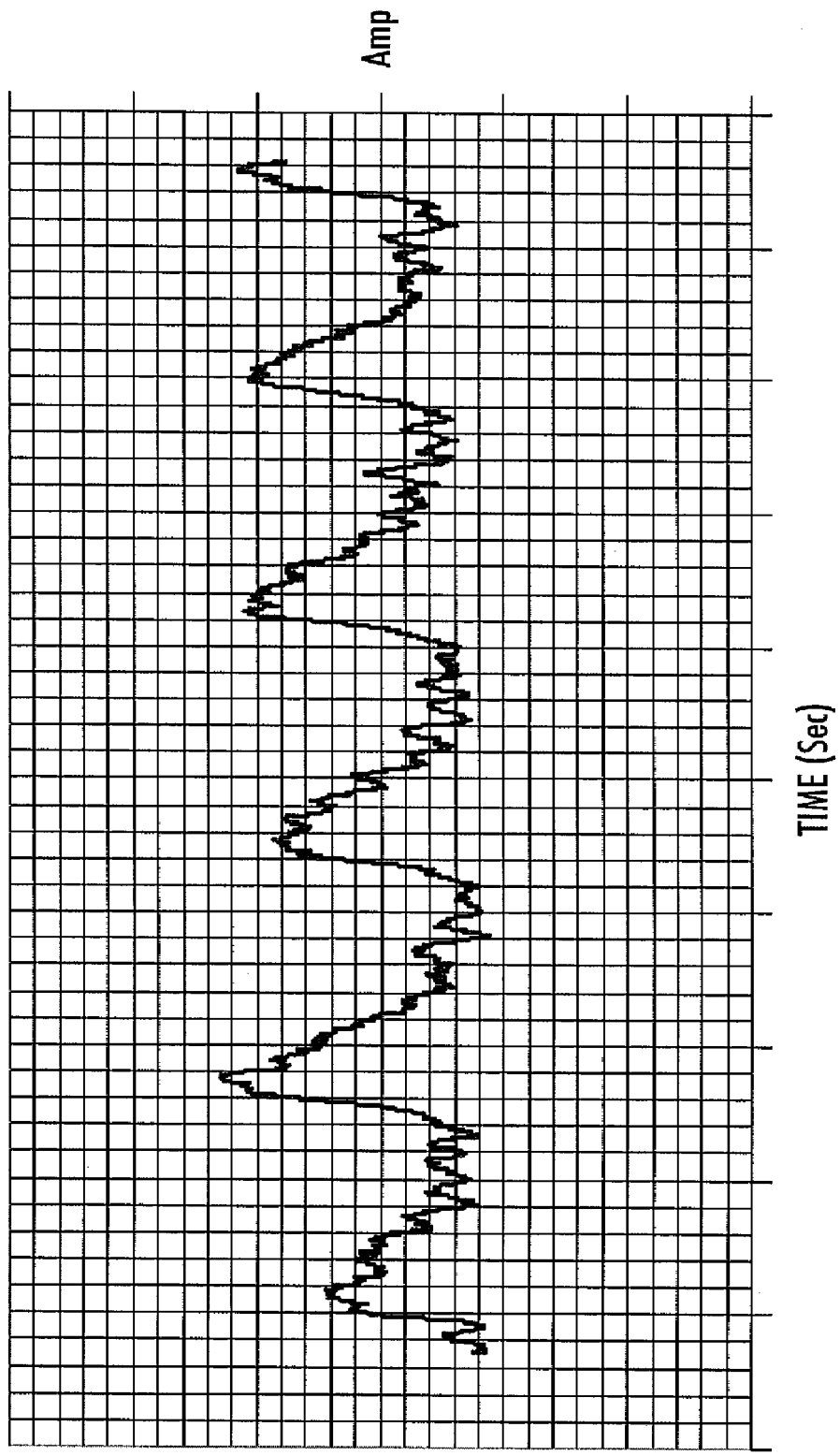
FIG. 45 is a graphical representation of a pressure curve obtained from partially deflated calf sleeve as recorded by the device pressure transducer according to the concepts of the present invention.

FIG. 45 illustrates a graph that is a representative pressure curve obtained from partially deflated calf sleeve as recorded by a device pressure transducer according to the concepts of the present invention. As illustrated by the graph of FIG. 45, both the respiratory waves and the pulse waves can be easily identified.

FIG. 50 illustrates one example of a pneumatic cuff assembly, according to the concepts of the present invention. As illustrated in FIG. 50, a pneumatic cuff assembly includes a connector 5000, which can provide pneumatic communication between the air bladder or cell 5250 of the pneumatic cuff 5200 and a pressure transducer which may be located in a console, via plug connector 5050 and flexible tube 5100. The pneumatic cuff 5200 the inflatable cell or air bladder 5250. The pressure of the inflatable cell or air bladder 5250 changes with the change in volume of the limb that it encircles. The pneumatic cuff 5200 also includes an attachment device 5275 to keep it secure around the limb.

It is noted that air plethysmography as a source for a respiratory synchronization signal is convenient to use and does not require extra sensors. Moreover, it is noted that one of the cell of an inflation sleeve could be easily transformed into a pneumatic cuff that is in pneumatic communication with a pressure transducer so as to measure the pressures differences to detect the states of respiration. It is further noted that the air pletismographic device may be autonomic so as to provide data representing a respiratory synchronization signal to the console of the compression device via hardwire, optical, and/or wireless communications.

It is noted that although air plethysmograph is subject to Boyle's law, which relates pressure, volume and temperature of a gas in a closed system, making the system sensitive to changes in temperature, sensitivity to temperature is not relevant to the operations of the present invention because temperature has only a minor effect on the wave contour illustrated in FIG. 45, the only parameter needed for synchronization.

Therefore, the present invention is capable of measuring or detecting the respiration state and uses this information for synchronized compression. The detection of the state of respiration can be successfully derived from pressure changes within the pneumatic sleeve itself. This information may be collected during the sleeve deflation period.

FIGS. 46-49 illustrate the operation of the present invention when a console, as illustrated in FIG. 19, is connected to a pressure device, such as the pressure sleeve and pressure accumulator of FIGS. 41 and 42 as described above, and a pneumatic cuff, such as illustrated in FIG. 50, as described above.

Figure 46:
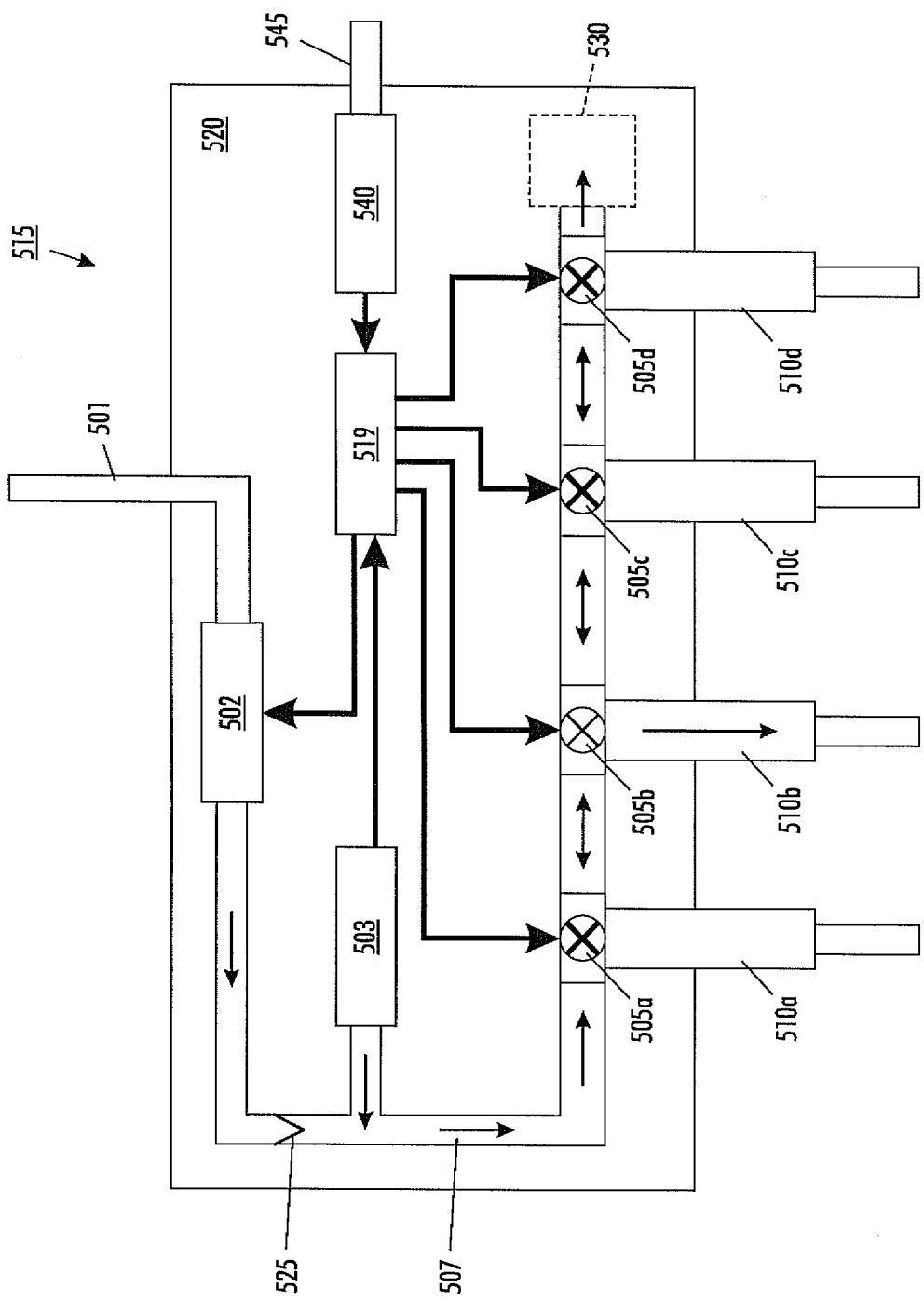
FIGS. 46-49 illustrate an inflation scheme according to another embodiment of the present invention.

FIG. 46 shows a console system generally indicated by 515 for enabling the application of pressure to a body limb. It is assumed for this discussion that the system 515, as illustrated in FIG. 46, is connected to a pressure sleeve-pressure accumulator combination as illustrated in FIG. 41.

The console system shown in FIGS. 46-49 is used when it is desired to apply pressure rapidly to a portion of a body limb. The console 515 is preferably portable and battery operated and includes an air compressor 502.

It is noted that air compressor 502 may be bypassed with pressurized air from an external source. The pressurized air would be introduced into the console 515 through pressurized air inlet 501.

Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

As further illustrated in FIGS. 46-49, a control unit 519 is attached to a pressure sensor 540. The pressure sensor 540 monitors the respiration cycle by detecting changes in pressure of a pneumatic cuff, such as illustrated in FIG. 50. The pneumatic cuff is in pneumatic communication with the pressure sensor 540 via port 545. Based upon the pressure measurements, the pressure sensor 540 provides signals to the control unit 515. The pressure sensor 540 may, preferably be part of an air plethysmography system that provides the monitoring data of the respiration cycle. As noted above, the monitoring of the respiration cycle is only one example of monitoring the venous phasic flow of the patient.

Moreover, FIGS. 46-49 illustrate that the pressure sensor 540 is directly connected to the pump unit 91; however, it is noted that the pressure sensor 540 can also provide the data to the control unit 519 through a radio signal or similar means of communication, thus the pressure sensor 540 need not be physically connected to the control unit 519, only in communication therewith. It is noted that in the example of FIG. 50, the pressure sensor 540 may actually be located in the connector 5000 and the pressure signals are communicated to the console via electrical wires.

Upon receiving this data, the control unit 519 controls the operations so that external pressure/compression generated venous flow is in-phase with the natural venous phasic flow. In the example of FIGS. 46-49, the realization of the external pressure/compression generated venous flow being in-phase with the natural venous phasic flow is the external pressure/compression generated venous flow being in-phase with an expiration phase or periods of low intra-abdominal pressure.

In this application, the valve 505b is opened (in FIGS. 46-49, an open valve is denoted by light or non-bolded crossed lines) while the valves 505a, 505c, 505d, and release valve 530 are closed (in FIGS. 46-49, a closed valve is denoted by heavy or bolded crossed lines), causing pressurized air to flow in the conduit 507 (in FIGS. 46-49, arrows within the conduit 507 generally show the flow of air and double-ended arrows indicate either non-air flow or air flowing in both direction as dictated by the present pressure drops in the conduit 507) from the compressor 502 through the valve 505b into the tubular conduit 510b associated with a pressure accumulator (arrow indicating air flow away from console 520 to the accumulator connected to conduit 510b). It is noted that release valve 530 may also include a self-operated valve to allow the user to directly release the pressurized air from the system.

Figure 47:
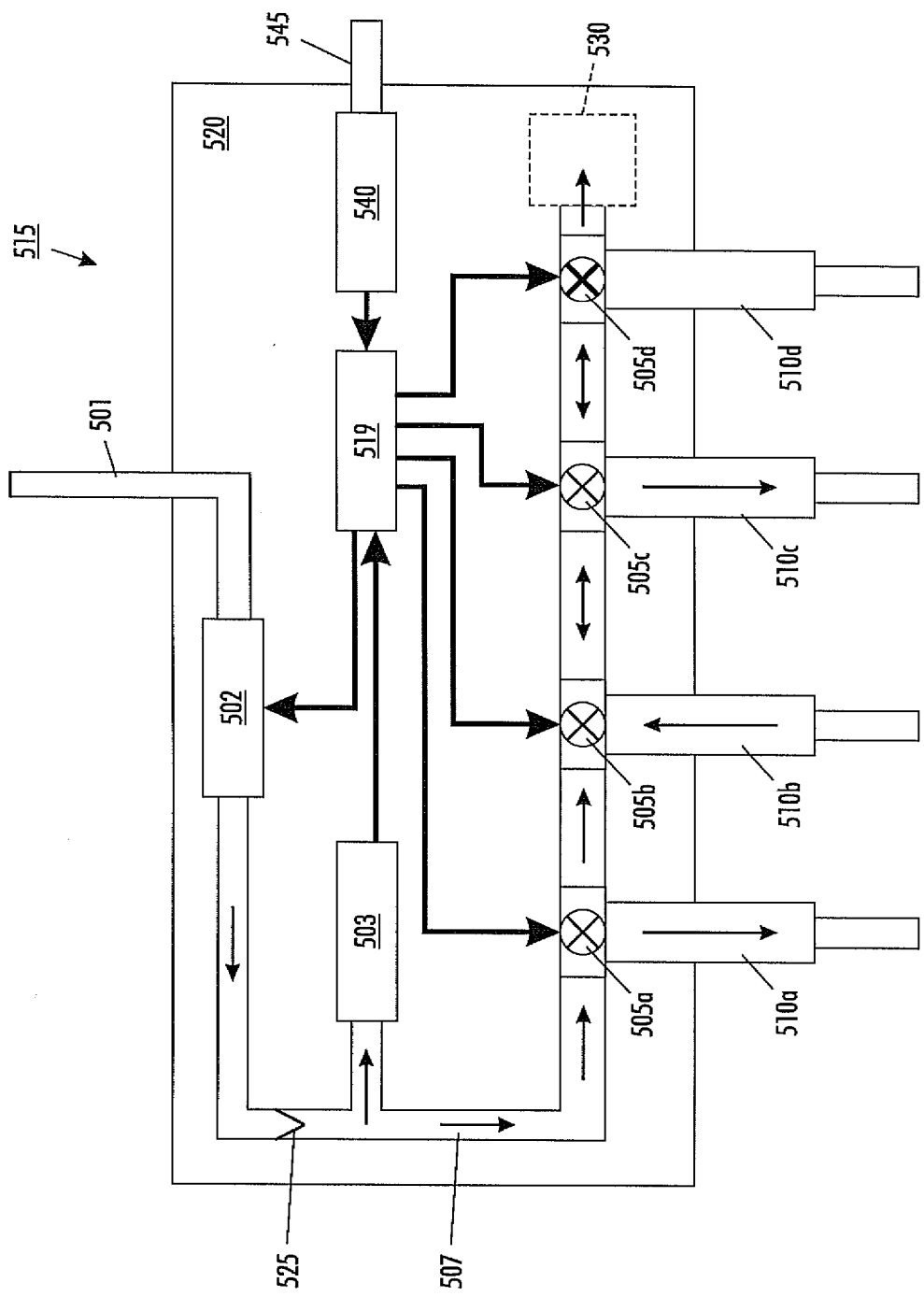

FIG. 47 illustrates the situation when the pressure in the pressure accumulator reaches a predetermined value $P_A$, as determined by the pressure gauge 503. As illustrated in FIG. 47, the processor opens the valve 505a causing air to flow from the associated pressure accumulator (see arrow indicating air flow from accumulator) into the cell (see arrow indicating air flow to cell). In this situation, valves 505a, 505b, and 505c are open, and valve 505d and the release valve 530 are closed. The one-way valve 525 prevents the flow of air in the conduit 507 from the pressure accumulator towards the compressor 502.

Figure 48:
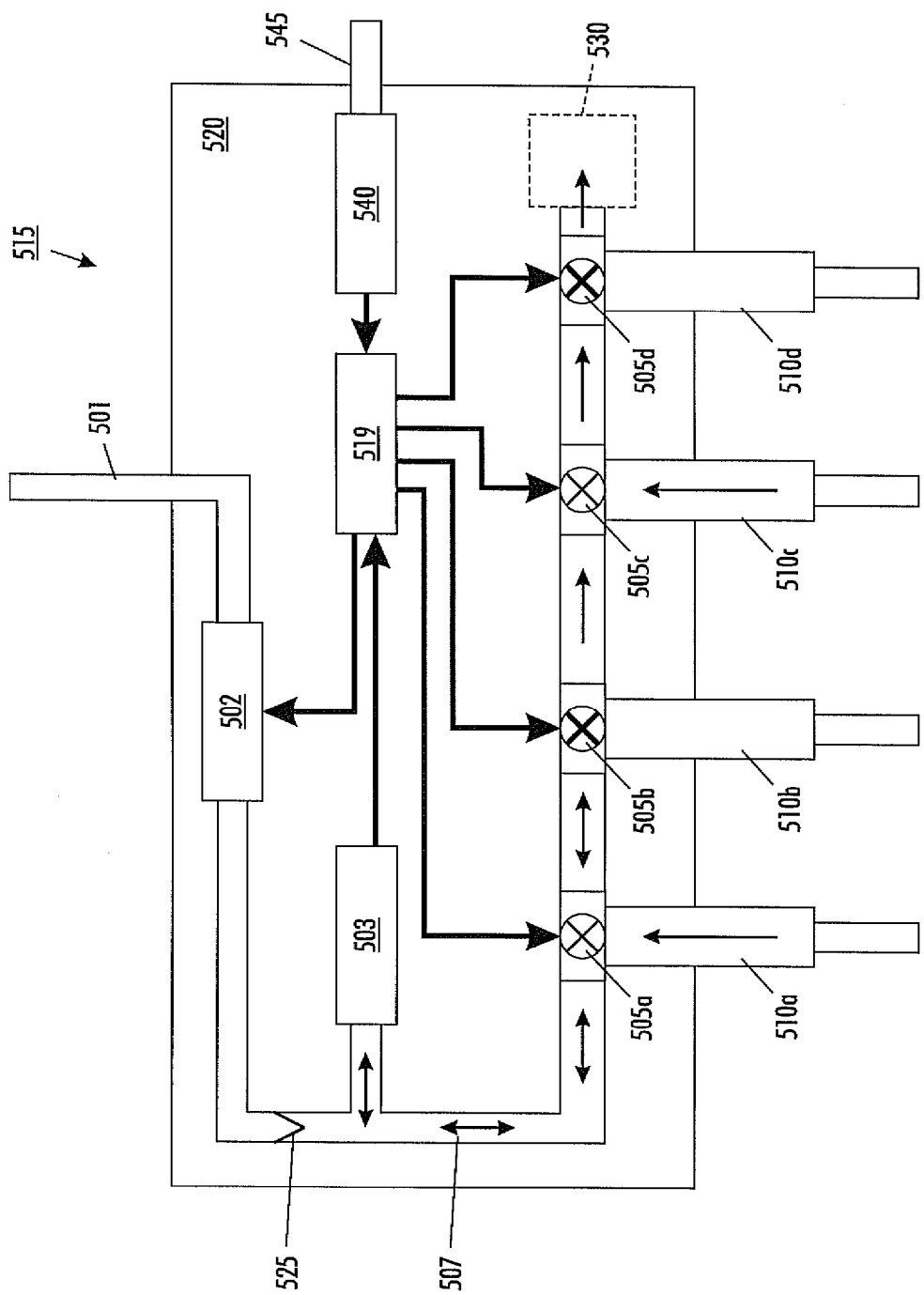

FIG. 48 illustrates the situation when the cell connected to the conduits 510a and 510c is deflated. As illustrated in FIG. 48, the processor closes the valve 505b. In this situation, valves 505a and 505c and the release valve 530 are open, and valves 505b and 505d are closed. The process illustrated in FIGS. 46-49 is repeated until the therapy is terminated.

Figure 49:
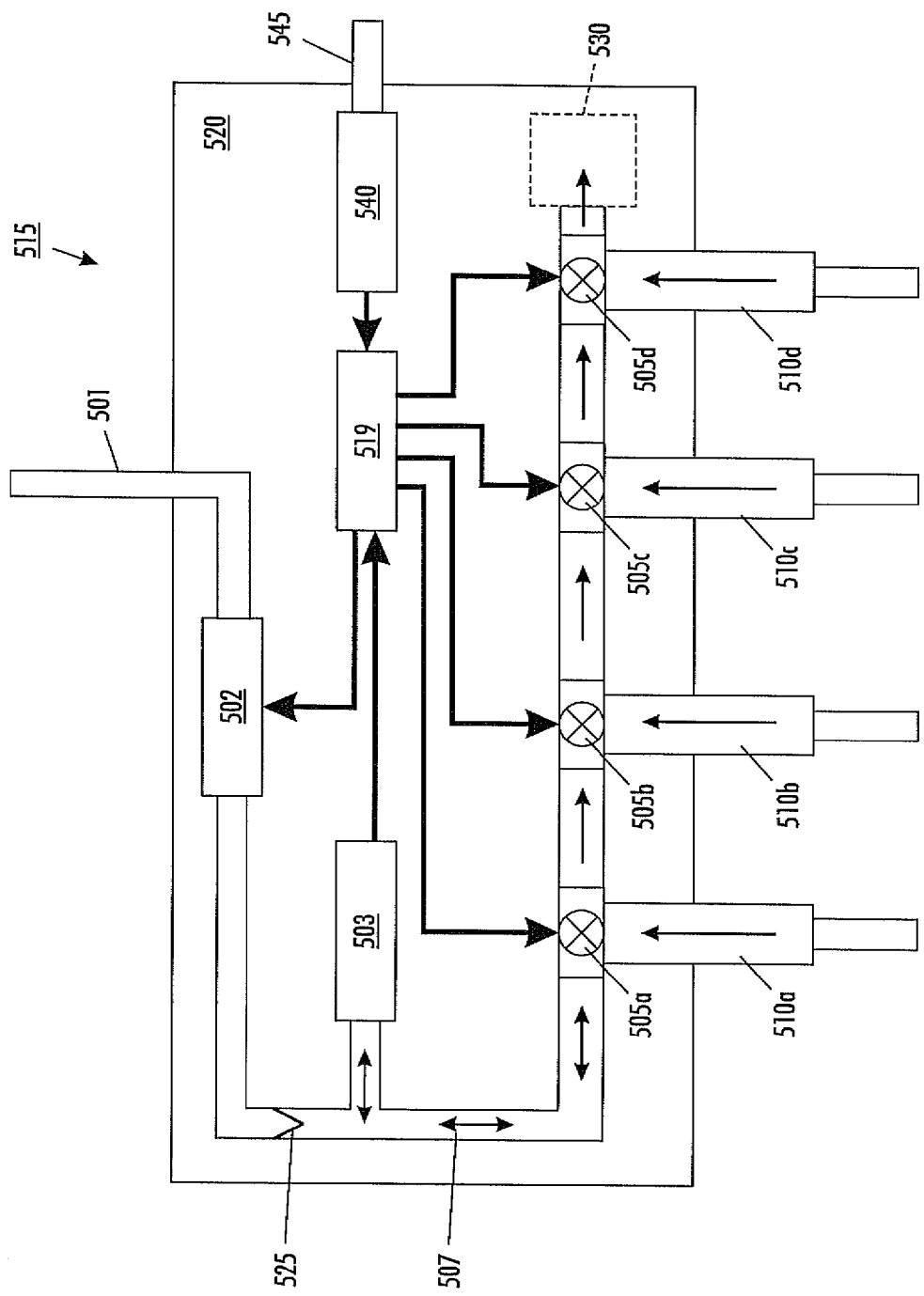

FIG. 49 illustrates the situation at the end of operations and all connected sleeves are deflated. As illustrated in FIG. 49, the processor opens all the valves to allow any pressurized air in a connected pressure device to be expelled through the release valve 530.

If the pneumatic cuff is one of the cells of a pressure sleeve, it is during the deflation period that the pressure in that cell is monitored. In such a situation, the valves associated with the non-monitored cells are closed, the valve associated with the monitored cell is opened, and the release valve 530 is closed. Thereafter, either the pressure gauge 503 or a separate pressure transducer; i.e., pressure transducer 540; measures the pressure within the monitored cell to determine the respiration state of the user.

As noted above, the volume of a lower limb is directly affected by respiration. During inspiration there is a temporary reduction in the limb's venous return, which increases the total volume of the leg, while expiration has the opposite effect. Thus, an increase or decrease in the volume of the body part being examined will produce a similar change in the pressure of the captive air (the captive air being the air within the pneumatic cuff, and this pressure change can be recorded with a suitable transducer.

If a cell within the pressure sleeve is to be used as the pneumatic cuff or captive air cell, the various codes discussed above to enable the console to detect the type of pressure sleeve connected to it would be modified such that console would know which cell provide the dual function of compression and limb volume measurement for the purposes of detecting a state of respiration. This code would cause the console to control the valves in the various manners described above wherein after deflation, a cell would remain active for the purposes of measuring the volume of a limb to determine the state of respiration. Again, it is noted that the air pletismographic device may be autonomic so as to provide data representing a respiratory synchronization signal to the console of the compression device via hardwire, optical, and/or wireless communications.

In summary, the present invention is directed to a compression system for applying therapeutic pressure (pneumatic and/or non-pneumatic) to a limb of a body. In one embodiment, the compression system includes a pressure sleeve; a compression system console, pneumatically connected to the pressure sleeve, having a controller and compressor to provide controlled pressurized fluid to the pressure sleeve; and a pressure accumulator, flexibly tethered and pneumatically connected to the compression system console, to provide controlled pneumatic compression.

To increase the peak venous velocity generated by any kind of external compressive force on a limb with any kind of tempo-spatial regime, the present invention synchronizes the external pressure generated venous flow with the in-phasic natural flow; e.g., periods of lower intra-abdominal pressure. On the other hand, the external pressure generated venous flow being out of phase with the venous phasic flow; e.g., during increased intra-abdominal pressure; significantly decreases the peak venous velocity in the lower limbs. Therefore, the present invention synchronizes the pressure generated venous flow, as created by the inflation of the pressure/compression sleeves of an external compression system, to be in-phase with the natural venous phasic flow; e.g., periods of lower intra-abdominal pressure.

The pressure sleeve may include an inflatable cell. The inflatable cell may include at least two intra-cell compartments, the intra-cell compartments being confluent and each compartment being elongated in a direction of the primary axis. The inflatable cell may further include inner and outer shells of durable flexible material, the inner and outer shells being bonded together about a perimetric cell bond ands being further bonded together along compartmental bonds within the perimetric cell bond to define each intra-cell compartment. The perimetric cell bond includes upper and lower perimetric cell bonds. The compartmental bonds partly extend between the upper and lower perimetric cell bonds and include perforations to allow for confluent airflow between adjacent intra-cell compartments within the cell. Adjacent intra-cell compartments are spatially fixed relative to each other, such that upon inflation of the cell, the cell becomes circumferentially constricted.

The bonds include welds. The adjacent intra-cell compartments are contiguous, and the perforations are located adjacent the perimetric cell bond. The perforations are also located between compartmental bonds extending from the upper and lower perimetric bonds.

The pressure accumulator includes a fastener device to fasten the pressure accumulator to a user of the compression system. The compression console system is portable, battery operated with a rechargeable battery. The compression system indicates an appropriate inflation and deflation sequence.

The pressure sleeve of the present invention may include an integral pressure accumulator and an inflatable cell operatively pneumatically connected to the integral pressure accumulator. The pressure sleeve of the present invention may also be a therapeutic foot device that includes a pressure sleeve; a sole member; and a pressure accumulator provided in the sole member and operatively pneumatically connected to the pressure sleeve.

As described above, the present invention also contemplates a therapeutic pressure system that includes a pressure sleeve and a compression system console, pneumatically connected to the pressure sleeve, having a controller and compressor to provide controlled pressurized fluid to the pressure sleeve. The controller, upon entering a first mode, identifies a type of the pressure sleeve connected to the compression system console. The therapeutic pressure system further includes a plurality of solenoids to convey pressurized air from the compressor to air conduits. The controller causes individual solenoids to activate so that the compressor supplies pressurized air through the activated solenoid to determine if a proper pressure device is connected thereto through an associated air conduit. The present invention also contemplates a therapeutic pressure system that includes a compression device that applies compression to a limb in synchronization with venous phasic flow. The compression device may produce pneumatic or non-pneumatic compression or pressure upon the limb.

Although the various embodiments of the pressure sleeves of the present invention have been described in conjunction with a portable compression system console or small compression system console wherein the source of the pressurized air was within the console, the pressure sleeves of the present invention can be used with any compression system wherein the source of pressurized air may be without the console.

For example, it is contemplated by the present invention that the source of the air pressure for inflation of the pressure sleeves can be located in the patient's bed or be built into the wall of a room. This source of pressurized air can be directly connected to the pressure sleeves via proper air conduits (assuming that a pressure control device that regulates or control the delivery of pressurized air to the pressure sleeves is associated with the pressurized air source) or can be connected to the pressure sleeves of the present invention through a control device or system that regulates or control the delivery of pressurized air to the pressure sleeves of the present invention.

In other words, the present invention contemplates a system where the source of pressurized air is integral with the pressure control device or a system where the source of pressurized air is not integral with the pressure control device. Again, it is noted that the application of pressure/compression to cause venous flow in a patient may be realized in many ways, such as pneumatic generated pressure, mechanical generated pressure, or electrical stimulus created internal pressure, or a combination. In a preferred embodiment of the present invention, the application of pressure/compression to cause venous flow in a patient is realized by a pneumatic system.

What is claimed is:

1. A system for applying pressure to a limb of a body, comprising:
   a compression system to provide controlled therapeutic pressure to a limb of a body to generate an induced venous flow; and
   a sensor, in operative communication with said compression system, to measure a venous phasic flow of a patient and to provide data representing the measured venous phasic flow to said compression system;
   said compression system, in response to said sensor, providing controlled therapeutic pressure to a limb of a body such that the induced venous flow generated by said compression system will be in-phase with the measured venous phasic flow of the patient.

2. The system as claimed in claim 1, wherein said compression system comprises:
   a pressure sleeve; and
   a compression system console, pneumatically connected to said pressure sleeve, having a controller to provide controlled pressurized fluid to said pressure sleeve;
   said compression system console, in response to said sensor, providing controlled pressurized fluid to said pressure sleeve such that the induced venous flow generated by said compression system will be in-phase with the measured venous phasic flow of the patient.

3. The system as claimed in claim 1, wherein said compression system provides controlled mechanical pressure to a limb of a body to generate the induced venous flow.

4. The system as claimed in claim 1, wherein said compression system provides an electrical stimulus to cause muscles of a limb of a body to contract and generate the induced venous flow.

5. The system as claimed in claim 1, wherein said compression system comprises:
   a pressure sleeve;
   a compression system console, pneumatically connected to said pressure sleeve, having a controller to provide controlled pressurized fluid to said pressure sleeve; and
   a pressure accumulator, pneumatically connected to said compression system console, to provide controlled pneumatic compression;
   said compression system console, in response to said sensor, providing controlled pressurized fluid to said pressure sleeve such that the induced venous flow generated by said compression system will be in-phase with the measured venous phasic flow of the patient.

6. The system as claimed in claim 1, wherein said sensor is autonomic.

7. The system as claimed in claim 1, wherein said sensor is an air pletysmographic device.

8. The system as claimed in claim 1, wherein said compression system comprises:
   a pressure sleeve having a plurality of inflatable cells, each inflatable cell being able to provide compression to a limb of the body, one of said plurality of inflatable cells being able to provide captive air for measuring a volume of the limb of the body; and
   a compression system console, pneumatically connected to said pressure sleeve, having a controller to provide controlled pressurized fluid to said pressure sleeve;
   said sensor being in pneumatic communication with said inflatable cell being able to provide captive air for measuring a volume of the limb of the body;

said sensor measuring a change in pressure in the captive air of said inflatable cell, the change in pressure corresponding to a venous phasic flow of the patient;

said compression system console, in response to said sensor, providing controlled pressurized fluid to said pressure sleeve such that the induced venous flow generated by said compression system will be in-phase with the venous phasic flow of the patient.

9. The system as claimed in claim 1, wherein said compression system comprises:

a pressure sleeve having a plurality of inflatable cells, each inflatable cell being able to provide compression to a limb of the body;

a pneumatic cuff to provide captive air for measuring a volume of the limb of the body; and a compression system console, pneumatically connected to said pressure sleeve and said pneumatic cuff, having a controller to provide controlled pressurized fluid to said pressure sleeve;

said sensor being in pneumatic communication with said pneumatic cuff and measuring a change in pressure in the captive air of said pneumatic cuff, the change in pressure corresponding to a venous phasic flow of the patient;

said compression system console, in response to said sensor, providing controlled pressurized fluid to said pressure sleeve such that the induced venous flow generated by said compression system will be in-phase with the venous phasic flow of the patient.

10. A compression system for applying therapeutic pressure to a limb of a body, comprising:

a pressure sleeve; and a compression system console, pneumatically connected to said pressure sleeve, having a controller to provide controlled pressurized fluid to said pressure sleeve such that said controlled pressurized fluid induces a venous flow in-phase with a venous phasic flow of a patient.

11. The compression system as claimed in claim 10, further comprising a pressure accumulator, pneumatically connected to said compression system console, to provide controlled pneumatic compression.

12. A system for applying pressure to a limb of a body, comprising:

a compression system to provide controlled therapeutic pressure to a limb of a body to generate an induced venous flow; and a respiration sensor, in operative communication with said compression system, to measure a respiration cycle of a patient and to provide data representing the measured respiration cycle to said compression system;

said compression system, in response to said respiration sensor, providing controlled therapeutic pressure to a limb of a body such that the induced venous flow generated by said compression system will be in-phase with a venous phasic flow of the patient.

13. The system as claimed in claim 12, wherein said compression system, in response to said respiration sensor, provides controlled therapeutic pressure to a limb of a body such that the induced venous flow generated by said compression system will be in-phase with an exhaling phase of the measured respiration cycle.

14. The system as claimed in claim 12, wherein said compression system, in response to said respiration sensor, provides controlled therapeutic pressure to a limb of a body such that the induced venous flow generated by said compression system will be in-phase with an inhaling phase of the measured respiration cycle.

15. The system as claimed in claim 12, wherein said compression system comprises:

a pressure sleeve; and a compression system console, pneumatically connected to said pressure sleeve, having a controller to provide controlled pressurized fluid to said pressure sleeve;

said compression system console, in response to said sensor, providing controlled pressurized fluid to said pressure sleeve such that the induced venous flow generated by said compression system will be in-phase with a venous phasic flow of the patient.

16. The system as claimed in claim 12, wherein said compression system provides controlled mechanical pressure to a limb of a body to generate the induced venous flow.

17. The system as claimed in claim 12, wherein said compression system provides an electrical stimulus to cause muscles of a limb of a body to contract and generate the induced venous flow.

18. The system as claimed in claim 12, wherein said compression system comprises:

a pressure sleeve;

a compression system console, pneumatically connected to said pressure sleeve, having a controller to provide controlled pressurized fluid to said pressure sleeve; and a pressure accumulator, pneumatically connected to said compression system console, to provide controlled pneumatic compression;

said compression system console, in response to said sensor, providing controlled pressurized fluid to said pressure sleeve such that the induced venous flow generated by said compression system will be in-phase with a venous phasic flow of the patient.

19. The system as claimed in claim 12, wherein said compression system provides controlled therapeutic pressure to a limb of a body such that the induced venous flow generated by said compression system will be in-phase with an exhaling phase of a respiration cycle.

20. The system as claimed in claim 12, wherein said compression system provides controlled therapeutic pressure to a limb of a body such that the induced venous flow generated by said compression system will be in-phase with an inhaling phase of a respiration cycle.

21. A method of providing therapy to a limb of a patient with a pressure device, comprising:

(a) monitoring a venous phasic flow of a patient; and (b) applying therapeutic pressure to a limb of the patient in-phase with the venous phasic flow of the patient.

22. The method as claimed in claim 21, wherein the applied therapeutic pressure is pneumatic pressure.

23. The method as claimed in claim 21, wherein the applied therapeutic pressure is mechanical pressure.

24. The method as claimed in claim 21, further comprising:

(c) determining if a predetermined amount of time has elapsed since a previous application of therapeutic pressure;

said application of therapeutic pressure to a limb of the patient being in-phase with the venous phasic flow of the patient and after the predetermined amount of time has elapsed since a previous application of therapeutic pressure.

25. A method of providing therapy to a limb of a patient with a pressure device, comprising:

(a) monitoring a respiration cycle of a patient;

(b) determining a venous phasic flow of the patient from the monitored respiration cycle; and (c) applying therapeutic pressure to a limb of the patient in-phase with the determined venous phasic flow of the patient.

26. The method as claimed in claim 25, wherein the applied therapeutic pressure is pneumatic pressure.

27. The method as claimed in claim 25, wherein the applied therapeutic pressure is mechanical pressure.

28. The method as claimed in claim 25, further comprising:
(d) determining if a predetermined amount of time has elapsed since a previous application of therapeutic pressure;
applying the therapeutic pressure to a limb of the patient in-phase with the determined venous phasic flow of the patient and after the predetermined amount of time has elapsed since a previous application of therapeutic pressure.

29. The method as claimed in claim 25, wherein the application of therapeutic pressure to a limb of the patient being in-phase with an exhaling phase of a respiration cycle.

30. The method as claimed in claim 25, wherein the application of therapeutic pressure to a limb of the patient being in-phase with an inhaling phase of a respiration cycle.

* * * * *

UNITED STATES PATENT AND TRADEMARK OFFICE
CERTIFICATE OF CORRECTION

PATENT NO.       : 7,637,879 B2
APPLICATION NO.  : 11/023894
DATED            : December 29, 2009
INVENTOR(S)      : Barak et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 979 days.

Signed and Sealed this

Ninth Day of November, 2010

David J. Kappos
*Director of the United States Patent and Trademark Office*